US011021533B2

(12) United States Patent
Crowe, Jr.

(10) Patent No.: US 11,021,533 B2
(45) Date of Patent: Jun. 1, 2021

(54) HUMAN ZIKA VIRUS ANTIBODIES AND METHODS OF USE THEREFOR

(71) Applicant: Vanderbilt University, Nashville, TN (US)

(72) Inventor: James E. Crowe, Jr., Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 0 days.

(21) Appl. No.: 16/346,709

(22) PCT Filed: Nov. 1, 2017

(86) PCT No.: PCT/US2017/059531
§ 371 (c)(1),
(2) Date: May 1, 2019

(87) PCT Pub. No.: WO2018/085400
PCT Pub. Date: May 11, 2018

(65) Prior Publication Data

US 2019/0276520 A1 Sep. 12, 2019

Related U.S. Application Data

(60) Provisional application No. 62/416,260, filed on Nov. 2, 2016.

(51) Int. Cl.

*A61K 39/42* (2006.01)
*A61P 31/14* (2006.01)
*C07K 16/10* (2006.01)
*G01N 33/569* (2006.01)
*A61K 39/00* (2006.01)

(52) U.S. Cl.

CPC .......... *C07K 16/1081* (2013.01); *A61K 39/42* (2013.01); *A61P 31/14* (2018.01); *G01N 33/56983* (2013.01); *A61K 2039/505* (2013.01); *A61K 2039/545* (2013.01); *A61K 2039/55* (2013.01); *C07K 2317/21* (2013.01); *C07K 2317/24* (2013.01); *C07K 2317/31* (2013.01); *C07K 2317/565* (2013.01); *C07K 2317/76* (2013.01); *C07K 2317/92* (2013.01); *G01N 2333/18* (2013.01); *G01N 2333/185* (2013.01); *Y02A 50/30* (2018.01)

(58) Field of Classification Search

None
See application file for complete search history.

(56) References Cited

U.S. PATENT DOCUMENTS

| | | | |
|---|---|---|---|
| 2011/0014211 A1 | 1/2011 | Azuma et al. |
| 2011/0300156 A1 | 12/2011 | Verploegen et al. |
| 2015/0086555 A1 | 3/2015 | Olsen et al. |

FOREIGN PATENT DOCUMENTS

| | | | |
|---|---|---|---|
| WO | WO/94/09136 | * | 4/1999 |
| WO | WO 2010-093335 | | 8/2010 |

OTHER PUBLICATIONS

Vajdos et al., Comprehensive Functional Maps of the Antigenbinding Site of an Anti-ErbB2 Antibody Obtained with Shotgun Scanning Mutagenesis, 2002, Journal of Molecular Biology, vol. 320, pp. 415-428.*
Sapparapu et al., Neutralizing human antibodies prevent Zika virus replication and fetal disease in mice, 2016, Nature, vol. 540, No. 7633, pp. 443-447.*
Andrews, Sarah F., et al. "Immune history profoundly affects broadly protective B cell responses to influenza." *Science translational medicine* 7.316 (2015): 316ra192-316ra192.
Davidson, Edgar, and Benjamin J. Doranz. "A high-throughput shotgun mutagenesis approach to mapping B-cell antibody epitopes." *Immunology* 143.1 (2014): 13-20.
International Preliminary Report on Patentability issued in International Application PCT/US2017/059531, dated May 16, 2019.
International Search Report and Written Opinion in International Application No. PCT/US17/59531, dated Feb. 21, 2018.
Martinez, Micaela Elvira. "Preventing Zika virus infection during pregnancy using a seasonal window of opportunity for conception." *PLoS biology* 14.7 (2016): e1002520.
Pal, Pankaj, et al. "Development of a highly protective combination monoclonal antibody therapy against Chikungunya virus." *PLoS Pathogens* 9.4 (2013): e1003312.
Pauli, Noel T., et al. "*Staphylococcus aureus* infection induces protein A—mediated immune evasion in humans." *Journal of Experimental Medicine* 211.12 (2014): 2331-2339.
Shukla, Shruti, et al. "Rapid detection strategies for the global threat of Zika virus: current state, new hypotheses, and limitations." *Frontiers in microbiology* 7 (2016): 1685.
Zhao, Haiyan, et al. "Structural basis of Zika virus-specific antibody protection." *Cell* 166.4 (2016): 1016-1027.
European Search Report issued in European Application No. 17866585.7, dated Jun. 2, 2020.
Stettler, Karin, et al. "Specificity, cross-reactivity, and function of antibodies elicited by Zika virus infection." *Science* 353.6301 (2016): 823-826.

* cited by examiner

*Primary Examiner* — Benjamin P Blumel
(74) *Attorney, Agent, or Firm* — Parker Highlander PLLC

(57) ABSTRACT

The present disclosure is directed to antibodies binding to and neutralizing Zika virus and methods for use thereof.

20 Claims, 11 Drawing Sheets

Specification includes a Sequence Listing.

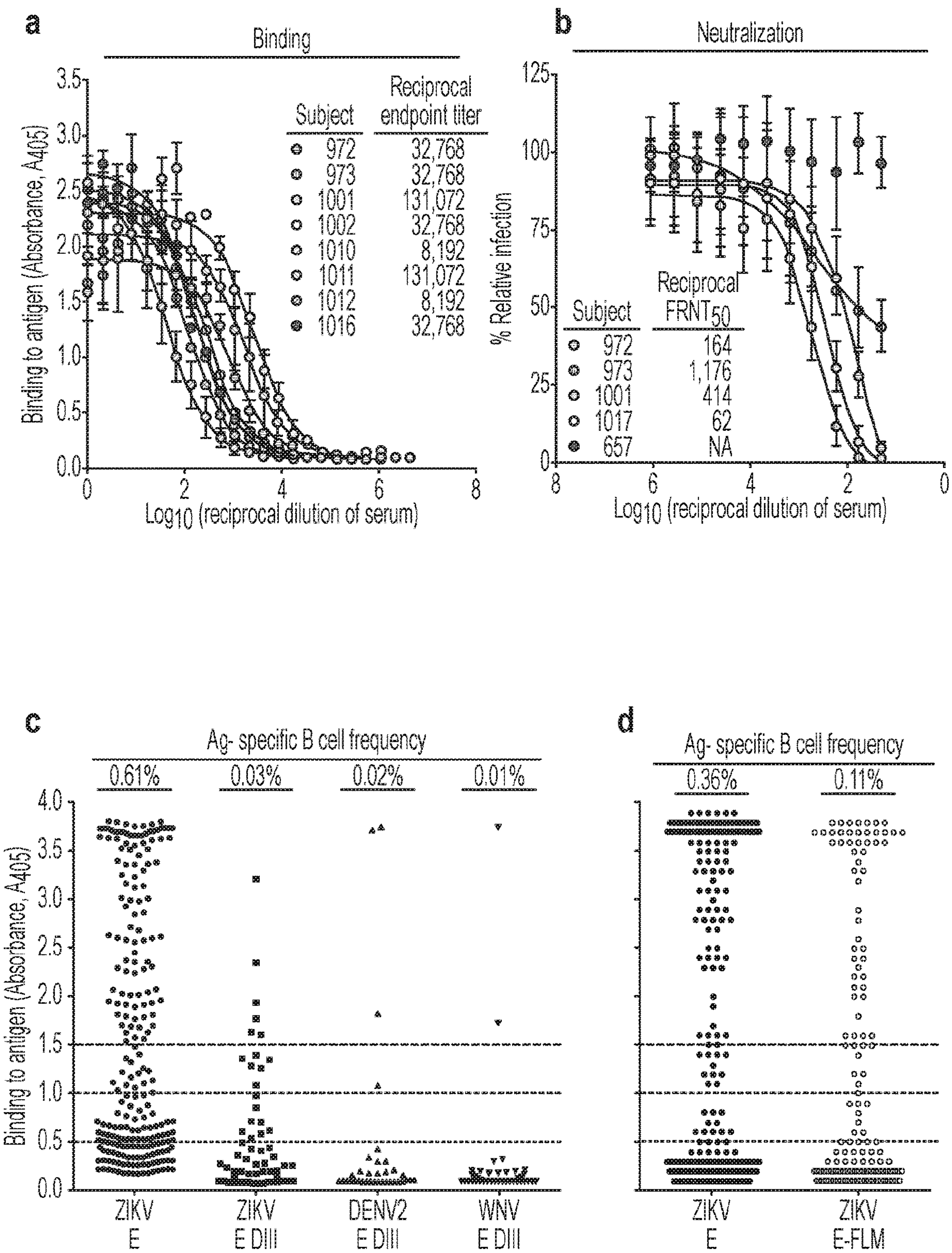
FIGS. 1A-D

| a | | Second antibody | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| Competition group | | A | | | | | | | | | | | | | | | | | | | | | | | B | C | | D | | |
| EC50(ng/ml) | | 37 | 49 | 46 | 43 | 34 | 43 | 328 | 74 | 34 | 89 | 53 | 101 | 47 | 43 | 48 | 58 | 46 | 48 | 70 | 62 | 104 | 88 | 95 | 75 | 165 | 82 | 695 | 48 | 52 |
| IC50(ng/ml) | | -- | -- | -- | -- | -- | -- | -- | -- | -- | -- | -- | -- | -- | -- | -- | -- | -- | -- | 420 | -- | -- | -- | -- | 16 | -- | -- | 347 | -- | 5 |
| First antibody | mAbs | 2 | 8 | 12 | 15 | 27 | 33 | 46 | 47 | 48 | 49 | 50 | 55 | 70 | 71 | 78 | 81 | 82 | 86 | 88 | 145 | 158 | 165 | 218 | 116 | 19 | 190 | 195 | 204 | 117 |
| A | 2 | -15 | -9 | -21 | -22 | 4 | -11 | -30 | -17 | -11 | -14 | -19 | -4 | -18 | 0 | -13 | -8 | -15 | -14 | -16 | -14 | -13 | -16 | -3 | 104 | 150 | 93 | 185 | 144 | 123 |
| A | 8 | -13 | -7 | -14 | -15 | 5 | -5 | -18 | -13 | -8 | -9 | -14 | -1 | -12 | 3 | -7 | -7 | -9 | -9 | -9 | -4 | -12 | -10 | 1 | 96 | 145 | 87 | 179 | 141 | 120 |
| A | 12 | -8 | -5 | -12 | -10 | 11 | -1 | -20 | -10 | -8 | -9 | -9 | 1 | -9 | 6 | -2 | -5 | -7 | -7 | -5 | -6 | -7 | -8 | 3 | 91 | 139 | 81 | 170 | 137 | 114 |
| A | 15 | -15 | -6 | -15 | -16 | 5 | -4 | -24 | -16 | -7 | -13 | -15 | -3 | -13 | 4 | -6 | -7 | -15 | -12 | -13 | -9 | -11 | -10 | 3 | 74 | 125 | 72 | 165 | 119 | 103 |
| A | 27 | -10 | -8 | -7 | -13 | 5 | -2 | -20 | -11 | -6 | -8 | -11 | 1 | -6 | 6 | -2 | -4 | -6 | -8 | -7 | -4 | -6 | -7 | 3 | 77 | 133 | 77 | 86 | 142 | 110 |
| A | 33 | -15 | -8 | -14 | -17 | 2 | -8 | -18 | -14 | -8 | -9 | -17 | 1 | -15 | 6 | -14 | -12 | -9 | -7 | -4 | -12 | -17 | -10 | -2 | 113 | 182 | 102 | 175 | 157 | 137 |
| A | 46 | 6 | 5 | 4 | 3 | 23 | 12 | -10 | -1 | 6 | 3 | -1 | 23 | 16 | 15 | 8 | 8 | 3 | 8 | 8 | 3 | 0 | 5 | 12 | 92 | 140 | 82 | 138 | 130 | 101 |
| A | 47 | -4 | -2 | -2 | -6 | 15 | 4 | -14 | -8 | -1 | -1 | -7 | 8 | -5 | 9 | -2 | -3 | -6 | 1 | 0 | -4 | -8 | -2 | 3 | 102 | 156 | 101 | 178 | 155 | 121 |
| A | 48 | -17 | -13 | -21 | -16 | 3 | -10 | -30 | -18 | -9 | -11 | -17 | -5 | -21 | 2 | -20 | -13 | -27 | -6 | -8 | -14 | -11 | -12 | -2 | 123 | 175 | 112 | 230 | 174 | 140 |
| A | 49 | -4 | -2 | -5 | 0 | 16 | 3 | -12 | -9 | 0 | -1 | -2 | 9 | -6 | 10 | -3 | -2 | -4 | 4 | 3 | -5 | -3 | -1 | 7 | 114 | 168 | 106 | 240 | 171 | 132 |
| A | 50 | -3 | -2 | -8 | -6 | 16 | 8 | -11 | -8 | 1 | -2 | -8 | 10 | 1 | 13 | -2 | 2 | -12 | -1 | 0 | -2 | -4 | 1 | 5 | 112 | 164 | 95 | 189 | 164 | 131 |
| A | 55 | -15 | -9 | -17 | -8 | 7 | -4 | -19 | -12 | -3 | -10 | -10 | -5 | -10 | 0 | -6 | -5 | -8 | -7 | -2 | -5 | -12 | -3 | 3 | 63 | 104 | 56 | 125 | 93 | 84 |
| A | 70 | -16 | -13 | -17 | -20 | 7 | -5 | -32 | -14 | -5 | -11 | -12 | -9 | -15 | -2 | -4 | -7 | -13 | -14 | -11 | -14 | -14 | -5 | -5 | 48 | 90 | 47 | 101 | 86 | 81 |
| A | 71 | -17 | -15 | -26 | -27 | -3 | -14 | -33 | -20 | -10 | -12 | -22 | -14 | -27 | -4 | -13 | -14 | -14 | -15 | -8 | -15 | -16 | -11 | -4 | 102 | 141 | 89 | 113 | 138 | 120 |
| A | 78 | -13 | -10 | -18 | -14 | 3 | -7 | -28 | -18 | -7 | -8 | -18 | -10 | -23 | 1 | -14 | -10 | -12 | -11 | -9 | -15 | -13 | -12 | -7 | 91 | 144 | 86 | 179 | 134 | 109 |
| A | 81 | -14 | -9 | -17 | -14 | 6 | -3 | -19 | -12 | -4 | -10 | -12 | -5 | -13 | 4 | -11 | -8 | -11 | -12 | -7 | -9 | -13 | -15 | -1 | 85 | 141 | 83 | 159 | 131 | 109 |
| A | 82 | -17 | -9 | -19 | -12 | 9 | -7 | -19 | -13 | -8 | -7 | -18 | 6 | -13 | 7 | -11 | -9 | -13 | -12 | -10 | -13 | -7 | -13 | -1 | 108 | 149 | 97 | 175 | 147 | 130 |
| A | 86 | -15 | -10 | -17 | -15 | 9 | -3 | -15 | -12 | -6 | -6 | -20 | 9 | -10 | 5 | -8 | -7 | -9 | -10 | -4 | -10 | -9 | -9 | 0 | 99 | 166 | 96 | 210 | 129 | 129 |
| A | 88 | -17 | -11 | -18 | -13 | 10 | -4 | -19 | -10 | -8 | -7 | -16 | 9 | -13 | 7 | -6 | -8 | -9 | -9 | -3 | -7 | -7 | -7 | -1 | 86 | 154 | 85 | 148 | 126 | 111 |
| A | 145 | -13 | -5 | -9 | -9 | 16 | 2 | -11 | -8 | -2 | -3 | -8 | 14 | -2 | 10 | 0 | 0 | -4 | -7 | 2 | -4 | -3 | 3 | 6 | 78 | 138 | 78 | 182 | 144 | 113 |
| A | 158 | -12 | -9 | -14 | -14 | 8 | -4 | -17 | -15 | -9 | -8 | -14 | -1 | -17 | 6 | -9 | -11 | -12 | -9 | -4 | -11 | -10 | -8 | 1 | 112 | 168 | 105 | 212 | 155 | 139 |
| A | 165 | -9 | -9 | -12 | -11 | 9 | -1 | -17 | -12 | -4 | -9 | -16 | -2 | -13 | 7 | -6 | -9 | -13 | -10 | -7 | -11 | -10 | -11 | -2 | 97 | 153 | 101 | 201 | 153 | 126 |
| A | 218 | -13 | -12 | -15 | -13 | 7 | -4 | -23 | -12 | -7 | -11 | -11 | -3 | -17 | 5 | -9 | -8 | -12 | -6 | -4 | -8 | -10 | -7 | 1 | 98 | 148 | 95 | 184 | 137 | 127 |
| B | 116 | 63 | 70 | 69 | 82 | 86 | 68 | 77 | 63 | 65 | 58 | 63 | 107 | 112 | 68 | 82 | 81 | 60 | 66 | 76 | 67 | 64 | 61 | 71 | 1 | 115 | 72 | 119 | 92 | 97 |
| C | 19 | 72 | 76 | 68 | 83 | 89 | 74 | 99 | 68 | 66 | 64 | 77 | 109 | 134 | 63 | 95 | 88 | 63 | 75 | 76 | 81 | 69 | 63 | 84 | 81 | -8 | -1 | 126 | 94 | 92 |
| C | 190 | 102 | 102 | 98 | 117 | 119 | 105 | 145 | 106 | 94 | 93 | 95 | 130 | 163 | 92 | 112 | 109 | 84 | 95 | 102 | 106 | 97 | 85 | 105 | 118 | -9 | -7 | 177 | 100 | 128 |
| D | 195 | 90 | 88 | 81 | 108 | 52 | 84 | 97 | 82 | 82 | 82 | 86 | 122 | 147 | 63 | 100 | 86 | 70 | 74 | 82 | 88 | 66 | 61 | 86 | 72 | 125 | 59 | 1 | 6 | 7 |
| D | 204 | 99 | 97 | 99 | 116 | 105 | 89 | 141 | 90 | 91 | 89 | 90 | 117 | 153 | 93 | 111 | 102 | 84 | 85 | 92 | 103 | 84 | 86 | 104 | 83 | 128 | 58 | -21 | -12 | -6 |
| D | 117 | 84 | 95 | 95 | 115 | 107 | 86 | 129 | 94 | 85 | 86 | 94 | 126 | 150 | 81 | 110 | 106 | 85 | 83 | 96 | 95 | 83 | 85 | 96 | 93 | 128 | 80 | -3 | -5 | 1 |

Strong competition (<30% residual binding) Intermediate competition (30 - 69% resdiual binding) No competition (>70% residual binding)

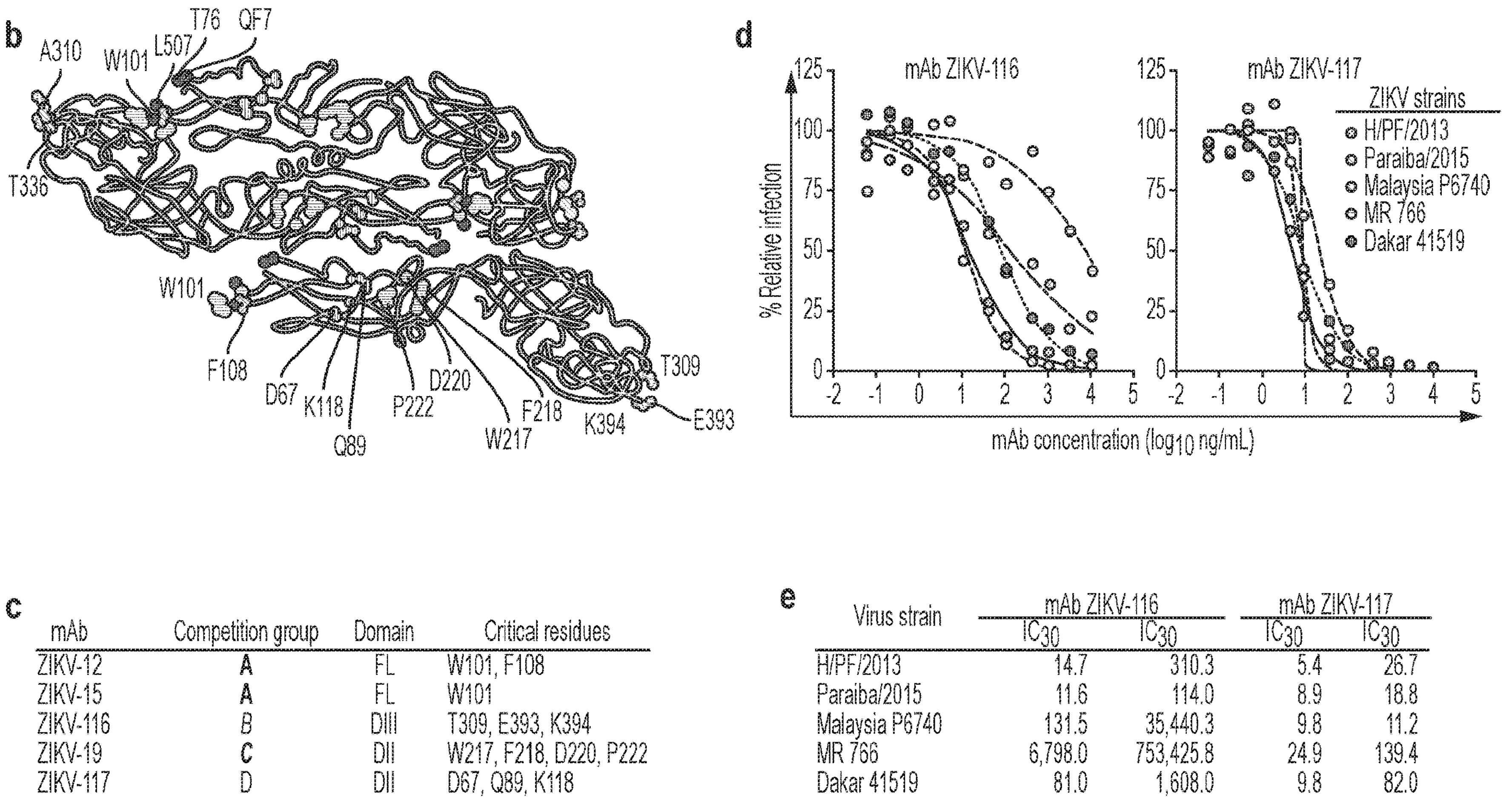
c
| mAb | Competition group | Domain | Critical residues |
|---|---|---|---|
| ZIKV-12 | **A** | FL | W101, F108 |
| ZIKV-15 | **A** | FL | W101 |
| ZIKV-116 | *B* | DIII | T309, E393, K394 |
| ZIKV-19 | ***C*** | DII | W217, F218, D220, P222 |
| ZIKV-117 | D | DII | D67, Q89, K118 |
e
| Virus strain | mAb ZIKV-116 | | mAb ZIKV-117 | |
|---|---|---|---|---|
| | $IC_{30}$ | $IC_{30}$ | $IC_{30}$ | $IC_{30}$ |
| H/PF/2013 | 14.7 | 310.3 | 5.4 | 26.7 |
| Paraiba/2015 | 11.6 | 114.0 | 8.9 | 18.8 |
| Malaysia P6740 | 131.5 | 35,440.3 | 9.8 | 11.2 |
| MR 766 | 6,798.0 | 753,425.8 | 24.9 | 139.4 |
| Dakar 41519 | 81.0 | 1,608.0 | 9.8 | 82.0 |
FIGS. 2B-E

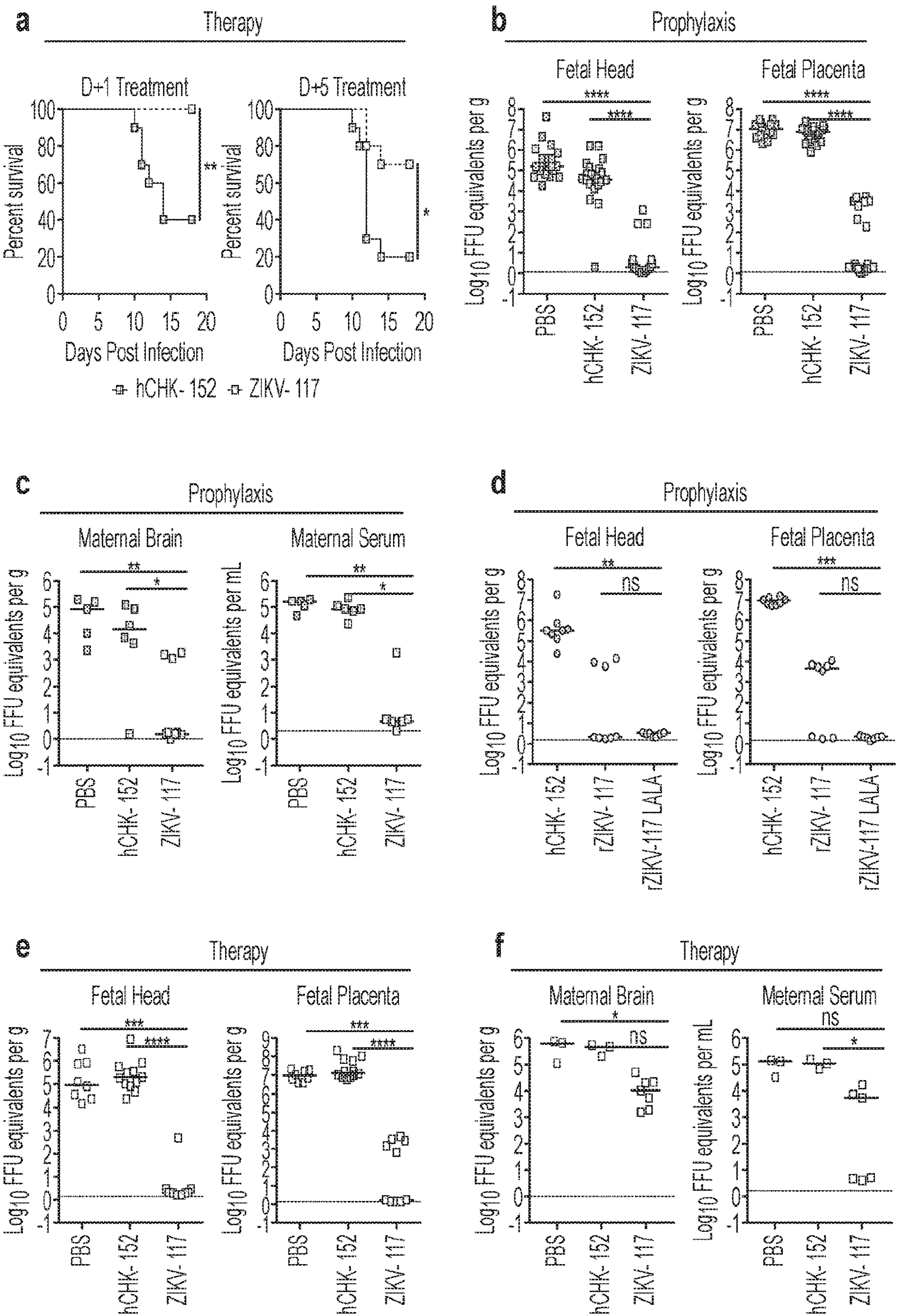
FIGS. 3A-F

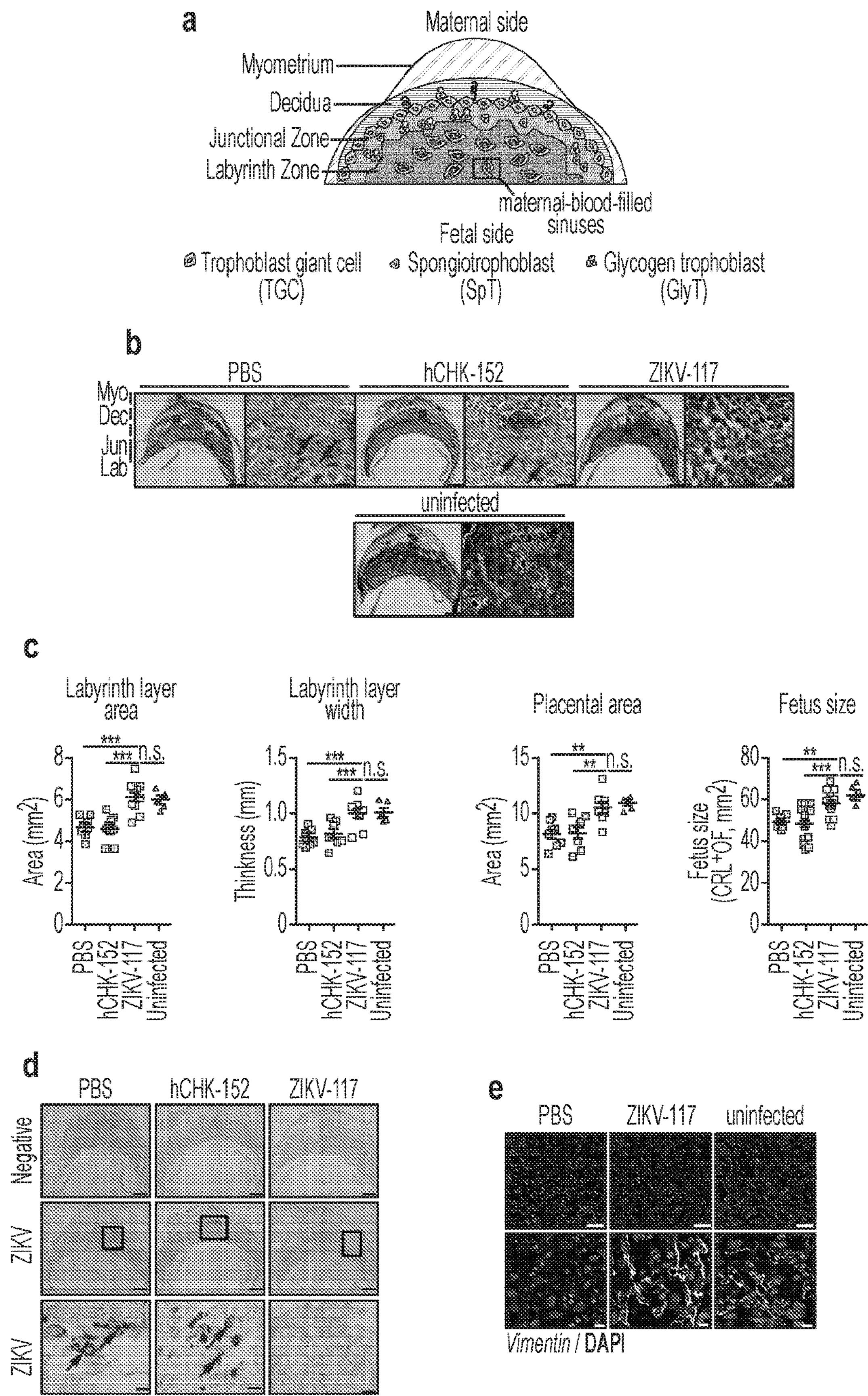
FIGS. 4A-E a

Figure 6A:
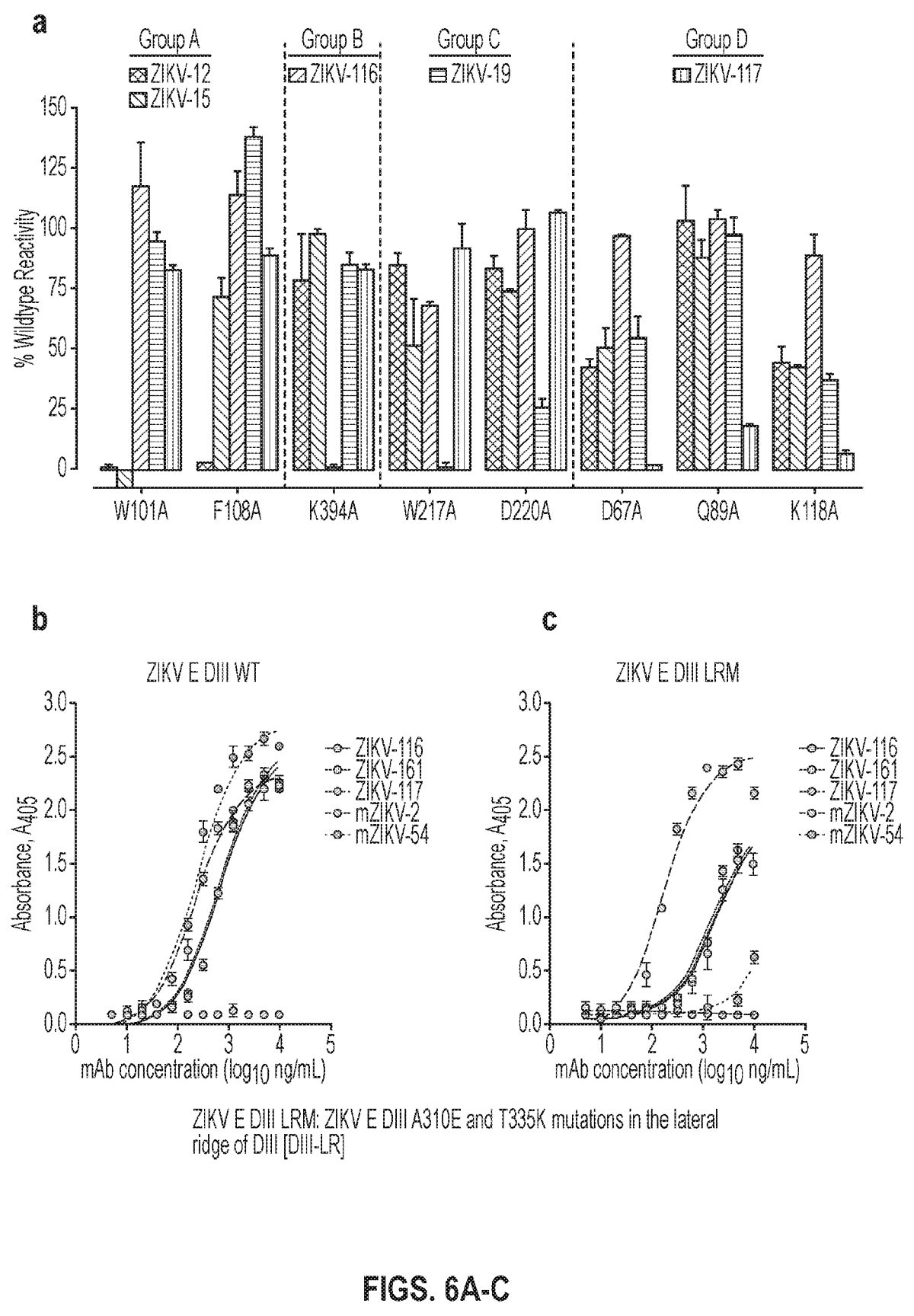

Group A: ZIKV-12, ZIKV-15
Group B: ZIKV-116
Group C: ZIKV-19
Group D: ZIKV-117

% Wildtype Reactivity 0, 25, 50, 75, 100, 125, 150

W101A F108A K394A W217A D220A D67A Q89A K118A b

ZIKV E DIII WT c

ZIKV E DIII LRM

Absorbance, $A_{405}$ 0.0, 0.5, 1.0, 1.5, 2.0, 2.5, 3.0 mAb concentration ($log_{10}$ ng/mL)

0 1 2 3 4 5

ZIKV-116
ZIKV-161
ZIKV-117
mZIKV-2
mZIKV-54

ZIKV E DIII LRM: ZIKV E DIII A310E and T335K mutations in the lateral ridge of DIII [DIII-LR]

FIGS. 6A-C

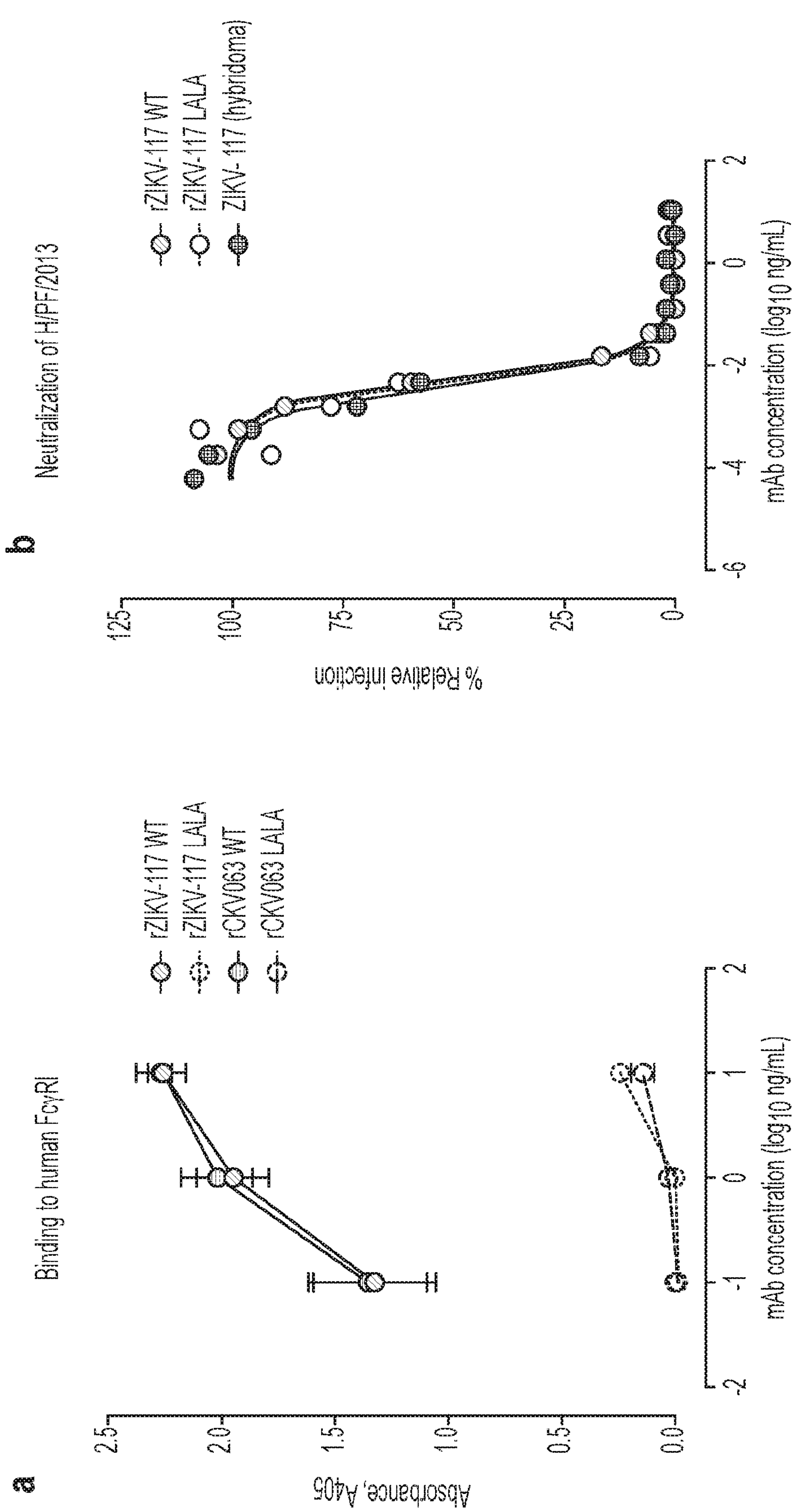
FIG. 9A-B

HUMAN ZIKA VIRUS ANTIBODIES AND METHODS OF USE THEREFOR

This application is a national phase application under 35 U.S.C. § 371 of International Application No. PCT/US2017/059531, filed Nov. 1, 2017, which claims benefit of priority to U.S. Provisional Application Ser. No. 62/461,260, filed Nov. 2, 2016, the entire contents of each of which are hereby incorporated by reference.

GOVERNMENT SUPPORT CLAUSE

This invention was made with government support under Grant No. R01 AI127828 awarded by the National Institutes of Health. The government has certain rights in the invention.

BACKGROUND

1. Field of the Disclosure

The present disclosure relates generally to the fields of medicine, infectious disease, and immunology. More particular, the disclosure relates to human antibodies binding to Zika virus (ZIKV).

2. Background

ZIKV is an emerging mosquito-transmitted flavivirus that has become a global public health threat. Recent ZIKV epidemics in Micronesia, Brazil, other parts of South and Central America, and Mexico (Duffy et al., 2009) are linked to Guillain-Barre syndrome in adults and microcephaly in newborn infants (Oehler et al., 2014; Musso et al., 2014) in the setting of infection during pregnancy (Araugo et al., 2016; Gatherer & Kohl, 2016). As ZIKV is transmitted by *Aedes* species mosquitoes, which are global in distribution, countries in which these vectors are present could be sites for future epidemics. Despite the potential for causing disease in millions, specific treatments or vaccines for ZIKV are not available, leaving a considerable unmet need in the field.

SUMMARY

Thus, in accordance with the present disclosure, a method of detecting a Zika virus infection in a subject comprising (a) contacting a sample from said subject with an antibody or antibody fragment having clone-paired heavy and light chain CDR sequences from Tables 3 and 4, respectively; and (b) detecting Zika virus in said sample by binding of said antibody or antibody fragment to a Zika virus antigen in said sample. The sample may be a body fluid, and may be blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in Zika virus antigen levels as compared to the first assay.

The antibody or antibody fragment is encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment.

Also provided is a method of treating a subject infected with Zika virus, or reducing the likelihood of infection of a subject at risk of contracting Zika virus, comprising delivering to said subject an antibody or antibody fragment having clone-paired heavy and light chain CDR sequences from Tables 3 and 4, respectively. The antibody or antibody fragment may be encoded by clone-paired light and heavy chain variable sequences as set forth in Table 1, may be encoded by clone-paired light and heavy chain variable sequences having 95% identify to as set forth in Table 1, or may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment, the antibody may be an IgG, or a recombinant IgG antibody or antibody fragment comprising an Fc portion mutated to eliminate FcR interactions, such as a LALA mutation or a LS mutation, and the antibody may be a chimeric antibody or a bispecific antibody. The antibody or antibody fragment may be administered prior to infection or after infection. The subject may be a pregnant female, a sexually active female, or a female undergoing fertility treatments. Delivering may comprises antibody or antibody fragment administration, or genetic delivery with an RNA or DNA sequence or vector encoding the antibody or antibody fragment.

In another embodiment, there is provided is a monoclonal antibody, wherein the antibody or antibody fragment is characterized by clone-paired heavy and light chain CDR sequences from Tables 3 and 4, respectively. The antibody or antibody fragment may be encoded by light and heavy chain variable sequences according to clone-paired sequences from Table 1, may be encoded by light and heavy chain variable sequences having at least 70%, 80%, or 90% identity to clone-paired sequences from Table 1, or may be encoded by light and heavy chain variable sequences having at least 95% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise antibody or antibody fragment comprises light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment. The antibody may be is a chimeric antibody, or is bispecific antibody. The antibody may be an IgG or a recombinant IgG antibody or antibody fragment comprising an Fc portion mutated to eliminate FcR interactions, such as a LALA or a LS mutation. The antibody or antibody fragment may further comprise a cell penetrating peptide and/or is an intrabody.

In further embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by light and heavy chain variable sequences according to clone-paired sequences from Table 1, may be encoded by light and heavy chain variable sequences having at least 70%, 80%, or 90% identity to clone-paired sequences from Table 1, or may be encoded by light and heavy chain variable sequences having at least 95% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise antibody or antibody fragment comprises light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment. The antibody may be is a chimeric antibody, or is bispecific antibody. The antibody may be an IgG, or a recombinant IgG antibody or antibody fragment comprising an Fc portion mutated to eliminate FcR interactions, such as a LALA or a LS mutation. The antibody or antibody fragment may further comprise a cell penetrating peptide and/or is an intrabody.

In yet a further embodiment, there is provided a vaccine formulation comprising one or more antibodies or antibody fragments characterized by clone-paired heavy and light chain CDR sequences from Tables 3 and 4, respectively. The antibody or antibody fragment may be encoded by light and heavy chain variable sequences according to clone-paired sequences from Table 1, may be encoded by light and heavy chain variable sequences having at least 70%, 80%, or 90% identity to clone-paired sequences from Table 1, or may be encoded by light and heavy chain variable sequences having at least 95% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise antibody or antibody fragment comprises light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment. The antibody may be is a chimeric antibody, or is bispecific antibody. The antibody may be an IgG, or a recombinant IgG antibody or antibody fragment comprising an Fc portion mutated to eliminate FcR interactions, such as a LALA or a LS mutation.

The vaccine formulation may comprise antibodies or antibody fragments that bind to E protein domain II. The vaccine formulation may comprise antibodies or antibody fragments that bind to E protein domain III, or to a quaternary epitope on the E protein dimer-dimer interface. The vaccine formulation may comprise antibodies or antibody fragments that do not cross react with dengue virus. The vaccine formulation may comprise antibodies or antibody fragments that neutralize Zika virus infections corresponding to African, Asian, and American lineages.

In still yet a further embodiment, there is provided a method of protecting the health of a placenta and/or fetus of a pregnant a subject infected with or at risk of infection with Zika virus comprising delivering to said subject an antibody or antibody fragment having clone-paired heavy and light chain CDR sequences from Tables 3 and 4, respectively. The antibody or antibody fragment may be encoded by light and heavy chain variable sequences according to clone-paired sequences from Table 1, may be encoded by light and heavy chain variable sequences having at least 70%, 80%, or 90% identity to clone-paired sequences from Table 1, or may be encoded by light and heavy chain variable sequences having at least 95% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise antibody or antibody fragment comprises light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment. The antibody may be is a chimeric antibody, or is bispecific antibody. The antibody may be an IgG, or a recombinant IgG antibody or antibody fragment comprising an Fc portion mutated to eliminate FcR interactions, such as a LALA or a LS mutation. The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control, and/or the antibody or antibody fragment reduces viral load and/or pathology of the fetus as compared to an untreated control.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-D. Human antibody and B cell response to ZIKV infection. Serum samples from humans with a previous diagnosis of ZIKV infection were tested for (FIG. 1A) binding to ZIKV E protein in ELISA (with two technical replicates) and (FIG. 1B) neutralization of ZIKV in a FRNT assay (performed with at least two independent repeats in triplicate). Subjects 973 and 972 sera were tested from two separate time points with similar results—these data were combined). Subject 1001 had the highest endpoint titer in the binding assay and displayed potent neutralizing activity. Subject 657 was a control without history of exposure to ZIKV. (FIG. 1C) Supernatants of EBV-transformed B cell cultures from Subject 1001 were tested for binding to ZIKV E or DIII of ZIKV E or related flavivirus E proteins to assess the specificity of the immune response. The frequency of antigen-specific cells against each viral protein was determined with a threshold optical density (OD) of 1.5; with alternate lower OD thresholds of 1.0 or 0.5, the frequency was 0.69% or 0.97% for ZIKV E, respectively. (FIG. 1D) In four additional separate B cell transformation experiments, the frequency of B cells reactive with intact ZIKV E or E-FLM was determined.

FIG. 2A-E. Characterization of anti-ZIKV mAbs. (FIG. 2A) 29 mAbs were tested in binding, neutralization, and competition binding assays. The half-maximal binding concentration ($EC_{50}$) against ZIKV E and the $IC_{50}$ (by focus reduction neutralization test) against H/PF/2013 strain for neutralizing antibodies (highlighted in blue) are shown. The mAbs are displayed in four groups (A, B, C, or D) based on a competition binding assay.

The values are the percent of binding that occurred during competition compared to uncompeted binding, which was normalized to 100% and the range of competition is indicated by the box colors. Black filled boxes indicate strongly competing pairs (residual binding <30%), grey filled boxes indicate intermediate competition (residual binding 30-69%), and white filled boxes indicate non-competing pairs (residual binding ≥70%). The $IC_{50}$ against H/PF/2013 strain for neutralizing antibodies is shown with active clones highlighted in blue. (FIG. 2B) A ribbon diagram of three protomers of ZIKV E (DI in red, DII in yellow and DIII in blue) is shown with critical residues highlighted as spheres from epitope mapping experiments for representative antibodies in each of the competition binding groups. The colors of the critical residues correspond to the competition group designation as in FIG. 2A. The mutations in the E-FLM and DIII-LR mutants are indicated by black and silver spheres, respectively. (FIG. 2C) Representative mAbs from each competition binding group are listed with the domains and residues critical for binding. (FIG. 2D) Two mAbs were tested for neutralization of five strains of ZIKV. The concentrations at which 50% or 90% neutralization occurred are listed in (FIG. 2E). The neutralization data are pooled from at least three independent experiments performed in triplicate.

FIGS. 3A-F. Protective activity of ZIKV-117 in adult male and pregnant female mice. (FIG. 3A) Four to five week-old WT male mice were treated with 2 mg of anti-Ifnar1 mAb followed by subcutaneous inoculation with $10^3$ FFU of mouse-adapted ZIKV-Dakar. Mice were treated with a single 100 μg or 250 μg dose of isotype control mAb (hCHK-152) or ZIKV-117 on D+1 or D+5 (n=10 per group from two independent experiments), respectively. Significance was analyzed by the log-rank test (*, P<0.05; , P<0.01). (FIGS. 3B-C) Ifnar $1^{-/-}$ female mice were mated with WT sires. At E5.5, dams were treated with 250 ug of either hCHK-152 isotype control mAb or ZIKV-117. Bars indicate the median values and reflect data pooled from four independent experiments. Significance for fetal survival and viral RNA was analyzed by chi-square (FIG. 3B; **, P<0.0001) and Mann-Whitney (FIG. 3C; *, P<0.05) tests, respectively. (FIGS. 3D-F) WT female mice were mated with WT sires. At E5.5, dams were treated with anti-Ifnar1 mAb and one of the following: (FIGS. 3D-E) PBS, (FIGS. 3D-F) 250 μg of hCHK-152 isotype control mAb, (FIGS. 3D-F) 250 μg of ZIKV-117, or (FIG. 3F) 250 μg of ZIKV-117 LALA. At E6.5, dams were inoculated with $10^3$ FFU of ZIKV-Dakar. (FIGS. 3D, 3F) Fetuses and placentas and (FIG. 3E) maternal brain and serum were harvested on E13.5 and viral RNA was measured by qRT-PCR. Bars indicate the median values of samples collected from three biological replicates (FIG. 3D): n=20 to 36; (FIG. 3E): n=5 to 9; f: n=23 to 28). Significance was analyzed by ANOVA with a Dunn's multiple comparison test (*, P<0.05; , P<0.01, *, P<0.001; ****, P<0.0001).

FIGS. 4A-E. Effect of ZIKV-117 treatment on the placenta and the fetus. (FIG. 4A) Cartoon depicting murine placental structures and zones. (FIG. 4B-E) Pregnant dams were treated with PBS, hCHK-152, or ZIKV-117 as described in (FIG. 4D-F) prior to infection with ZIKV-Dakar or mock-infected. (FIG. 4B) Hematoxylin and eosin staining of placenta at E13.5. Placental labyrinth zone is marked with a solid line. Low power (scale bar=1 mm) and high power (scale bar=50 μm) images are presented in sequence. Black arrows indicate apoptotic trophoblasts in areas corresponding to regions of ZIKV infectivity (see panel (FIG. 4D), below). (FIG. 4C) Measurements of thickness and indicated areas of placenta and fetus body size. Each symbol represents data from an individual placenta or fetus. Significance was analyzed by ANOVA with a Dunn's multiple comparison test (*, P<0.05; , P<0.01, *, P<0.001; ****, P<0.0001, n.s.; not significant, P>0.05). (FIG. 4D) In situ hybridization (ISH). Low power (scale bar=500 μm) and high power (scale bar=50 μm) images are presented in sequence. Black arrows indicate cells positive for ZIKV RNA in the junctional zone of the placenta. The images in panels are representative of several placentas from independent dams. (FIG. 4E). Low (scale bar=50 μm) and high (scale bar=10 μm) power magnified images of immunofluorescence staining of placentas for vimentin (in green, which marks fetal capillary endothelium) from ZIKV-infected dams treated with PBS or ZIKV-117 or from uninfected pregnant animals. Nuclei are counter-stained blue with DAPI.

FIGS. 6A-C. (FIG. 6A) High resolution epitope mapping of ZIKV mAbs. An alanine scanning mutation library for ZIKV envelope protein was constructed where each amino acid of prM/E was mutated individually to alanine (and alanine to serine) and expression constructs arrayed into 384-well plates, one mutation per well. Each clone in the ZIKV prM/E mutation library, expressed in HEK-293T cells, was tested for immunoreactivity with five mAbs from competition groups A-D, measured using an Intellicyt high-throughput flow cytometer. Shown here for each of the five mAbs is the reactivity with the ZIKV E protein mutants that identified the epitope residues for these mAbs. MAb reactivity for each alanine mutant are expressed as percent of the reactivity of mAb with wild-type ZIKV prM/E. Clones with reactivity <30% relative to WT ZIKV prM/E were identified as critical for mAb binding. Bars represent the mean and range of at least two replicate data points. Binding of Group B mAbs, ZIKV-116 and ZIKV-161, to (FIG. 6B) ZIKV E DIII WT or (FIG. 6C) DIII LR mutant was compared with mouse mAbs ZV-2 and ZV-54. Binding of ZIKV-116 and ZIKV-161 was decreased by mutations in DIII LR.

FIGS. 9A-B. Comparison of WT and LALA mutated antibodies. (FIG. 9A) Binding to recombinant human FcγR1. The functional abrogation of the binding of the LALA variant IgG was confirmed in an ELISA binding assay with recombinant human FcγRI. ZIKV-117 WT bound to FcγR1, whereas the ZIKV-117 LALA antibody did not. WT and LALA versions of another human mAb, CKV063, were used as controls. (FIG. 9B) Neutralization. ZIKV-117 WT and LALA antibodies exhibited equivalent neutralizing activity in vitro to each other and to the hybridoma-derived antibody.

DESCRIPTION OF ILLUSTRATIVE EMBODIMENTS

Figure 2A:
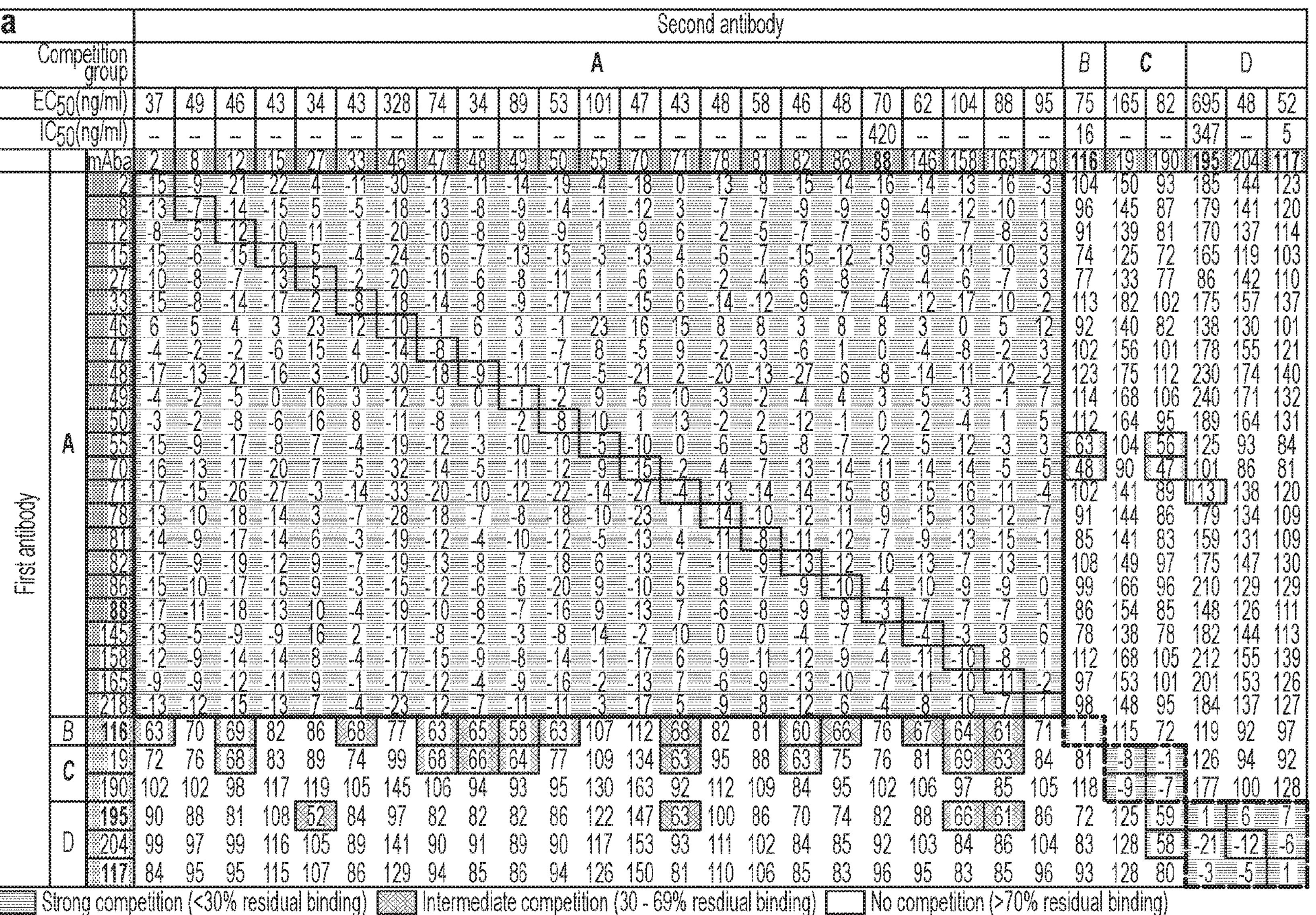

As discussed above, Zika virus (ZIKV) infection causes systemic and central nervous system pathology or disease, with congenital birth defects linked to infection during pregnancy (Coyne et al., 2016). To develop candidate therapeutic agents against ZIKV, the inventors isolated a panel of human monoclonal antibodies (mAbs) from healthy subjects with prior ZIKV infection. A subset of mAbs recognized diverse epitopes on the envelope (E) protein and exhibited potent neutralizing activity. One of the most inhibitory mAbs, ZIKV-117, broadly neutralized infection of ZIKV strains corresponding to African, Asian, and American lineages. Epitope mapping studies revealed that ZIKV-117 recognized a quaternary epitope on the E protein dimer-dimer interface. The inventors then evaluated the therapeutic efficacy of ZIKV-117 in pregnant or non-pregnant mice. In these models, mAb treatment markedly reduced tissue pathology, placental and fetal infection, and mortality. Thus, neutralizing human mAbs can protect against maternal-fetal transmission, infection and disease, and reveal important determinants for structure-based rational vaccine design efforts. These and other aspects of the disclosure are described in detail below.

I. Zika Virus

Zika virus (ZIKV) is a member of the virus family Flaviviridae. It is spread by daytime-active *Aedes* mosquitoes, such as *A. aegypti* and *A. albopictus*. Its name comes from the Zika Forest of Uganda, where the virus was first isolated in 1947. Zika virus is related to the dengue, yellow fever, Japanese encephalitis, and West Nile viruses. Since the 1950s, it has been known to occur within a narrow equatorial belt from Africa to Asia. From 2007 to 2016, the virus spread eastward, across the Pacific Ocean to the Americas, leading to the 2015-16 Zika virus epidemic.

The infection, known as Zika fever or Zika virus disease, often causes no or only mild symptoms, similar to a very mild form of dengue fever. While there is no specific treatment, paracetamol (acetaminophen) and rest may help with the symptoms. As of 2016, the illness cannot be prevented by medications or vaccines. Zika can also spread from a pregnant woman to her fetus. This can result in microcephaly, severe brain malformations, and other birth defects. Zika infections in adults may result rarely in Guillain-Barré syndrome.

In January 2016, the United States Centers for Disease Control and Prevention (CDC) issued travel guidance on affected countries, including the use of enhanced precautions, and guidelines for pregnant women including considering postponing travel. Other governments or health agencies also issued similar travel warnings, while Colombia, the Dominican Republic, Puerto Rico, Ecuador, El Salvador, and Jamaica advised women to postpone getting pregnant until more is known about the risks.

The Zika virus belongs to the Flaviviridae family and the *Flavivirus* genus, and is thus related to the dengue, yellow fever, Japanese encephalitis, and West Nile viruses. Like other flaviviruses, Zika virus is enveloped and icosahedral and has a nonsegmented, single-stranded, 10 kb positive-sense RNA genome. It is most closely related to the Spondweni virus and is one of the two known viruses in the Spondweni virus Glade.

A positive-sense RNA genome can be directly translated into viral proteins. As in other flaviviruses, such as the similarly sized West Nile virus, the RNA genome encodes seven nonstructural proteins and three structural proteins. One of the structural proteins encapsulates the virus. The RNA genome forms a nucleocapsid along with copies of the 12-kDa capsid protein. The nucleocapsid, in turn, is enveloped within a host-derived membrane modified with two viral glycoproteins. Viral genome replication depends on the synthesis of double sided RNA from the single stranded positive sense RNA (ssRNA(+)) genome followed by transcription and replication to provide viral mRNAs and new ssRNA(+) genomes.

There are two Zika lineages: the African lineage and the Asian lineage. Phylogenetic studies indicate that the virus spreading in the Americas is 89% identical to African genotypes, but is most closely related to the Asian strain that circulated in French Polynesia during the 2013-2014 outbreak.

The vertebrate hosts of the virus were primarily monkeys in a so-called enzootic mosquito-monkey-mosquito cycle, with only occasional transmission to humans. Before the current pandemic began in 2007, Zika "rarely caused recognized 'spillover' infections in humans, even in highly enzootic areas." Infrequently, however, other arboviruses have become established as a human disease and spread in a mosquito-human-mosquito cycle, like the yellow fever virus and the dengue fever virus (both flaviviruses), and the chikungunya virus (a togavirus). Though the reason for the pandemic is unknown, dengue, a related arbovirus that infects the same species of mosquito vectors, is known in particular to be intensified by urbanization and globalization. Zika is primarily spread by *Aedes aegypti* mosquitoes, and can also be transmitted through sexual contact or blood transfusions. The basic reproduction number ($R_0$, a measure of transmissibility) of Zika virus has been estimated to be between 1.4 and 6.6.

In 2015, news reports drew attention to the rapid spread of Zika in Latin America and the Caribbean. At that time, the Pan American Health Organization published a list of countries and territories that experienced "local Zika virus transmission" comprising Barbados, Bolivia, Brazil, Colombia, the Dominican Republic, Ecuador, El Salvador, French Guiana, Guadeloupe, Guatemala, Guyana, Haiti, Honduras, Martinique, Mexico, Panama, Paraguay, Puerto Rico, Saint Martin, Suriname, and Venezuela. By August 2016, more than 50 countries had experienced active (local) transmission of Zika virus.

Zika is primarily spread by the female *Aedes aegypti* mosquito, which is active mostly in the daytime, although researchers have found the virus in common Culex house mosquitoes as well. The mosquitos must feed on blood in order to lay eggs. The virus has also been isolated from a number of arboreal mosquito species in the *Aedes* genus, such as *A. africanus, A. apicoargenteus, A. furcifer, A. hensilli, A. luteocephalus* and *A. vittatus*, with an extrinsic incubation period in mosquitoes of about 10 days.

The true extent of the vectors is still unknown. Zika has been detected in many more species of *Aedes*, along with *Anopheles coustani, Mansonia uniformis*, and *Culex perfuscus*, although this alone does not incriminate them as a vector.

Transmission by *A. albopictus*, the tiger mosquito, was reported from a 2007 urban outbreak in Gabon where it had newly invaded the country and become the primary vector for the concomitant chikungunya and dengue virus outbreaks. There is concern for autochthonous infections in urban areas of European countries infested by *A. albopictus* because the first two cases of laboratory-confirmed Zika infections imported into Italy were reported from viremic travelers returning from French Polynesia.

The potential societal risk of Zika can be delimited by the distribution of the mosquito species that transmit it. The global distribution of the most cited carrier of Zika, *A. aegypti*, is expanding due to global trade and travel. *A. aegypti* distribution is now the most extensive ever recorded—across all continents including North America and even the European periphery (Madeira, the Netherlands, and the northeastern Black Sea coast). A mosquito population capable of carrying Zika has been found in a Capitol Hill neighborhood of Washington, D.C., and genetic evidence suggests they survived at least four consecutive winters in the region. The study authors conclude that mosquitos are adapting for persistence in a northern climate. The Zika virus appears to be contagious via mosquitoes for around a week after infection. The virus is thought to be infectious for a longer period of time after infection (at least 2 weeks) when transmitted via semen.

Research into its ecological niche suggests that Zika may be influenced to a greater degree by changes in precipitation and temperature than Dengue, making it more likely to be confined to tropical areas. However, rising global temperatures would allow for the disease vector to expand their range further north, allowing Zika to follow.

Zika can be transmitted from men and women to their sexual partners. As of April 2016 sexual transmission of Zika has been documented in six countries—Argentina, Chile, France, Italy, New Zealand and the United States—during the 2015 outbreak.

In 2014, Zika capable of growth in lab culture was found in the semen of a man at least two weeks (and possibly up to 10 weeks) after he fell ill with Zika fever. In 2011 a study found that a U.S. biologist who had been bitten many times while studying mosquitoes in Senegal developed symptoms six days after returning home in August 2008, but not before having unprotected intercourse with his wife, who had not been outside the U.S. since 2008. Both husband and wife were confirmed to have Zika antibodies, raising awareness of the possibility of sexual transmission. In early February 2016, the Dallas County Health and Human Services department reported that a man from Texas who had not travelled abroad had been infected after his male monogamous sexual partner had anal penetrative sex with him one day before and one day after onset of symptoms. As of February 2016, fourteen additional cases of possible sexual transmission have been under investigation, but it remained unknown whether women can transmit Zika to their sexual partners. At that time, the understanding of the "incidence and duration of shedding in the male genitourinary tract [was] limited to one case report." Therefore, the CDC interim guideline recommended against testing men for purposes of assessing the risk of sexual transmission.

In March 2016, the CDC updated its recommendations about length of precautions for couples, and advised that heterosexual couples with men who have confirmed Zika fever or symptoms of Zika should consider using condoms or not having penetrative sex (i.e., vaginal intercourse, anal intercourse, or fellatio) for at least 6 months after symptoms begin. This includes men who live in—and men who traveled to—areas with Zika. Couples with men who traveled to an area with Zika, but did not develop symptoms of Zika, should consider using condoms or not having sex for at least 8 weeks after their return in order to minimize risk. Couples with men who live in an area with Zika, but have not developed symptoms, might consider using condoms or not having sex while there is active Zika transmission in the area. The Zika virus can spread from an infected mother to her fetus during pregnancy or at delivery.

As of April 2016, two cases of Zika transmission through blood transfusions have been reported globally, both from Brazil, after which the US Food and Drug Administration (FDA) recommended screening blood donors and deferring high-risk donors for 4 weeks. A potential risk had been suspected based on a blood-donor screening study during the French Polynesian Zika outbreak, in which 2.8% (42) of donors from November 2013 and February 2014 tested positive for Zika RNA and were all asymptomatic at the time of blood donation. Eleven of the positive donors reported symptoms of Zika fever after their donation, but only three of 34 samples grew in culture.

Zika virus replicates in the mosquito's midgut epithelial cells and then its salivary gland cells. After 5-10 days, the virus can be found in the mosquito's saliva. If the mosquito's saliva is inoculated into human skin, the virus can infect epidermal keratinocytes, skin fibroblasts in the skin and the Langerhans cells. The pathogenesis of the virus is hypothesized to continue with a spread to lymph nodes and the bloodstream. Flaviviruses generally replicate in the cytoplasm, but Zika antigens have been found in infected cell nuclei.

Zika fever (also known as Zika virus disease) is an illness caused by the Zika virus. Most cases have no symptoms, but when present they are usually mild and can resemble dengue fever. Symptoms may include fever, red eyes, joint pain, headache, and a maculopapular rash. Symptoms generally last less than seven days. It has not caused any reported deaths during the initial infection. Infection during pregnancy causes microcephaly and other brain malformations in some babies. Infection in adults has been linked to Guillain-Barré syndrome (GBS). Diagnosis is by testing the blood, urine, or saliva for the presence of Zika virus RNA when the person is sick.

Prevention involves decreasing mosquito bites in areas where the disease occurs, and proper use of condoms. Efforts to prevent bites include the use of insect repellent, covering much of the body with clothing, mosquito nets, and getting rid of standing water where mosquitoes reproduce. There is no effective vaccine. Health officials recommended that women in areas affected by the 2015-16 Zika outbreak consider putting off pregnancy and that pregnant women not travel to these areas. While there is no specific treatment, paracetamol (acetaminophen) and rest may help with the symptoms. Admission to hospital is rarely necessary.

Effective vaccines have existed for several viruses of the flaviviridae family, namely yellow fever vaccine, Japanese encephalitis vaccine, and tick-borne encephalitis vaccine, since the 1930s, and dengue fever vaccine since the mid-2010s. World Health Organization (WHO) experts have suggested that the priority should be to develop inactivated vaccines and other non-live vaccines, which are safe to use in pregnant women and those of childbearing age.

As of March 2016, eighteen companies and institutions internationally were developing vaccines against Zika but a vaccine was unlikely to be widely available for about ten years. In June 2016 the FDA granted the first approval for a human clinical trial for a Zika vaccine.

The virus was first isolated in April 1947 from a rhesus macaque monkey that had been placed in a cage in the Zika Forest of Uganda, near Lake Victoria, by the scientists of the Yellow Fever Research Institute. A second isolation from the mosquito *A. africanus* followed at the same site in January 1948. When the monkey developed a fever, researchers isolated from its serum a "filterable transmissible agent" that was named Zika in 1948.

Zika had been known to infect humans from the results of serological surveys in Uganda and Nigeria, published in 1952: Among 84 people of all ages, 50 individuals had antibodies to Zika, and all above 40 years of age were immune. A 1952 research study conducted in India had shown a "significant number" of Indians tested for Zika had exhibited an immune response to the virus, suggesting it had long been widespread within human populations.

It was not until 1954 that the isolation of Zika from a human was published. This came as part of a 1952 outbreak investigation of jaundice suspected to be yellow fever. It was found in the blood of a 10-year-old Nigerian female with low-grade fever, headache, and evidence of malaria, but no jaundice, who recovered within three days. Blood was injected into the brain of laboratory mice, followed by up to 15 mice passages. The virus from mouse brains was then tested in neutralization tests using rhesus monkey sera specifically immune to Zika. In contrast, no virus was isolated from the blood of two infected adults with fever, jaundice, cough, diffuse joint pains in one and fever, headache, pain behind the eyes and in the joints. Infection was proven by a rise in Zika-specific serum antibodies.

From 1951 through 1983, evidence of human infection with Zika was reported from other African countries, such as the Central African Republic, Egypt, Gabon, Sierra Leone, Tanzania, and Uganda, as well as in parts of Asia including India, Indonesia, Malaysia, the Philippines, Thailand, Vietnam and Pakistan. From its discovery until 2007, there were only 14 confirmed human cases of Zika infection from Africa and Southeast Asia.

In April 2007, the first outbreak outside of Africa and Asia occurred on the island of Yap in the Federated States of Micronesia, characterized by rash, conjunctivitis, and arthralgia, which was initially thought to be dengue, chikungunya, or Ross River disease. Serum samples from patients in the acute phase of illness contained RNA of Zika. There were 49 confirmed cases, 59 unconfirmed cases, no hospitalizations, and no deaths. Between 2013 and 2014, further epidemics occurred in French Polynesia, Easter Island, the Cook Islands, and New Caledonia. On 22 Mar. 2016 Reuters reported that Zika was isolated from a 2014 blood sample of an elderly man in Chittagong in Bangladesh as part of a retrospective study.

As of early 2016, a widespread outbreak of Zika was ongoing, primarily in the Americas. The outbreak began in April 2015 in Brazil, and has spread to other countries in South America, Central America, North America, and the Caribbean. The Zika virus reached Singapore and Malaysia in August 2016. In January 2016, the WHO said the virus was likely to spread throughout most of the Americas by the end of the year; and in February 2016, the WHO declared the cluster of microcephaly and Guillain-Barré syndrome cases reported in Brazil—strongly suspected to be associated with the Zika outbreak—a Public Health Emergency of International Concern. It is estimated that 1.5 million people have been infected by Zika in Brazil, with over 3,500 cases of microcephaly reported between October 2015 and January 2016.

A number of countries have issued travel warnings, and the outbreak is expected to significantly impact the tourism industry. Several countries have taken the unusual step of advising their citizens to delay pregnancy until more is known about the virus and its impact on fetal development. With the 2016 Summer Olympic Games hosted in Rio de Janeiro, health officials worldwide have voiced concerns over a potential crisis, both in Brazil and when international athletes and tourists, who may be unknowingly infected, return home and possibly spread the virus. Some researchers speculate that only one or two tourists may be infected during the three week period, or approximately 3.2 infections per 100,000 tourists.

II. Monoclonal Antibodies and Production Thereof

A. General Methods

It will be understood that monoclonal antibodies binding to Zika virus will have several applications. These include the production of diagnostic kits for use in detecting and diagnosing Zika virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDR's from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (0 the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Beltramello et al. (2010) previously reported the modification of neutralizing mAbs, due to their tendency to enhance DV infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four DENV serotypes. LALA variants retained the same neutralizing activity as unmodified mAbs, but were completely devoid of enhancing activity. LALA mutations of this nature are therefore contemplated in the context of the presently disclosed antibodies.

Fc variants mutagenesis are described in patent applications WO2010106180 and WO2012175751. These include M252Y/S254T/T256E (Fc-YTE), as well as M428L/N434S (Fc-LS).

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage diplay and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Active/Passive Immunization and Treatment/Prevention of Zika virus Infection

A. Formulation and Administration

The present disclosure provides pharmaceutical compositions comprising anti-Zika virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those disclosed are produced in vivo in a subject at risk of Zika virus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$ indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting Zika virus and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Other immunodections methods include specific assays for determining the presence of Zika virus in a subject. A wide variety of assay formats are contemplated, but specifically those that would be used to detect Zika virus in a fluid obtained from a subject, such as saliva, blood, plasma, sputum, semen or urine. In particular, semen has been demonstrated as a viable sample for detecting Zika virus (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may advantageously for formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Zika virus antibodies directed to specific parasite epitopes in samples also is provided. The steps of various useful immunodetection methods have been described in the scientific literature, such as, e.g., Doolittle and Ben-Zeev (1999), Gulbis and Galand 0993), De Jager et al. (1993), and Nakamura et al. (1987). In general, the immunobinding methods include obtaining a sample suspected of containing Zika virus, and contacting the sample with a first antibody in accordance with the present disclosure, as the case may be, under conditions effective to allow the formation of immunocomplexes.

These methods include methods for purifying Zika virus or related antigens from a sample. The antibody will preferably be linked to a solid support, such as in the form of a column matrix, and the sample suspected of containing the Zika virus or antigenic component will be applied to the immobilized antibody. The unwanted components will be washed from the column, leaving the Zika virus antigen immunocomplexed to the immobilized antibody, which is then collected by removing the organism or antigen from the column.

The immunobinding methods also include methods for detecting and quantifying the amount of Zika virus or related components in a sample and the detection and quantification of any immune complexes formed during the binding process. Here, one would obtain a sample suspected of containing Zika virus or its antigens, and contact the sample with an antibody that binds Zika virus or components thereof, followed by detecting and quantifying the amount of immune complexes formed under the specific conditions. In terms of antigen detection, the biological sample analyzed may be any sample that is suspected of containing Zika virus or Zika virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Zika virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Zika virus or Zika virus antigen is added to the wells. After binding and washing to remove non-specifically bound immune complexes, the bound antigen may be detected. Detection may be achieved by the addition of another anti-Zika virus antibody that is linked to a detectable label. This type of ELISA is a simple "sandwich ELISA." Detection may also be achieved by the addition of a second anti-Zika virus antibody, followed by the addition of a third antibody that has binding affinity for the second antibody, with the third antibody being linked to a detectable label.

In another exemplary ELISA, the samples suspected of containing the Zika virus or Zika virus antigen are immobilized onto the well surface and then contacted with the anti-Zika virus antibodies of the disclosure. After binding and washing to remove non-specifically bound immune complexes, the bound anti-Zika virus antibodies are detected. Where the initial anti-Zika virus antibodies are linked to a detectable label, the immune complexes may be detected directly. Again, the immune complexes may be detected using a second antibody that has binding affinity for the first anti-Zika virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of Zika virus antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled Zika virus monoclonal antibodies to determine the amount of Zika virus antibodies in a sample. The basic format would include contacting a known amount of Zika virus monoclonal antibody (linked to a detectable label) with Zika virus antigen or particle. The Zika virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many lab based applications exist that are supported by reading equipment. Typically, these tests are used as low resources medical diagnostics, either for home testing, point of care testing, or laboratory use. A widely spread and well known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container.

Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect Zika virus or Zika virus antigens, the antibodies may be included in the kit. The immunodetection kits will thus comprise, in suitable container means, a first antibody that binds to Zika virus or Zika virus antigen, and optionally an immunodetection reagent.

In certain embodiments, the Zika virus antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the Zika virus or Zika virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Material and Methods

Research subjects. The inventors studied eight subjects in the U.S. with prior or recent ZIKV infection (Table 5). The studies were approved by the Institutional Review Board of Vanderbilt University Medical Center; samples were obtained after informed consent was obtained by the Vanderbilt Clinical Trials Center. Two subjects (972 and 973) were infected with an African lineage strain in 2008 (one subject while working in Senegal, the second acquired the infection by sexual transmission from the first, as previously reported (Foy et al., 2011). The other six subjects were infected during the current outbreak of an Asian lineage strain, following exposure in Brazil, Mexico, or Haiti.

Generation and quantification of human B cell lines secreting ZIKV E protein specific antibodies. Peripheral blood mononuclear cells (PBMCs) from heparinized blood were isolated with Ficoll-Histopaque by density gradient centrifugation. The cells either were used immediately or cryopreserved in the vapor phase of liquid nitrogen until use. Ten million PBMCs were cultured in 384-well plates (Nunc) using culture medium (ClonaCell-HY Medium A, StemCell Technologies) supplemented with 8 μg/ml of the TLR agonist CpG (phosphorothioate-modified oligodeoxynucleotide ZOEZOEZZZZZOEEZOEZZZT, Invitrogen), 3 μg/ml of Chk2 inhibitor (Sigma), 1 μg/ml of cyclosporine A (Sigma), and clarified supernatants from cultures of B95.8 cells (ATCC) containing Epstein-Barr virus (EBV). After 7 days, cells from each 384-well culture plate were expanded into four 96-well culture plates (Falcon) using ClonaCell-HY Medium A containing 8 μg/ml of CpG, 3 μg/ml of Chk2 inhibitor, and $10^7$ irradiated heterologous human PBMCs (Nashville Red Cross) and cultured for an additional 4 days. Supernatants were screened in ELISA (described below) for reactivity with various ZIKV E proteins, which are described below.

The minimal frequency of ZIKV E-reactive B cells was estimated based on the number of wells with E protein-reactive supernatants compared with the total number of lymphoblastoid cell line colonies in the transformation plates [calculation: E-reactive B cell frequency=(number of wells with E-reactive supernatants) divided by [number of LCL colonies in the plate)×100].

Protein expression and purification. The ectodomains of ZIKV E (H/PF/2013; GenBank Accession KJ776791) and the fusion-loop mutant E-FLM (containing four mutations: T76A, Q77G, W101R, L107R) were expressed transiently in Expi293F cells and purified as described previously (Zhao et al., 2016). ZIKV DIII (residues 299-407 of strain H/PF/2013), WNV-DIII (residues 296-405 of strain New York 1999) and DENV2-DIII (residues 299-410 of strain 16681) were expressed in BL21 (DE3) as inclusion bodies and refolded in vitro (Nelson et al., 2014). Briefly, inclusion bodies were denatured and refolded by gradual dilution into a refolding buffer (400 mM L-arginine, 100 mM Tris [pH 8.3], 2 mM EDTA, 5 and 0.5 mM reduced and oxidized glutathione) at 4° C. Refolded proteins were purified by size-exclusion chromatography using a Superdex 75, 16/60 (GE Healthcare).

Generation of human hybridomas. Cells from wells with transformed B cells containing supernatants that exhibited reactivity to ZIKV E protein were fused with HMMA2.5 myeloma cells (kind gift from L. Cavacini) using an established electrofusion technique (Yu et al., 2008). After fusion, hybridomas were suspended in a selection medium containing 100 μM hypoxanthine, 0.4 μM aminopterin, 16 μM thymidine (HAT Media Supplement, Sigma), and 7 μg/ml ouabain (Sigma) and cultured in 384-well plates for 18 days before screening hybridomas for antibody production by ELISA. After fusion with HMMA2.5 myeloma cells, hybridomas producing ZIKV E-specific antibodies were cloned biologically by single-cell fluorescence-activated cell sorting. Hybridomas were expanded in post-fusion medium (ClonaCell-HY Medium E, STEMCELL Technologies) until 50% confluent in 75-cm$^2$ flasks (Corning).

For antibody production, cells from one 75-cm$^2$ flask were collected with a cell scraper and expanded to four 225-cm$^2$ flasks (Corning) in serum-free medium (Hybridoma-SFM, Life Technologies). After 21 days, supernatants were clarified by centrifugation and filtered using 0.45-μm pore size filter devices. HiTrap Protein G or HiTrap MabSelectSure columns (GE Healthcare Life Sciences) were used to purify antibodies from filtered supernatants.

Sequence analysis of antibody variable region genes. Total cellular RNA was extracted from pelleted cells from hybridoma clones, and an RT-PCR reaction was performed using mixtures of primers designed to amplify all heavy-chain or light-chain antibody variable regions (Nelson et al., 2014). The generated PCR products were purified using AMPure XP magnetic beads (Beckman Coulter) and sequenced directly using an ABI3700 automated DNA sequencer. The variable region sequences of the heavy and light chains were analyzed using the IMGT/V-Quest program (Brochet et al., 2008; Guidicell & Lefranc, 2011).

ELISA and half-maximal effective concentration ($EC_{50}$) binding analysis. Wells of microtiter plates were coated with purified, recombinant ectodomain of ZIKV E, DIII, DIII LRM (DIII containing A310E and T335K mutations in the lateral ridge of DIII) or DIII of related flaviviruses DENV2 or WNV and incubated at 4° C. overnight. In ELISA studies with purified mAbs, the inventors used recombinant ZIKV E protein ectodomain with $His_6$ tag produced in Sf9 insect cells (Meridian Life Sciences R01635). Plates were blocked with 5% skim milk in PBS-T for 1 hr. B cell culture supernatants or purified antibodies were added to the wells and incubated for 1 hr at ambient temperature. The bound antibodies were detected using goat anti-human IgG (γ-specific) conjugated with alkaline phosphatase (Southern Biotech) and pNPP disodium salt hexahydrate substrate (Sigma). In ELISAs that assessed binding of mAbs to DIII and DIII LRM, the inventors used previously described murine mAbs ZV-2 and ZV-54 (Zhao et al., 2016) as controls. A goat anti-mouse IgG conjugated with alkaline phosphatase (Southern Biotech) was used for detection of these antibodies. Color development was monitored at 405 nm in a spectrophotometer (Biotek). For determining half-maximal effective concentration binding ($EC_{50}$), microtiter plates were coated with ZIKV E or E-FLM that eliminated interaction of fusion-loop specific antibodies. Purified antibodies were diluted serially and applied to the plates. Bound antibodies were detected as above. A non-linear regression analysis was performed on the resulting curves using Prism (GraphPad) to calculate $EC_{50}$ values.

ELISA for detection of human antibodies in murine tissues. Fetal head and placental tissues were collected at E13.5 from groups treated with ZIKV-117 or PBS (as a negative control), homogenized in PBS (250 μl) and stored at −20° C. ELISA plates were coated with ZIKV E protein, and thawed, clarified tissue homogenates were applied undiluted in triplicate. Bound antibodies were detected using goat anti-human IgG (Fc-specific) antibody conjugated with alkaline phosphatase. The quantity of antibody was determined by comparison with a standard curve constructed using purified ZIKV-117 in a dilution series.

Biolayer interferometry competition binding assay. $His_6$-tagged ZIKV E protein was immobilized on anti-His coated biosensor tips (Pall) for 2 min on an Octet Red biosensor instrument. After measuring the baseline signal in kinetics buffer (PBS, 0.01% BSA, and 0.002% Tween 20) for 1 min, biosensor tips were immersed into the wells containing first antibody at a concentration of 10 μg/ml for 7 min. Biosensors then were immersed into wells containing a second mAb at a concentration of 10 μg/ml for 7 min. The signal obtained for binding of the second antibody in the presence of the first antibody was expressed as a percent of the uncompeted binding of the second antibody that was derived independently. The antibodies were considered competing if the presence of first antibody reduced the signal of the second antibody to less than 30% of its maximal binding and non-competing if the signal was greater than 70%. A level of 30-70% was considered intermediate competition.

Shotgun mutagenesis epitope mapping. Epitope mapping was performed by shotgun mutagenesis essentially as described previously (Davidson & Doranz, 2014. A ZIKV prM/E protein expression construct (strain ZikaSPH2015) was subjected to high-throughput alanine scanning mutagenesis to generate a comprehensive mutation library. Each residue within prM/E was changed to alanine, with alanine codons mutated to serine. In total, 672 ZIKV prM/E mutants were generated (100% coverage), sequence confirmed, and arrayed into 384-well plates. Each ZIKV prM/E mutant was transfected into HEK-293T cells and allowed to express for 22 h. Cells were fixed in 4% (v/v) paraformaldehyde (Electron Microscopy Sciences), and permeabilized with 0.1% (w/v) saponin (Sigma-Aldrich) in PBS plus calcium and magnesium (PBS++). Cells were incubated with purified mAbs diluted in PBS++, 10% normal goat serum (NGS) (Sigma), and 0.1% saponin. Primary antibody screening concentrations were determined using an independent immunofluorescence titration curve against WT ZIKV prM/E to ensure that signals were within the linear range of detection. Antibodies were detected using 3.75 μg/ml of AlexaFluor488-conjugated secondary antibody (Jackson ImmunoResearch Laboratories) in 10% NGS/0.1% saponin. Cells were washed three times with PBS++/0.1% saponin followed by two washes in PBS. Mean cellular fluorescence was detected using a high-throughput flow cytometer (HTFC, Intellicyt). Antibody reactivity against each mutant prM/E clone was calculated relative to WT prM/E protein reactivity by subtracting the signal from mock-transfected controls and normalizing to the signal from WT prM/E-transfected controls. Mutations within clones were identified as critical to the mAb epitope if they did not support reactivity of the test MAb, but supported reactivity of other ZIKV antibodies. This counter-screen strategy facilitates the exclusion of prM/E mutants that are locally misfolded or have an expression defect.

Vertebrate animal studies ethics statement. This study was carried out in accordance with the recommendations in the Guide for the Care and Use of Laboratory Animals of the National Institutes of Health. The protocols were approved by the Institutional Animal Care and Use Committee at the Washington University School of Medicine (Assurance number A3381-01). Inoculations were performed under anesthesia induced and maintained with ketamine hydrochloride and xylazine, and all efforts were made to minimize animal suffering.

Viruses and cells. ZIKV strain H/PF/2013 (French Polynesia, 2013) was obtained from X. de Lamballerie (Aix Marseille Université). ZIKV Brazil Paraiba 2015 was provided by S. Whitehead (Bethesda) and originally obtained from P.F.C. Vasconcelos (Instituto Evandro Cargas). ZIKV MR 766 (Uganda, 1947), Malaysia P6740 (1966), and Dakar 41519 (Senegal, 1982) were provided by the World Reference Center or Emerging Viruses and Arboviruses (R. Tesh, University of Texas Medical Branch). Nicaraguan DENV strains (DENV-1 1254-4, DENV-2 172-08, DENV-3 N2845-09, and DENV-4 N703-99) were provided generously by E. Harris (University of California, Berkeley). Virus stocks were propagated in C6/36 *Aedes albopictus* cells (DENV) or Vero cells (ZIKV). ZIKV Dakar 41519 (ZIKV-Dakar) was passaged twice in vivo in $Rag1^{-/-}$ mice (M. Gorman and M. Diamond, unpublished data) to create a mouse-adapted strain. Virus stocks were titrated by focus-forming assay (FFA) on Vero cells.

Neutralization assays. Serial dilutions of mAbs were incubated with $10^2$ FFU of different ZIKV strains (MR 766, Dakar 41519, Malaysia P6740, H/PF/2013, or Brazil Paraiba 2015) for 1 hr at 37° C. The mAb-virus complexes were added to Vero cell monolayers in 96-well plates for 90 min at 37° C. Subsequently, cells were overlaid with 1% (w/v) methylcellulose in MEM supplemented with 4% heat-inactivated FBS. Plates were fixed 40 h later with 1% PFA in PBS for 1 hr at room temperature. The plates were incubated sequentially with 500 ng/ml mouse anti-ZIKV (ZV-16, E. Fernandez and M. Diamond, unpublished) and HRP-conjugated goat anti-mouse IgG in PBS supplemented with 0.1% (w/v) saponin (Sigma) and 0.1% BSA. ZIKV-infected cell foci were visualized using TrueBlue peroxidase substrate (KPL) and quantitated on an ImmunoSpot 5.0.37 macroanalyzer (Cellular Technologies).

MAb binding to ZIKV- or DENV-infected cells. C6/36 *Aedes albopictus* cells were inoculated with a MOI 0.01 of ZIKV (H/PF/2013) or different DENV serotypes (Nicaraguan strains DENV-1 1254-4, DENV-2 172-08, DENV-3 N2845-09, DENV-4 N703-99). At 120 hr post infection, cells were fixed with 4% PFA diluted in PBS for 20 min at room temperature and permeabilized with HBSS supplemented with 10 mM HEPES, 0.1% saponin and 0.025% $NaN_3$ for 10 min at room temperature. Fifty-thousand cells were transferred to U-bottom plates and incubated for 30 min at 4° C. with 5 μg/ml of anti-ZIKV human mAbs or negative (hCHK-152)[12]; or positive (hE60) (Williams et al., 2013) isotype controls. After washing, cells were incubated with Alexa Fluor 647-conjugated goat anti-human IgG (Invitrogen) at 1:500, fixed in 1% PFA in PBS, processed on MACSQuant Analyzed (Miltenyi Biotec), and analyzed using FlowJo software (Tree Star).

Recombinant antibody expression and purification. Total RNA was extracted from hybridoma cells and genes encoding the VH and VL domains were amplified in RT-PCR using IgExp primers (Thornburg et al., 2016). The PCR products were directly cloned into antibody expression vectors containing the constant domains of WT gamma1 chain, LALA mutant (a leucine (L) to alanine (A) substitution at positions 234 and 235) gamma1 chain for the VH domains, and WT kappa chain for the VL domain in an isothermal amplification reaction (Gibson reaction) (Gibson et al., 2009). Plasmids encoding the heavy and light chain were transfected into 293F cells and full length recombinant IgG was secreted into transfected cell supernatants. Supernatants were collected and IgG purified using Protein G chromatography and eluted into PBS. The functional abrogation of the binding of the LALA variant IgG was confirmed in an ELISA binding assay with recombinant human FcγRI. The binding of ZIKV-117 WT or LALA antibody to FcγRI was evaluated, in comparison with the binding pattern of control antibodies (human mAb CKV063 (Fong et al., 2014) LALA mutated IgG).

Adult mouse lethal protection experiments. C57BL/6J male mice (4 to 5 week-old, Jackson Laboratories) were inoculated with $10^3$ FFU of mouse-adapted ZIKV Dakar by subcutaneous route in the footpad. One-day prior to infection, mice were treated with 2 mg anti-Ifnar1 mAb (MAR1-5A3, Leinco Technologies) by intraperitoneal injection. ZIKV-specific human mAb (ZIKV-117) or an isotype control (hCHK-152) was administered as a single dose at day +1 (100 μg) or day +5 (250 μg) after infection via an intraperitoneal route. Animals were monitored for 21 days.

Pregnant mouse protection experiments. WT C57BL/6J mice were bred in a specific pathogen-free facility at Washington University School of Medicine. WT dams, prophylaxis studies. WT female and male mice were mated; at embryonic days E5.5, dams were treated with a single 250 μg dose of ZIKV mAb or isotype control by intraperitoneal injection as well as a 1 mg injection of anti-Ifnar1 (MAR1-5A3). At E6.5, mice were inoculated with $10^3$ FFU of mouse-adapted ZIKV Dakar 41519 by subcutaneous injection in the footpad. At E7.5, dams received a second 1 mg dose of anti-Ifnar1 via an intraperitoneal route. WT dams, therapy. WT female and male mice were mated; at embryonic days E5.5, dams were treated with a 1 mg injection of anti-Ifnar1 (MAR1-5A3). At E6.5, mice were inoculated with mouse-adapted $10^3$ FFU of ZIKV Dakar 41519 by subcutaneous injection in the footpad. At E7.5, dams received a second 1 mg dose of anti-Ifnar1 as well as a single 250 μg dose of ZIKV mAb or isotype control via an intraperitoneal route. All animals were sacrificed at E13.5, and placentas, fetuses and maternal tissues were harvested. Fetus size was measured as the crown-rump length×occipito-frontal diameter of the head.

Measurement of viral burden. ZIKV-infected tissues were weighed and homogenized with stainless steel beads in a Bullet Blender instrument (Next Advance) in 200 μL of PBS. Samples were clarified by centrifugation (2,000×g for 10 min). All homogenized tissues from infected animals were stored at −20° C. Tissue samples and serum from ZIKV-infected mice were extracted with RNeasy 96 Kit (tissues) or Viral RNA Mini Kit (serum) (Qiagen). ZIKV RNA levels were determined by TaqMan one-step quantitative reverse transcriptase PCR (qRT-PCR) on an ABI7500

Fast Instrument using published primers and conditions (Lanciotti et al., 2008). Viral burden was expressed on a $\log_{10}$ scale as viral RNA equivalents per g or ml after comparison with a standard curve produced using serial 10-fold dilutions of ZIKV RNA.

Viral RNA in situ hybridization (ISH). RNA ISH was performed with RNAscope 2.5 (Advanced Cell Diagnostics) according to the manufacturer's instructions. PFA-fixed paraffin embedded placental sections were deparaffinized by incubation for 60 min at 60° C. Endogenous peroxidases were quenched with $H_2O_2$ for 10 min at room temperature. Slides were boiled for 15 min in RNAscope Target Retrieval Reagents and incubated for 30 min in RNAscope Protease Plus before probe hybridization. The probe targeting ZIKV RNA was designed and synthesized by Advanced Cell Diagnostics (catalog no. 467771). Negative (targeting bacterial gene dapB) control probes were also obtained from Advanced Cell Diagnostics (catalog no. 310043). Tissues were counterstained with Gill's hematoxylin and visualized with standard bright-field microscopy.

Histology and immunohistochemistry. Harvested placentas were fixed in 10% neutral buffered formalin at room temperature and embedded in paraffin. At least three placentas from different litters with the indicated treatments were sectioned and stained with hematoxylin and eosin to assess morphology. Surface area and thickness of placenta and different layers were measured using Image J software. For immunofluorescence staining on mouse placentas, deparaffinized tissues were blocked in blocking buffer (1% BSA, 0.3% Triton, 1×PBS) for 2 hr and incubated with anti-vimentin antibody (1:500, rabbit, Abcam ab92547). Secondary antibody conjugated with Alexa 488 (1:500 in PBS) was applied for 1 h at room temperature. Samples were counterstained with DAPI (4'6'-diamidino-2-phenilindole, 1:1,000 dilution).

Statistical analysis. All virological data were analyzed with GraphPad Prism software. Kaplan-Meier survival curves were analyzed by the log rank test, and viremia was compared using an ANOVA with a multiple comparisons test. A P value of $<0.05$ indicated statistically significant differences.

Example 2—Results

The inventors sought to isolate neutralizing human mAbs with broad specificity against all ZIKV strains. To do this, they initially tested the serological response of human survivors who had been infected with African or Asian lineage strain ZIKV in diverse geographic locations. Serum from each subject contained antibodies that reacted by ELISA with ZIKV E protein and neutralized infection of a contemporary Asian isolate (H/PF/2013) from French Polynesia (FIGS. 1A-B). The inventors studied the B cells of Subject 1001 in detail. The frequency of B cells secreting antibodies to ZIKV E protein in the peripheral blood of Subject 1001 was 0.61% (FIG. 1C), when a threshold for detection of binding [absorbance at 405 nm ($A_{405}$)] of 1.5 was used. They also tested the reactivity of antibodies with domain III (DIII) of the E protein from ZIKV, or the related dengue (DENV) or West Nile (WNV) viruses. Most of the ZIKV E reactive antibodies did not bind to DIII, and of those binding to DIII, most were ZIKV-specific (FIG. 1C). In a replicate of the assay performed with another aliquot of cells from the same subject (FIG. 1D), the frequency of ZIKV E-reactive B cell was 0.36%. Comparative binding to a WT ZIKV E or mutant (E-FLM) protein lacking the conserved fusion loop epitope in DII showed immunodominance (binding ~70% of mAbs) of the fusion loop.

Figure 5:
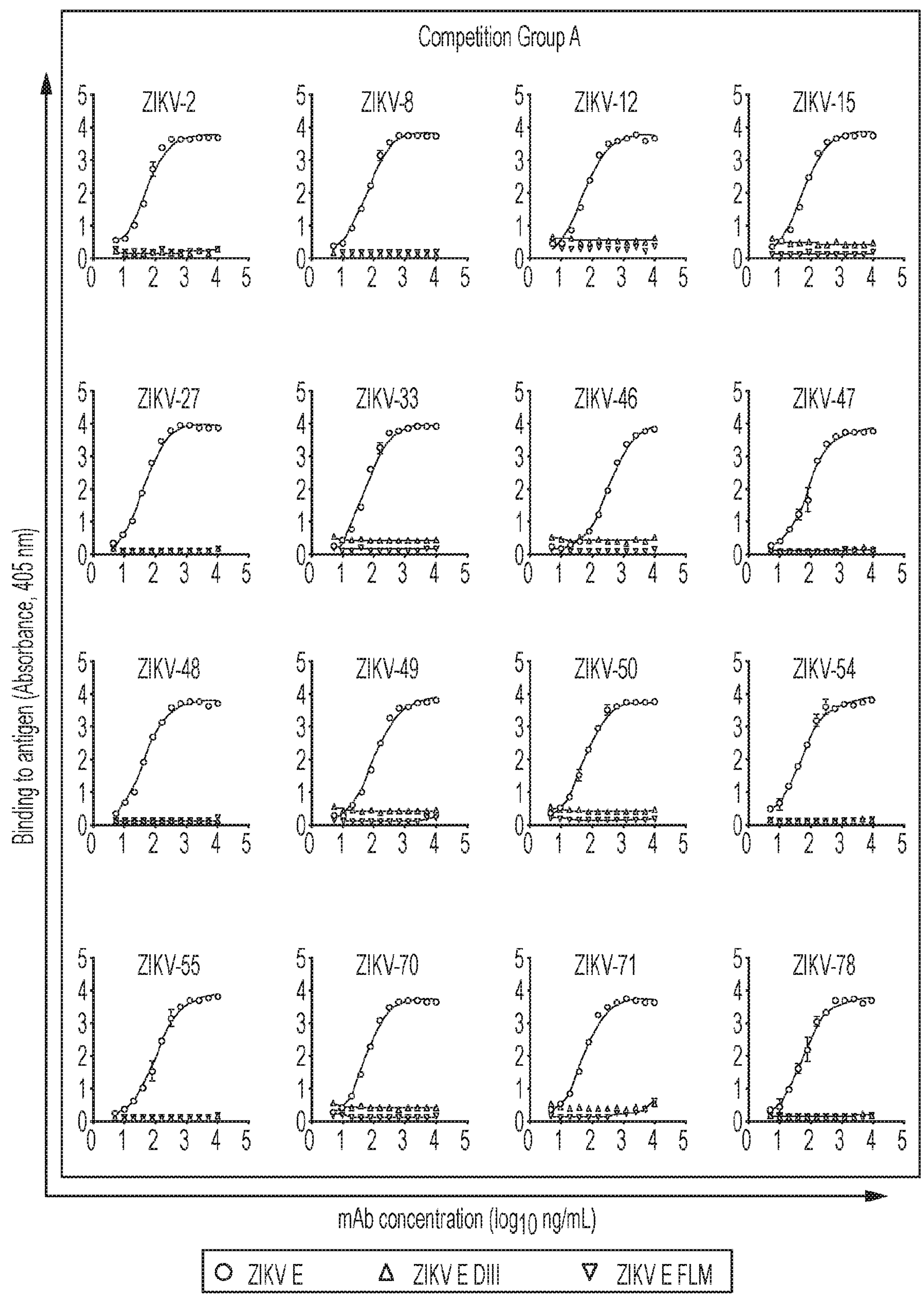
FIG. 5. Binding of human mAbs to Zika E protein, E DIII, or E fusion loop mutant (FLM). MAbs are organized by competition binding groups A to D.
Figure 5:
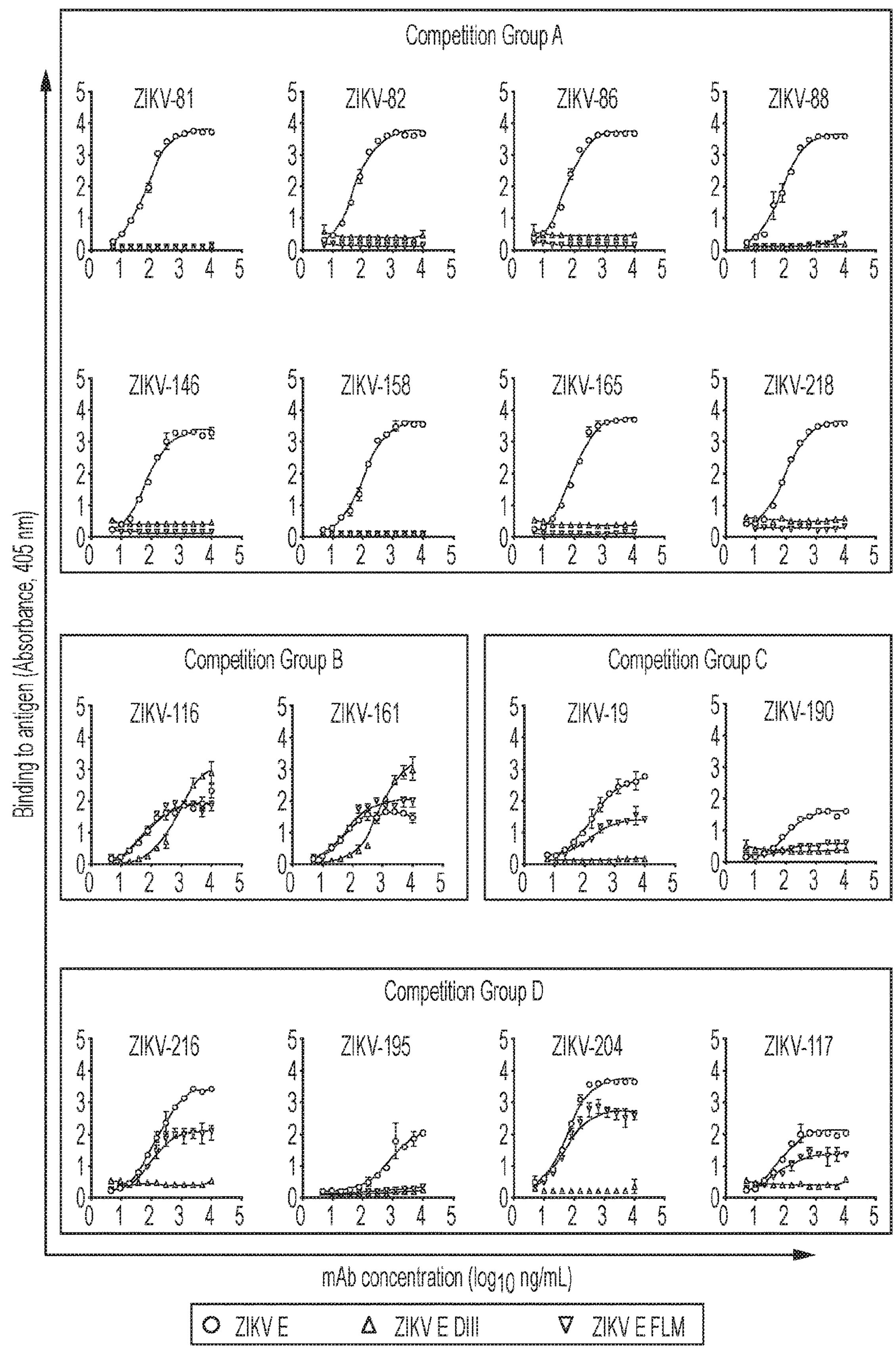

The inventors obtained 32 stable cloned hybridomas secreting antibodies that bound to ZIKV E protein from the cells of three donors (mAb ZIKV-195 from Subject 1011, mAbs ZIKV-204 and ZIKV-216 from Subject 973, and the remaining 29 mAbs from Subject 1001). All except one mAb belonged to IgG1 isotype, with an equal distribution of light chain isotypes (FIG. 2A). Sanger sequencing of cDNA of the antibody variable gene regions revealed that each mAb represented an independently derived clone. The inventors determined the half maximal effective concentration for binding ($EC_{50}$) to ZIKV E protein (FIG. 2A and FIG. 5); most of the mAbs bound to E protein at low concentrations, with $EC_{50}$ values generally below 100 ng/ml. Six of the 32 mAbs exhibited neutralizing activity, with $FRNT_{50}$ values in the range of 0.9 to 420 ng/ml. They next determined how many antigenic sites were recognized by members of the panel using quantitative competition binding to ZIKV E protein. The inventors identified four major competition groups (designated A, B, C or D). Antibodies belonging to the largest group, Group A with 24 members, were directed against the fusion loop in DII as determined from the disparate binding patterns to E, DIII, or to E-FLM (FIG. 5). This group of fusion loop specific mAbs had a single neutralizing clone (ZIKV-88), with moderate potency. Group B mAbs (ZIKV-116 and ZIKV-161) neutralized ZIKV infection and bound to E, DIII, and E-FLM. Group C mAbs (ZIKV-19 and ZIKV-190) bound to E and E-FLM weakly, but did not potently neutralize infection. Group D mAbs ZIKV-195 and ZIKV-216 neutralized with moderate potency and were similar in binding to both E and E-FLM. The most potently inhibitory Group D mAb, ZIKV-117, bound to both E and E-FLM weakly. One antibody (ZIKV-216) competed with members of both Groups C and D and neutralized with moderate potency.

The inventors mapped the epitopes of representative mAbs from each competition group using a complete shotgun mutagenesis library (Davidson & Doranz, 2014) of ZIKV prM/E (Brazil Paraiba 2015 strain) protein variants in which each residue was changed individually to alanine (FIG. 2B and FIGS. 6A-C). Loss-of-binding analysis confirmed that Group A mAbs bound to the fusion loop in DII, whereas Group B mAbs bound DIII. Group B mAb ZIKV-116 bound an epitope involving residue K394 in the lateral ridge of DIII, which was confirmed in an ELISA showing reduced binding to a DIII protein with mutations A310E and T335K in the DIII lateral ridge [DIII-LR] (Zhao et al., 2016). The non-neutralizing clones comprising Group C mAbs bound DII, and the group D neutralizing mAbs bound to a unique epitope in DII not described previously for the closely related DENV (Screaton et al., 2015). The position of the residues affecting binding of ZIKV-117 suggests that on the virion this mAb may bind DII across two distinct dimers (at the "dimer-dimer" interface, FIG. 2C). The inventors were unable to isolate virus neutralization escape mutant viruses for ZIKV-117 despite six passages in cell culture under mAb selection pressure.

Figure 7:
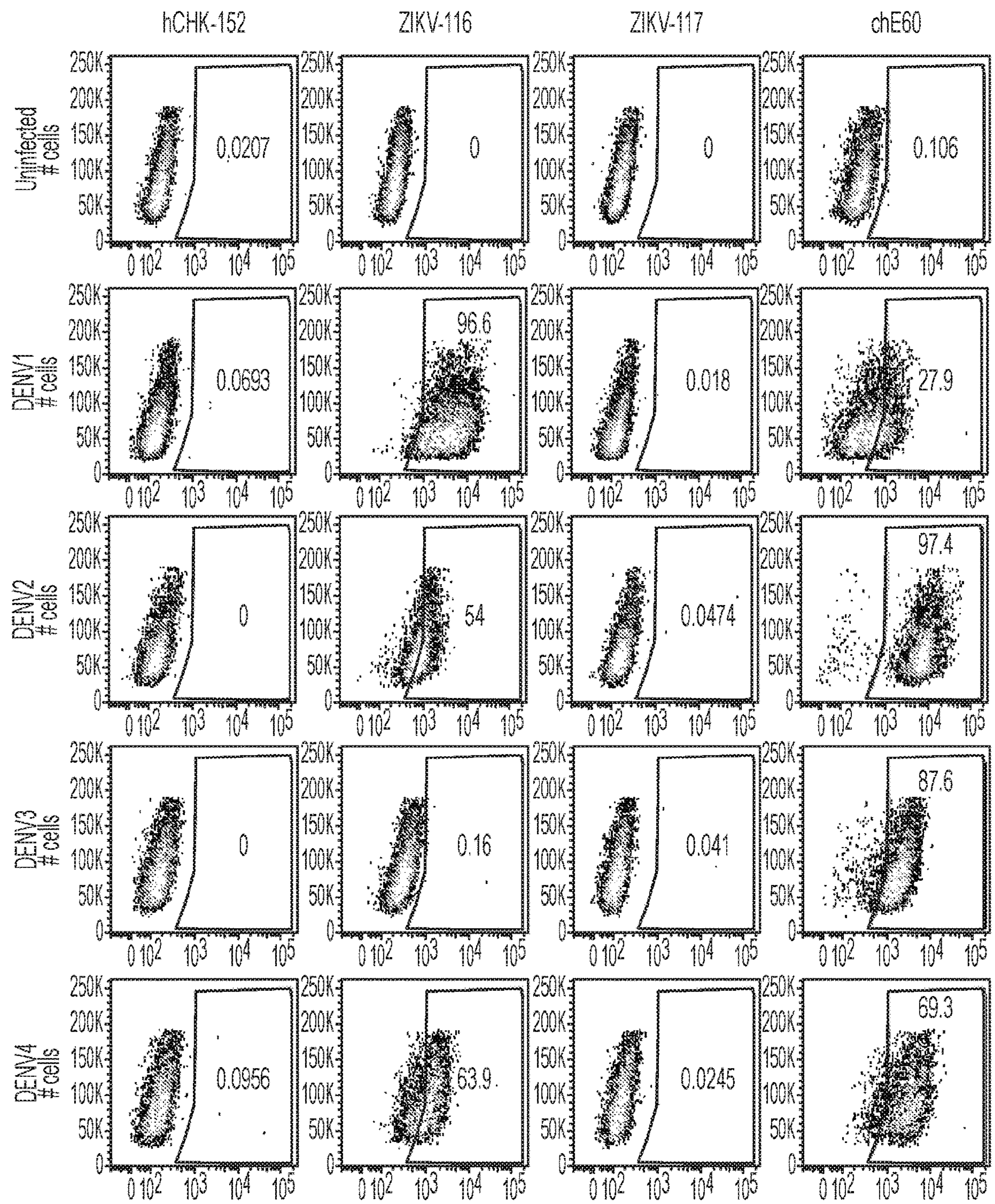
FIG. 7. Binding of human mAbs to permeabilized DENV-infected C6/36 cells. C6/36 cells were infected with DENV-1, DENV-2, DENV-3, DENV-4 or mock-infected. Cells were stained with the indicated anti-ZIKV mAbs, an isotype control (a humanized antibody to chikungunya virus; hCHK-152), or a positive control (a cross-reactive antibody to DENV; chimeric human E60 [chE60]) and processed by flow cytometry. The data are representative of two independent experiments. The numbers in the box indicate the fraction of cells that stained positively.

Of the 32 mAbs, six (ZIKV-88, ZIKV-116, ZIKV-161, ZIKV-195, ZIKV-216, and ZIKV-117) showed significant (<1 μg/ml) neutralizing activity in vitro against ZIKV French Polynesia strain H/PF/2013. The $FRNT_{50}$ values for the mAbs were as follows: Group A mAb ZIKV-88 (420 ng/ml), Group B mAbs ZIKV-116 (16 ng/ml) and ZIKV-161 (0.9 ng/ml), Group C/D mAb ZIKV-216 (16 ng/ml) and Group D mAbs ZIKV-195 (346 ng/ml) and ZIKV-117 (5 ng/ml). The inventors assessed whether Group B mAb ZIKV-116 and Group D mAb ZIKV-117 could inhibit diverse ZIKV strains encompassing the African, Asian, and American lineages. ZIKV-117 neutralized potently all ZIKV strains tested including two African (MR 766 and Dakar 41519), two Asian (Malaysia P6740 and H/PF/2013), and an American (Brazil Paraiba 2015) strain with $FRNT_{50}$ values of 5 to 25 ng/ml (FIGS. 2D-E). In comparison, ZIKV-116 inhibited four of the five strains efficiently, but lost activity against MR 766, the original African strain (FIGS. 2D-E). As recent studies have suggested that cross-reactive ZIKV-specific mAbs can enhance DENV infection in vivo (Stettler et al., 2016), the inventors tested whether these two ZIKV neutralizing mAbs could bind to DENV-infected C6/36 cells. ZIKV-117 showed a type-specific pattern of binding as it failed to stain permeabilized cells infected with DENV-1, DENV-2, DENV-3, or DENV-4 or bind to purified WNV E protein (FIG. 7 and data not shown). In comparison, ZIKV-116 bound to cells infected with DENV1, DENV2, or DENV4, but did not bind to DENV2 DIII or WNV DIII in ELISA.

Recently, in vivo models of ZIKV pathogenesis and antibody prophylaxis have been reported[8,10,11] in mice deficient in type I IFN signaling. To determine whether ZIKV-117 had therapeutic activity, the inventors treated 4 to 5 week-old WT male C57BL/6 mice at day −1 with anti-Ifnar1 mAb, and then inoculated animals with $10^3$ FFU of ZIKV-Dakar, an African strain that is pathogenic in mice. Subsequently, animals were treated with a single dose of ZIKV-117 or isotype control (hCHK-152) (Pal et al., 2013), on day +1 (100 μg; 6.7 mg/kg) or day +5 (250 μg; 16.7 mg/kg). Animals treated with the non-binding isotype control (hCHK-152) developed significant lethality compared to those receiving ZIKV-117 (FIG. 3A), which were protected even when administered only a single dose five days after virus inoculation.

Figure 8:
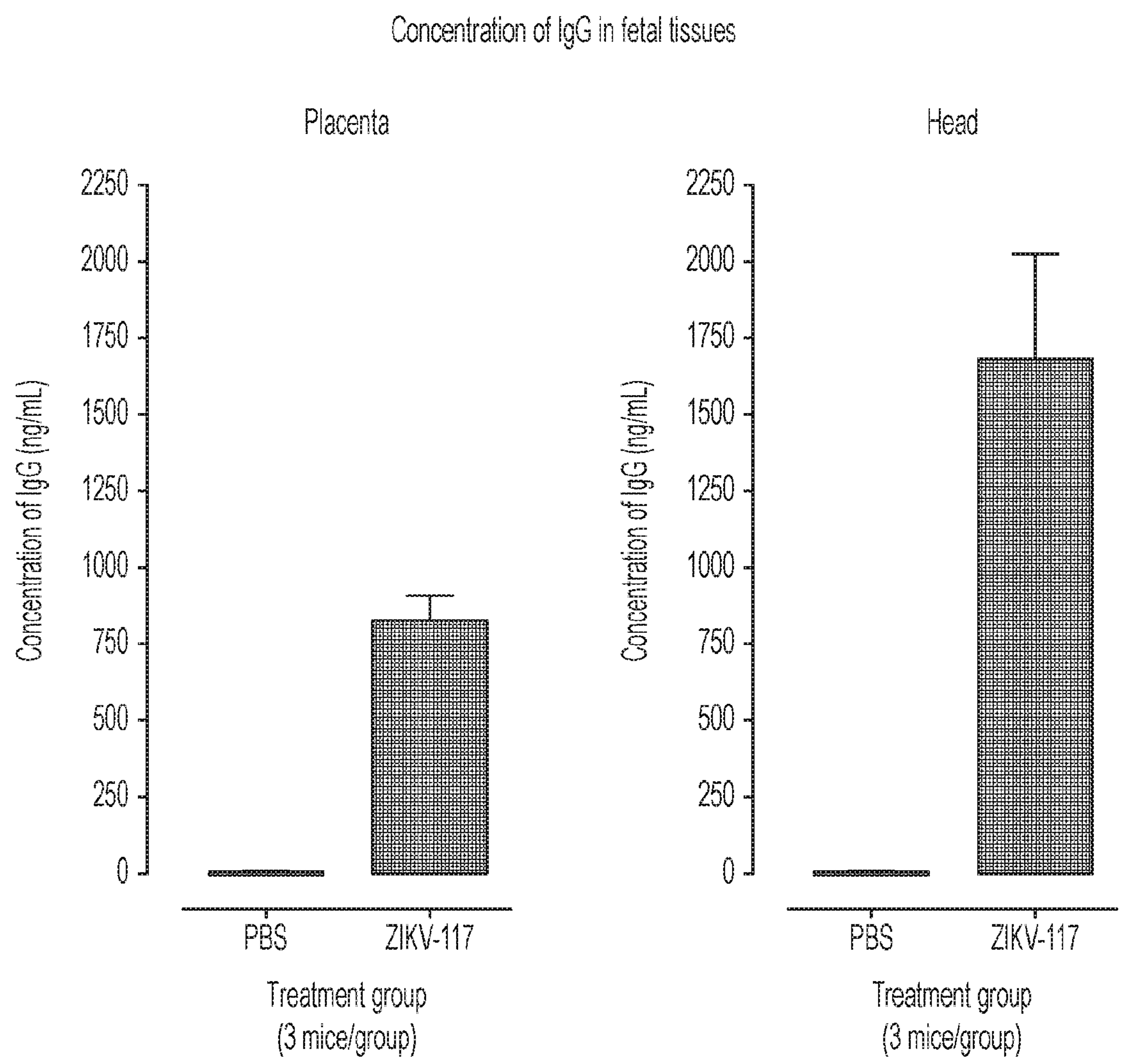
FIG. 8. Detection of human IgG in placenta or fetal head tissues after treatment of dams with ZIKV-117 or PBS treated pregnant mice. As described in FIGS. 3A-F, WT female mice were mated with WT sires and monitored for pregnancy. At E5.5, dams were treated with anti-Ifnar1 mAb and PBS or 250 μg of ZIKV-117. One day later (E6.5), dams were infected with $10^3$ FFU of ZIKV-Dakar. Fetuses and placentas (n=4 each) were harvested on E13.5, homogenized, and tested for human IgG by ELISA. Human antibody in tissues was captured on ELISA plates coated with ZIKV E protein and detected using goat anti-human IgG (Fc-specific) antibody. The quantity of antibody was determined by comparison with a standard curve constructed using purified ZIKV-117 in a dilution series. Concentration of ZIKV-117 detected in treated or PBS mock-treated placenta or fetal head tissues, with standard curve. Four replicates were performed for each mouse tissue; results were averaged for each mouse. The graphs represent the mean±SEM from 3 mice per group.

The inventors and others have demonstrated intrauterine growth restriction, placental injury, and fetal demise following ZIKV infection of pregnant mice with deficiencies in type I IFN signaling (Mysorekar et al., 2016; Miner et al., 2016; Yockey et al., 2016). To assess the protective ability of ZIKV-117 during fetal development, WT pregnant dams were treated at day −1 (embryo day (E)5.5) with an anti-Ifnar1 mAb. At the same time, these animals were administered vehicle control (PBS), 250 μg isotype control hCHK-152, or 250 μg ZIKV-117 as prophylaxis. One day later, dams were infected subcutaneously with $10^3$ FFU of ZIKV-Dakar. Fetuses at E13.5 from anti-Ifnar1 mAb treated dams given PBS or hCHK-152 showed high levels (e.g., ~$10^5$ to $10^7$ FFU equivalents/g) of viral RNA in the placenta and fetal brain (FIG. 3B). In comparison, mice treated with ZIKV-117 had markedly reduced levels of virus in the placenta and fetal brain (e.g., ~$10^0$ to $10^3$ FFU equivalents/g) (FIG. 3B). This phenotype was associated with transport of antibody across the maternal-fetal placental barrier such that levels (816±53 ng/ml for the placenta and 1,675±203 ng/ml for the fetal head) of human ZIKV E-specific IgG were detected (FIG. 8). It should be noted that the levels of neonatal Fc receptor (FcRn) in the placenta of mice are lower than other mammalian species (Kim et al., 2009), thus reduced levels of transport of maternal or exogenous IgG into the fetus is expected (Pentsuk & van der Laan, 2009). Although this factor could underestimate the therapeutic effect of exogenous anti-ZIKV IgG or maternal antibodies, the inventors achieved levels in placenta and fetal head that still were orders of magnitude above the $FRNT_{50}$ value for ZIKV-117. Dams treated with ZIKV-117 also had lower levels of viral RNA in the maternal brain and serum (FIG. 3C).

Antibody-dependent enhancement (ADE) of infection of the closely related DENV is due to cross-reactive antibodies that fail to neutralize heterologous serotype infection and instead facilitate uptake and infection of FcγR-expressing myeloid cells (Morens, 1994). Because flavivirus antibodies can promote ADE in cell culture (Dejnirattisai et al., 2016; Charles and Christofferson, 2016) with unknown consequences in vivo, the inventors evaluated the protective efficacy of a recombinant form of ZIKV-117 IgG containing a leucine (L) to alanine (A) substitution at positions 234 and 235 (LALA) (Hessell et al., 2007), which lacked efficient binding to FcγR, retained interactions with FcRn (Hessell et al., 2007), and neutralized ZIKV in vitro equivalently compared to the parent mAb (FIGS. 9A-B). The LALA variant of ZIKV-117 showed similar protective activity against infection of the placenta and fetus relative to the parent mAb (FIG. 3D). As the majority of the protection conferred by ZIKV-117 in the pregnancy model likely is due to neutralization and not Fc effector functions, LALA variants could be used without a loss in potency or risk of ADE from a future infection with a heterologous flavivirus such as DENY.

The inventors next assessed the post-exposure efficacy of ZIKV-117 during pregnancy. Mice treated with anti-Ifnar1 mAb at E5.5 were infected with $10^3$ FFU of ZIKV-Dakar at E6.5 and then given a single dose of PBS, 250 μg of hCHK-152, or 250 μg of ZIKV-117 at E7.5. Compared to PBS or isotype control mAb treatment, administration of ZIKV-117 resulted in markedly reduced viral burden in the dams, the placenta, and fetus when measured at E13.5 (FIGS. 3E-F).

The inventors also evaluated the consequences of ZIKV-117 administration on pathology in the placenta and fetus. The reduction in viral load mediated by ZIKV-117 was associated with decreased destruction of the placenta (as judged by labyrinth layer and overall placenta area), less trophoblast cell death, and increased body size of the fetus (FIGS. 4A-C) compared to fetuses of PBS- or hCHK-152-treated dams. When administered as prophylaxis, ZIKV-117 fully protected against ZIKV-induced placental insufficiency and intrauterine growth restriction, as the placental area and fetal size from infected dams treated with anti-ZIKV mAb were similar to that of uninfected placentas[14]. In situ hybridization revealed an almost complete absence of viral RNA in the junctional zone and decidua of the placenta in animals treated with ZIKV-117 compared to staining observed in PBS or hCHK-152-treated controls (FIG. 4D). The inventors also observed vascular damage associated with ZIKV infection of the placenta (Miner et al., 2016), characterized as diminished vimentin staining of fetal endothelial cells, which was rescued by ZIKV-117 to levels similar to those in uninfected placentas (FIG. 4E). The histopathological data suggests that ZIKV-117 treatment can reduce the ability of ZIKV to cross the fetal endothelial cell barrier, and thereby prevent vertical transmission and improve placental health and fetal outcome.

TABLE 1

NUCLEOTIDE SEQUENCES FOR ANTIBODY VARIABLE REGIONS

| Clone | Variable Sequence Region | SEQ ID NO: |
|---|---|---|
| ZIKV-2 heavy | CAGGTGCAGCTGGTGGAGTCTGGGGGAGGCGTGGTCCAGCCTGGGAGGTCC CTGAGACTCTCCTGTGCAGCCTCTGGATTCACCCTCAGTACTTTTGCTATGCACT GGGTCCGCCAGGCTCCAGGCAAGGGGCTGCAGTGGGTGGCTGTTACATCATA TGATGGAAGCAGTAAATTCTACGCAGACTCCGTGGAGGGCCGATTCACCATCT CCAGAGACACGTCCAAGAACACGTTGTATCTGCAAATGACCAGCCTGACAGCT GAGGACACGGCTGTGTATTTCTGTGCGAGAGGCTTCGGCGGTAGTGGTGATT ACTACGTAGGGGGATTTGATATCTGGGGCCAAGGGACCCTGGTCACCGTCTCC TCA | 1 |
| ZIKV-2 light | CAGTCTGCCCTGACTCAGCCTCGCTCAGTGTCCGGGTCTCCTGGACAGTCAGTC ACCATCTCCTGCACTGGAACCAGCAGTGATGTTGGTGGTTATGACTATGTCTCC TGGTACCAACAGCACCCAACCGAAGCCCCCAAACTCATCATTCATGATGTCAAT AAGCGGCCCTCAGGGGTCCCTGATCGCTTCTCTGGCTCCAAGTCTGGCAACAC GGCCTCCCTGACCATCTCTGGGCTCCAGGCTGAAGATGAGGCTGATTATTACT GCTGCTCTTTTGCAGGCAGCCACAGTTTTGTTTTATTCGGCGGAGGGACCAGG CTGACCGTCCTA | 2 |
| ZIKV-8 heavy | CAGGTGCAGCTGGTGGAGTCCGGGGGACGCGTGGTCCAGCCTGGGAGGTCCC TGAGGCTCTCCTGTGCGGCCTCTGGATTCACCTTCAGTAATTATGCCATGCACT GGGTCCGCCAGGCTCCAGGCAAGGGGCTGGAGTGGGTGGCTGTTATCTCATA CGATGGAAGTTATACACATTACACAGAGGCCGTGAGGGACCGATTCACCATCT CCAGAGACAATTCCAAGAGGACGGTGTGGCTGGAAATGAACAGTCTGAGAGT CGACGACACGGCTATGTATTACTGTGCGAGAGATGCGCTTGGATACTATGATA ATTCTGATTATACTTCTTGGGGCCTGGGGACCCTGGTCACCGTCTCCTCA | 3 |
| ZIKV-8 light | GAAATTGTGTTGACGCAGTCTCCAGACACCCTGTCTTTGGCTCCAGGGGAAAG AGCCACCCTCTCGTGCAGGGCCGGGCAGACTATTACCAGCAGCCACTTAGCCT GGTACCGGCTAAAACCCGGCCAGGCTCCCAGACTCATCATCTATGATGCATCC AGCAGGGCCACTGGCATCCCAGACAGGTTCAGTGGCAGTGGGTCTGGGACAC AGTTCACTCTCACCATCAGCAGACTGGAGCCTGAAGATTTTGCAGTATATTACT GTCAGCAGTATGCTACCCCACCGTGGACGTTCGGCCAAGGGACCAAGGTGGA GATCAAA | 4 |
| ZIKV-12 heavy | GAGGTGCAGCTGGTGGAGTCTGGGGGAGGCTTGGTCCAGCCTGGGGGGTCC CTGAGACTCTCCTGTGTAGCCTCTGGATTCACCTTCAGCGATTATGCTATGCAC TGGGTCCGCCAGGCTCCAGGGAAGGGACTGGAATATGTTTCAACCATTAATAG TAATGGGGGTAGCACATTTTATGCGGACTCTGTGCAGGACAGATTCACCATCT CCAGAGACAATTCCAAGAACACGCTTTATCTTCAAATGGACAGCCTGAGACCT GAGGACATGGCTGTCTATTATTGTGTGAGTCTGTACAACTATCCAGTCTTAGAC TACTGGGGCCTGGGAACCCTGGTCACCGTCTCCTCA | 5 |
| ZIKV-12 light | CAGGCTGTGGTGACTCAGGAGACCTCACTGACTGTGTCCCCAGGAGGGACAG TCACTCTCACCTGTGGCTCCAGCACTGGAGCTGTCACCAGTGGTCATTATCCCT ACTGGTTCCAGCAGAAGCCTGGCCAAGCGCCCAGGACACTGATTTATCATACA AACAACAAACACTCCTGGACACCTGCCCGGTTCTCAGGCTCCCTCCTTGGGGG CAAAGCTGCCCTGACCCTTTCGGGTGCGCACCCCGACGATGAAGCTGAATACT ACTGTTTGATCTTGTATCCTGATGCTCGCGTCTTTGGCGGAGGGACCAAGCTG ACCGTCCTA | 6 |
| ZIKV-15 heavy | CAGGTGCAGCTGGTGGAGTCTGGGGGAGGCGTGGTCCAGCCTGGGGGGTCC CTGAGACTCTCCTGTGCAGCGTCTGGATTCACCTTCAGCACCCATGACATGCAC TGGGTCCGCCAGGCTCCAGGCAAGGGGCTGGAGTGGGTGGCACTTATACGGT TTGGTGGCAAAGATATATACTATGCAGACTCCGTGGAGGGCCGATTCACCGTC TCCAGAGACAATTCCATGAACACGCTCTATCTGCAACTGAGCGGCCTGAGAGC TGATGACACGGCTCTGTACTACTGTGCGAAAGGCGCCCGATTCTATGATTCTAA TGGTTTCCCCGTTTACGCTGAATACTTCGAACACTGGGGCCAGGGCACCCTGG TCACCGTCTCCTCA | 7 |
| ZIKV-15 light | GACATCCAGATGACCCAGTCTCCATCCTCCCTGTCTGCATCTGTAGGAGACAGA GTCACCATCACTTGCCGGGCGAGTCAGGACATCAGCAATTTTTTAGCCTGGTAT CAGCAGAGACCAGGGAAAGTTCCTAAACTCTTGATCTATGCTGCATCCACCTTG CAATCTGGGGTCCCATCTCGGTTCAGTGGCAGTGGGTCTGGGACAGATTTCAC TCTCACCATCAGCAGCGTGCAGCCTGAAGATGTTGCAACTTATTTCTGTCAAAA GTATAACAATGCCCCGCTCACATTCGGCGGAGGGACCAAGGTAGAGATCAAA | 8 |
| ZIKV-19 heavy | CAGGTGCAGCTGGTGCAGTCAGGGCCTGAGGTGAAGAAGCCGGGGTCCTCG GTGAAGGTCTCCTGCAAGGCTTCTGGAGTCAGCTTCAACACCTATGAGATCAG CTGGGTGCGACAGGCCCCTGGACAAGGGCTTGAGTGGATGGGAAGGATCATC CCTATCTTTGCTACACCAACCTACGCACTGAAGTTCCAGGGCAGAGTCACGATT ACCACGGACGAATCCACGACCACAGGTTACATGGAGCTGAGCAGCCTGAGAT CTGAGGACACGGCCGTGTATTACTGTGCGGGAAGGCCCTATGGTCCGGGGAG TTGGTTGCCCCTGGACGTCTGGGGCCAAGGGACCCTGGTCACCGTCTCCTCA | 9 |

TABLE 1-continued

NUCLEOTIDE SEQUENCES FOR ANTIBODY VARIABLE REGIONS

| Clone | Variable Sequence Region | SEQ ID NO: |
|---|---|---|
| ZIKV-19 light | GACATTGTGATGACCCAGTCTCCATCCTCCCTGTCTGCATCTGTAGGAGACAGA GTCACCATCACTTGCCGGGCGAGTCAGGGCATTAGCTCTTATTTGGCCTGGTAT CAGCAAAAACCAGGGAAACTTCCTAAGCTCCTGATCTATGCTGCATCCACTTTG CAATCAGGGGTCCCATCTCGGTTCAGCGGCAGTGGATCTGGGACAGATTTCAC TCTCACCATCAGCAGCCTGCAGCCTGAAGACGTTGCAGCTTATTACTGTCAAAA GTATGACAGTGCCCCATTCACTTTCGGCCCTGGGACCAAAGTGGATCTCAAA | 10 |
| ZIKV-27 heavy | CAGGTGCAGCTGGTGCAGTCTGGACCTGAGGTGAAGAAACCTGGGGCCTCAG TGAAGGTCTCCTGCAAGGCTTCTGGTTTCACCTCTATGAATTATGGTATCAGCT GGGTGCGACAGGCCCCTGGACAAGGGCTTGAGTGGATGGGATGGATAATCGC TTACAATGGAAACACAAACTATGCACAGAAGTTCCAGGGCAGAGTCTCCATGA CCATAGACACATCCACGACCACTGCCTACATGGAACTGAGGAGCCTGAGATCT GACGACACGGCCGTATATTACTGTGCGAGCCGAATAGAAGTGGCTGATACGG TCTACGACCCCTGGGGCCAGGGAACCCTGGTCACCGTCTCCTCA | 11 |
| ZIKV-27 light | GAAATTGTGTTGACTCAGTCTCCAGGCACCCTGTCTTTGTCTCCAGGGGAAAG AGCCACCCTCTCGTGCAGGGCCAGTCAGACTACTAGCAGCAGCTTCTTAGCCT GGTACCAGCAGAAGCCTGGCCAGGCTCCCAGGCTCCTCATCTATGGTGCATCC AACAGGGCCACTGGCATCCCAGACAGGTTCAGTGGCAGTGGGTCTGGGACAG ACTTCACTCTCACTATCAGCAAACTGGAGCCTGAAGATTTTGCGGTCTATTACT GTCAGCAGTATGACAGCTCACCTCCGGGATTCACTTTCGGCCCTGGGACCAAA GTGGATATCAAA | 12 |
| ZIKV-33 heavy | CAGGTGCAGCTGGTGGAGTCTGGGGGAGCTGTGGTCCAGCCTGGGAGGTCCC TGAGACTCTCCTGTGCAGCCTCTGGATTAAGTTTCAGTGACTATGCTATCCACT GGGTCCGCCAGGCTCCAGGCAAGGGGCTGGAGTGGGTGGCAGTAATTGCACA TGATGGAAGGAATAAATATTATGCCGACTCCGTGATGGGCCGAGTCGCCATCT CCGGAGACAATTCCAAGAACACGGTGTATCTGCAAATGAGCAGCCTGAGAGC TGAAGACACGGCCACTTATTACTGTGCGAGAGGGTTTTACCATGATAAAACTG GTTCCTACTGGTACTTCGATCTCTGGGGCCGTGGCACCCTGGTCACCGTCTCCT CA | 13 |
| ZIKV-33 light | CAGTCTGTGTTGACTCAGCCGCCCTCAGTGTTTGCGGCCGCAGGACAGAGGGT CACCATCTCCTGCTCTGGAAGCAGCTCCAACATTGGGGATAATTATGTATCCTG GTACCAGCAGTTCCCAGGAACAGCCCCCAAAATCCTCATTTACGAGAATGATA AGCGAGCCTCAGGGATTCCTGACCGATTCTCTGGCTCCAAGTCTGGCACGTCA GCCACCCTGGGCATCACCGGACTCCGGACTGGGGACGAGGCCGATTATTTCTG CGGAACATGGGATAGCAGCCTGACTACAGCGGTTTTCGGCGGAGGGACCAAG TTGACCGTCCTA | 14 |
| ZIKV-46 heavy | GAGGTGCAGCTGGTGGAGTCTGGGGGAGGCTTGGTAAAGCCTGGGGGGTCG CTTAGACTCTCCTGTGCAACCTCCGGATTCAGTGTCACTAACGCCTGGATGAGC TGGGTCCGCCAGGCTCCAGGGAGGGGGCTGGAGTGGGTTGGCCGTATTAAAA ACAAAGCTGATGATTGGACAACAGACTACGCTGCACCCGTGAGAGGCAGATT CACCATCTCAAGAGATGATTCTAAAGACACCGTGTATCTGCAAATGAACAGCC TGAAAAGCGAGGACACAGCCCTTTATTACTGTAGTACTTATTATTATGATAGTA GTGGTCATTTTGTTGACTACTGGGGCCAGGGAACCCTGGTCACCGTCTCCTCA | 15 |
| ZIKV-46 light | GAAATTGTGTTGACTCAGTCTCCAGCCACCCTGTCTTTGTCTGCAGGGGACAGA GCCACCCTCTCCTGCAGGGCCAGTCAGAGTGTTAGCATCTACTTACTTTGGTAC CAACAGAAACCTGGCCAGGCTCCCAGGCTCCTCATCTATGATGCATCCAAGAG GGCCACTGGCATCCCAGCCAGGTTCAGTGGCAGTGGGTCGGGGACAGACTTC ACTCTCACCATCACCAGCCTAGAGCCTGAAGATTTTGCAGTTTATTACTGTCTTC AGCGTGGCATCTGGCCATCGTTCGGCCAAGGGACCAAGGTGGAAATCAAA | 16 |
| ZIKV-47 heavy | CAGGTGCAGCTGGTGGAGTCTGGGGGAGGCGTGGTCCAGCCTGGGAGGTCC CTGAGACTCTCCTGTGCAGCCTCTGGATTCACCTTCACTTCCTATGCTTTTCACT GGGTCCGCCAGGCTCCAGGCAAGGGCCTGGAGTGGGTGGCAGTTATTTCATA TGATGGAAGCCAAAAATTCTACGCAGACTCTGTGATGGACCGCTTCACCATCTC CAGAGACAGTTCCAAGAACACGCAGTATCTACAAATGGACAGCCTGAGACCTG AGGACACGGCTGTGTATTACTGTGCGACCAAGGGGCAGTCCCAGATTCCTGTT ACCGCTGAATACTTCGAACATTGGGGCCGGGGCACCCTGGTCACCGTCTCCTC A | 17 |
| ZIKV-47 light | CAGTCTGTGCTGACGCAGCCGCCCTCAGTGTCTGGGGCCCCAGGGCAGAGGG TCACCATCTCCTGCACTGGCAGCAGCTCCAACATCGGGGCAGGTTATGATGTG CACTGGTACCAGCAGCTTCCAGGAACAGCCCCCAAACTCGTCATCTTTGCTAAC AGCAATCGGCCCTCAGGGGTCCCTGACCGATTCTCTGGCTCCAAGTCTGACAC CTCAGCCTCCCTGGCCATCACTGGGCTCCAGGCTGAGGATGAGGCTGATTATT ACTGCCAGTCCTATGACAGCAGCCTGAGTCGTTATGTGGTATTCGGCGGAGGG ACCCAGGTGACCGTCCTA | 18 |

TABLE 1-continued

NUCLEOTIDE SEQUENCES FOR ANTIBODY VARIABLE REGIONS

| Clone | Variable Sequence Region | SEQ ID NO: |
|---|---|---|
| ZIKV-48 heavy | CAGGTGCAGCTGGTGGAGTCTGGGGGAGGCGTGGTCCAGCCTGGGAGGTCC CTGAGACTCTCCTGTGCAGCCTCTGGATTCACCTTCAGTAGCGATGCTATGCAC TGGGTCCGCCAGGTTCCAGGCAAGGGGCTGGAGTGGGTGGCAGTTACATCAT ATGATGGAAGTAATAAATACTACGCAGACTCCGTGGAGGGCCGATTCACCATC TCCAGGGACAATTCCAAGAACACGCTGTTTCTTGAAATGACCAGCCTGAGAGT TGAGGACTCGGCTATATATTACTGTGCGAGAGGGTTTACGGTGATCCATGCTT TTGATATCTGGGGCCTAGGGACCCTGGTCACCGTCTCCTCA | 19 |
| ZIKV-48 light | CAGTCTGTGCTGACTCAGCCTCGCTCAGTGTCCGGGTCTCTTGGACAGTCAGTC TCCATCTCCTGCACTGGAACCAGCAGTGATGTTGGGGGATATAACTATGTCTCC TGGTACCTACAACACCCAGGCAAAGCCCCCAAACTCATCATTTATGATGTCAGT AAGCGGCCCTCAGGAGTCCCTAGTCGCTTCTCTGGCTCCAAGTCTGGCAACAC GGCCTCCCTGACCATCTCTGGGCTCCAGGCTGAGGATGAGGCTGATTATTCCT GCTCCTCATATGCAGGCACCTTTGTGGTCTTCGGCGGAGGGACCAAGCTGACC GTCCTA | 20 |
| ZIKV-49 heavy | CAGGTGCAGCTGGTGGAGTCGGGCCCAGGACTGCTGAAGCCTTCGGAGACCC TGTCCCTCACCTGCGCTGTCTCTGGTGGCTCCATCAACAGTAGTAGTTTCCACT GGGGCTGGATCCGCCAGCCCCCAGGGAAGGGGCTGGAGTGGATTGGGGCTA TCTATTATACTGGGAGCACCTACTACAACCCGTCCCTCAAGAGTCCAGTCACCG TTTCAGTGGACACGTCCAAGAACCAGTTCTCCCTGGAGCTGAGCTCTGTGACC GCCGCGGACACGGCCGTCTATTTCTGTGCGAGAGTGGTTGCTACAGTTACTAC GAGACGGGGGCTGGGGTCTTTTGATATCTGGGGCCAAGGGACCCTGGTCACC GTCTCCTCA | 21 |
| ZIKV-49 light | GACATCGTGATGACCCAGTCTCCATCTTCCGTGTCGGCATTTGTAGGAGACAG AGTCACCATCACTTGTCGGGCGAGTCAGGGTATTAGCAACTGGTTAGCCTGGT ATCAGCAGAAACCAGGGAAAGCCCCTAAGCTCCTGATTTATGCTGCATCCAGT TTGCAAAGTGGGGTCCCATCAAGGTTCAGCGGCAGTGGATCTGGGACAGATTT CACTCTCACCATCAGCAGCCTGCAGCCTGAAGATTTTGCAACTTACTATTGTCA ACAGGCTAACAGTTTCCCGTGGACGTTCGGCCAAGGGACCAAGGTGGAAATC AAA | 22 |
| ZIKV-50 heavy | GAGGTGCAGCTGGTGGAGTCTGGGGGAGGCTTGGTCCAGCCTGGAGGGTCC CTGAGACTCTCCTGTGCAGCCTCTGGATTCACCTTCAGTGACCCCTACATGGAC TGGGTCCGCCAGGCTCCAGGGAAGGGGCTGGAGTGGGTTGGCCGTGTTCGAA ACAAACCTAACAGTTACACCACAGAATACGCCGCGTCGGTGACAGGCAGGTTC ACCATCTCAAGAGATGATTTAAAGAACTCAGTGTATCTGCAAATGAACAGCCT GAAAACCGAGGACACGGCCGTGTATTTTTGTGTTAGAGTGGCCCTTCCAAAGG CTTTTGATGTCTGGGGCCAAGGGACCCTGGTCACCGTCTCCTCA | 23 |
| ZIKV-50 light | GACATCCAGATGACCCAGTCTCCACCCTCCCTGTCTGCATCTGTAGGAGACAGA GTCACCATCACTTGCCAGGCGAGTCAGGACATTAGTATCTATTTAAATTGGTTT CAGCACAAACCAGGGAAAGCCCCTAAGCTCCTGATCTACGATGCTTCCAATTT GGAAACAGGGGTCCCATCAAGGTTCAGTGGAAGTGGATCTGGGACAGACTTT TCTTTCACCATCAGCGGCCTGCAGCCTGAGGACGTTGCATCATATTACTGTCTA CAGTATGATAATCCCCCCACTTTCGGCGGAGGGACCAAGGTGGAGATCAAA | 24 |
| ZIKV-55 heavy | CAGGTGCAGCTGGTGCAGTCTGGAGCTGAGGTGAAGAAGCCTGGGGCCTCAG TGAAGGTCTCCTGTAAGGCCTCTGGTTACACCTTTACCAGTTTTGGTATCAGCT GGGTGCGACAGGCCCCTGGACAAGGGCTTGAGTGGATGGGATGGAATAGCG CTTGGATCAGTGCACACAATGGCAACGCAGTCTATGGAAAGAAGTTCCAGGG CAGAGTCGCCATGACCATAGACACGTCCACGAGCACAGCCTACTTGGACGTGA GGAGCCTGAGATCTGACGACACGGCCGTCTATTACTGTGCGAGAGTCGGAGG ATGGCAACAGATTCCCTACTTTGACTTCTGGGGCCAGGGAACCCTGGTCACCG TCTCCTCA | 25 |
| ZIKV-55 light | GACATTGTGATGACCCAGTCTCCATCCTTCCTGTTTGCTTCTGTAGGAGACAGA GTCACCATCACTTGCCGGGCCAGTGAGGGCCCTGACAGTTATTTAGCCTGGTA TCAGCAAAAGCCAGGGAAAGCCCCTAACCTCCTGATCTATGCTGCTTCCACTTT GCAAAGTGGGGTCCCATCACGGTTCAGCGGCAGTGGATCTGGGACAGAATTC ACTCTCACAATCAGCAGCCTGCAGCCTGAAGATTTTGCAACTTATTACTGTCAA CACCTTAATGGTTACCCTTCGTTCGGCCAAGGGACACGACTGGAAATTAAA | 26 |
| ZIKV-70 heavy | CAGGTGCAGCTGGTGGAGTCTGGGGGAGGCGTGGTCCAGCCTGGGGGGTCC CTGAGACTCTCCTGTGTAGGCTCTGGACTCACCCTCAGTTCCTATGCTATGCAC TGGGTCCGCCAGGCTCCAGGCAAGGGGCTGGAGTGGGTGGCAGTTATCTCAT CTGATGGAAGCAATCGATACTACGCGGACTCCGTGGAGGACCGATTCACCATC TCTAGAGACAATTCCAAGAACATACTGTACCTACAAATGAACACCCTGAGACCT GACGACACGGCTTTTTATTACTGTGCGAGAGGTTACTACTTTGATGATAGTGGT TCTTACTGGTACTTCGATCTCTGGGGCCGTGGCACCCTGGTCACCGTCTCCTCA | 27 |

TABLE 1-continued

NUCLEOTIDE SEQUENCES FOR ANTIBODY VARIABLE REGIONS

| Clone | Variable Sequence Region | SEQ ID NO: |
|---|---|---|
| ZIKV-70 light | CAGTCTGTGTTGACGCAGCCGCCCTCAGTGTCTGCGGCCCCAGGACAGAAGGT CACCATCTCCTGCTCTGGAAGCAGCTCCAACATTGGGAATAATTATGTATCCTG GTACCAGCAACTCCCAGGAGCAGCCCCCAGAGTCCTCATTTATGAGGATAGTA AGCGACCCTCAGGGATTCCTGACCGATTCTCTGGCTCCAAGTCTGGCACGTCA GCCACCCTGGCCATCACCGGACTCCAGACTGGGGACGAGGCCGATTATTACTG CGCAACATGGGATGGCGGGCTGAGTGTTATTTTCGGCGGAGGGACCCAGGTG ACCGTCCTA | 28 |
| ZIKV-71 heavy | CAGGTTCAGCTGGTGCAGTCTGGGGGCGAGGTGAAGAAGCCTGGGGCCTCAG TGAAGGTCTCCTGCAAGGCTTCTGGTTACAGCTTCATTAACTATGGAATCAGTT GGGTGCGGCAGGCCCCTGGACAAGGGCTTGAGTGGATGGGATATATTATCCC TTACAATGGGGACACGAGCTATGCACAGCAATTCCAGGGCAGAGTCACCATG GCCGCAGACACATCCGCGACAACAGTTTTCATGGAAGTGGGGAGCCTGAGAT TAGACGACACGGCCGTATACTACTGTGCGAGAGCAATAGTGGGGGAAACTGT GACAGGCTATGTCTATGGTATGGACGTCTGGGGCCAAGGGACCCTGGTCACC GTCTCCTCA | 29 |
| ZIKV-71 light | GACATCCAGTTGACCCAGTCTCCATCCTCCCTGTCTGCATCTGTAGGAGACAGA GTCACCATCACTTGCCGGGCCAGTCAGGGCATTGACATTTTTTTGGCCTGGTAT CAGCAAAAGCCAGGGAAAGCCCCTAACCTCCTGATCTATTCTGCATCCACTTTG CAAAGTGGGGTCCCATCAAGGTTCAGCGGCAGTGGATCTGGGACATTTTTCAC TCTCACCATCAGCAGCCTGCAGCCTGAAGATTTTGCAACTTATTACTGTCAATA TCTTAATACTTCCCCATGGACGTTCGGCCAAGGGACCAAGGTGGAAATCAAA | 30 |
| ZIKV-78 heavy | GACATCCAGTTGACCCAGTCTCCATCCTCCCTGTCTGCATCTGTAGGAGACAGA GTCACCATCACTTGCCGGGCCAGTCAGGGCATTGACATTTTTTTGGCCTGGTAT CAGCAAAAGCCAGGGAAAGCCCCTAACCTCCTGATCTATTCTGCATCCACTTTG CAAAGTGGGGTCCCATCAAGGTTCAGCGGCAGTGGATCTGGGACATTTTTCAC TCTCACCATCAGCAGCCTGCAGCCTGAAGATTTTGCAACTTATTACTGTCAATA TCTTAATACTTCCCCATGGACGTTCGGCCAAGGGACCAAGGTGGAAATCAAA | 31 |
| ZIKV-78 light | CAGGCTGTGGTGACTCAGGAGCCCTCACTGACCGTGTCCCCAGGAGGGACAG TCACTTTCACCTGTGCCTCCAGCACTGGAGCTGTCACCAGTGGTCATTATCCCT ACTGGTTCCAGCAGAAACCTGGCCAAGCCCCCAGGACACTGATTTATCATTCTT CCAAGAAACACTCCTGGACTCCTGACCGGTTCTCAGGCTCCCTCCTTGGGGGC AAAGCTGCCCTGACGCTTTCGGGGGCGCAGCCTGAAGATGAGGCTGAGTATT ACTGCTTACTCTCTTATAGTGGTGGTCGGCCGGTGTTCGGCGGAGGGACCCAG GTGACCGTCCTA | 32 |
| ZIKV-81 heavy | CAGGTGCAGCTGGTGGAGTCTGGGGGAGGCGTGGTCCAGCCTGGGAGGTCC CTGAGACTCTCCTGTGCAGCCTCTGGATTCATCTTCAGTAACTTTGCTATGCACT GGGTCCGCCAGGCCCCAGGCAAGGGGCTGGAGTGGGTGGCAGTTATTTCATA TGATGGAAGCAATACATACTATTCAGACTCCGTGGAGGGCCGATTCACCATCT CCAGAGACAATTCCAAGAACATGCTGTTCTTGGAAGTGAACACCCTGAGAACT GAGGACACTGCTGTATATTACTGTGCGATCGGAGGGGGGCCCCCCGATTTTTT GGCCGCGCCTTTCAACGCTGAAGTCTTGCAGCACTGGGGCCAGGGCACCCTGG TCACCGTCTCCTCA | 33 |
| ZIKV-81 light | CAGTCTGTGCTGACGCAGCCGCCCTCAGTCTCTGGGGCCCCAGGGCAGAGGG TCACCATCTCCTGCACTGGGAGCAGTTCCAACATCGGGGCCGGTTATGATATA CATTGGTACCAGCAGCTTCCAGGAACAGCCCCCAAACTCCTCATCTATGGTAAC ACCAACCGGCCCTCAGGGGTCCCGGACCGATTCTCTGGCTCCAAGTCTGGCAC CTCAGGCTCCCTGGCCATCACTGGGCTCCAGGCTGAGGATGAGGCTGATTATT TCTGCCAGTCGTATGACACCGGCCTGAGTGTGGTATTCGGCGGAGGGACCCA GGTGACCGTCCTA | 34 |
| ZIKV-82 heavy | Not determined | 35 |
| ZIKV-82 light | GACATCCAGATGACCCAGTCTCCATCTTCCGTGTCTGCGTCTGTGGGGGACAC AGTCACCATCACTTGTCGGGCGAGTCAGGATATCACTTACGTGTTAACCTGGTA TCAGCAGAAACCAGGGAAAGCCCCTAAACTCCTGATCTATGCTGCAGCCAATT TGGCAAGTGGGGTCCCGTCAAGGTTCAGCGGCAGTGGATCTGGGACACATTT CACTCTCACCATCCGCAGCCTGCAGCCTGAAGATTTTGCAACTTACTATTGTCA ACAGGCTAACAGTTTCCCCTGGACGTTCGGCCAAGGGACCAAGGTGGACATCA AA | 36 |
| ZIKV-86 heavy | CAGGTGCAGCTGGTGGAGTCTGGGGGAGGCGTGGTCCAGCCTGGGAGGTCC CTGAGACTCTCCTGTGCAGCCTCTGGATTCACCTTCAGTGATTATGCCATGCAC TGGGTCCGCCAGGCTCCAGGCAAGGGACTGGAGTGGGTCGCAGTTATATCAT ATGATATAAATACAAAATATTATGCAGAGTCCGTGGAGGGGCGATTTTCCATC TCCAGAGACGATTCCATAAACACCGTTTATCTACAAATGAACAGCCTGAGACCT | 37 |

TABLE 1-continued

NUCLEOTIDE SEQUENCES FOR ANTIBODY VARIABLE REGIONS

| Clone | Variable Sequence Region | SEQ ID NO: |
|---|---|---|
| | GACGACACGGCTGTCTATTTCTGTGCGAGAGATGTCTATGGCGGGGGGGTTCC CTGGGGCCAGGGAACCCTGGTCACCGTCTCCTCC | |
| ZIKV-86 light | GACATCCAGATGACCCAGTCTCCTTCCACCCTGTCTGCATCTGTAGGAGACAGA GTCACCATCACTTGCCGGGCCAGTCAGAGTGTTAGTGACTGGTTGGCCTGGTA TCAGCAGAAACCAGGGAAAGCCCCTAAACTCCTGATCTATAAGGCGTCTACTT TAGAAAGTGGGGTCCCATCAAGGTTCAGCGGCAGTGGATCTGGGACAGAGTT CACTCTCACCATCAGCAGCCTGCAGCCTGATGATTTTGCAACTTATTACTGCCA CCAGTATAGTTTTTATTGGACGTTCGGCCAAGGGACCAAGGTGGATATCAAA | 38 |
| ZIKV-88 heavy | CAGGTGCAGCTGCTTGAGTCTGGGGGAGGCGTGGTCCAGCCTGGGAGGTCCC TGAGACTCTCCTGTGTAGCCTCTGGACTCACCTTCAGTACCTCTGCCATGCACT GGGTCCGCCAGGCTCCAGGCAAGGGACTGGAGTGGGTGGCAGTTATCTCATA TGATGGGAGCTATAAATTCTACGCAGATTCCGTGAGGGACCAATTCACCATCT CCAGAGACAATTCCAAGACCACGCTGTATTTGCAAATGGACGGCCTGACACCT GAGGACACGGCTGTATATTACTGTGCGAGAGGTTACAACGACGACAGTAGTG GGTCTTACTGGTATTTCGATCTCTGGGGCCGTGGCACCCTGGTCACCGTCTCCT CA | 39 |
| ZIKV-88 light | CAGTCTGTGTTGACGCAGCCGCCCTCAGTGTCTGCGGCCCCAGGACAGAAGGT CACCATGTCCTGCTCTGGAAGCAGCTCCAACATTGGGAGTAATTTCGTTTCCTG GTACCAGCAACTCCCAGGAACAGCCCCCAAGGTCCTCATTTTTGACAATAATCA GCGACCCTCAGGGATTCCTGACCGATTCTCCGGCTCCAAGTCTGGCACGTCAG CCACCCTGGCCATCACCGGACTCCAGCCTGGGGACGAGGCCGTTTATCATTGC GGAACATGGGATAGCAGCCTGACCTTCGCGGTCTTCGGCGGAGGGACCAAGC TGACCGTCCTA | 40 |
| ZIKV-116 heavy | GAGGTGAAGCTGGTGGAGTCTGGGAGAGGCCTAGTTCGGCCTGGGGGGTCC CTGAGACTCTCTTGTGCAGCCTCTGGATTCACCTTTAGCAACTATGCCATGAGC TGGGTCCGCCAGGGTCCAGGGATGGGACTGGAGTGGGTCTCAACGATCACTG CCGATAGTGATAGCAAATATTACGTGGACTCTGTGAAGGGCCGGTTCACCATC TCCAGAGACAATTCCAAGGACACATTATTTCTACACATGACCAGCCTGAGAGC CGAAGACACGGCCGTTTACTACTGTGCGAAAGATCGCCTCTCTCGGGGGGTCG GGGAGTTATATGACTCGTGGGGCCAGGGAACCCTGGTCACCGTCTCTTCA | 41 |
| ZIKV-116 light | GACATACAGATGACCCAGTCTCCTTCCACCCTGTCTGCATCTGTAGGAGACAGA GTCACCATCACTTGCCGGGCCAGCCAGAGTATTGATGTCTGGTTGGCCTGGTA TCAGCAGAAGCCAGGGAAAGCCCCTAAACTCCTGATGTATAAGACGTCTACTT TACAAACTGGGGTCCCATCAAGATTCAGCGGCAGTGGATCTGGGACAGAATTC ACTCTCACCATCAGCAGCCTGCAGACTGATGATTTTGCAACTTATTACTGCCAA AAGTACGATAGTTATCCGTGGACGTTCGGCCCAGGGACCAAGGTGGAAATCA AA | 42 |
| ZIKV-117 heavy | CAGGTGCAGCTGGTGGAGTCTGGGGGAGGCGTGGTCCGGCCTGGGGGGTCC CTCAGACTCTCCTGTGCAGCGTCTGGATTCACCTTCAAAAACTATGGCATCCAC TGGGTCCGCCAGGCTCCAGGCAAGGGGCCGGAGTGGGTGGCATTTGTACGGT ATGATGGAAATAACAAGTACTATGCAGACTCCGTGAAGGGCCGATTCACCATC TCCAGAGACAATGCCAAGAACACGCTGTCTCTGCAAATGAACAGCCTGAGAGT TGAAGACACGGCTGTCTATTTCTGTGCGAGGGATCCTGAAACTTTCGGGGGGT TTGACTACTGGGGCCAGGGAACCCTGGTCACCGTCTCCTCA | 43 |
| ZIKV-117 light | GAAACAGTGATGACGCAGTCTCCAGCCACCCTGTCTGTGTCTCCAGGGGAAAG AGGCACCCTCTCCTGCAGGGCCAGTGAGAGTGTTAGCAGCAACTTGGCCTGGT ACCAGCAGAAACCTGGCAAGGCTCCCCGGCTCCTCATCTATGGTGCATCCACC AGGGCCACTGGTATCCCAGACAGGTTCAGTGGCAGTGGGTCTGGGACAGAGT TCACTCTCACCATCAGCAGCCTGCAGTCTGAAGATTTTGCAGTTTATTACTGTCA GCAGTATTATTACTCGCCTCGAACGTTCGGCCAAGGGACCAAGGTGGAAGTCA AA | 44 |
| ZIKV-146 heavy | GAGGTGCAGCTGGTGGAGTCCGGGGGAGGCTTGGTCCAGCCTGGGGGGTCC CTGAGACTCTCCTGTGTCGCCTCTGGATTTACGTTCAGTGATTATGCTATGCAC TGGGTCCGCCAGGCTCCAGGGAAGGGACTGGAATATGTTTCAACCATTAATAG TAATGGGGGTAACACTTTTTATGCGAACTCTGTGGAGGACAGATTCACCATCTC CAGAGACAATTCCAAGAGCACGCTTTATCTTCAACTGGACAGCCTGAGACTTG AGGACACGGCTGTCTATTATTGTGTGAGTCTGTGGAACTATCCAGTCTTAGACT ACTGGGGCCTGGGAACCCTGGTCACCGTCTCCTCA | 45 |
| ZIKV-146 light | CAGGCTGTGGTGACTCAGGAGCCCTCACTGACTGTGTCCCCAGGAGGGACAG TCACTCTCACCTGTGGCTCCAGCACTGGAGCTGTCACCAGTGGTCATTATCCCT ACTGGTTCCAGCAGAAGCCTGGCCAAGCGCCCAGGACACTGATTTATCATACA AACAGCAAACACTCCTGGACACCTGCCCGGTTCTCAGGCTCCCTCCTGGGGGG CAAAGCTGCCCTGACCCTTTCGGGTGCGCAGCCCGAGGATGAGGCTGAATATT ACTGCTTGCTCTTGTATCCTGATGCTCGGGTATTCGGCGGAGGGACCAGGCTG ACCGTCCTA | 46 |

TABLE 1-continued

| NUCLEOTIDE SEQUENCES FOR ANTIBODY VARIABLE REGIONS | | |
|---|---|---|
| Clone | Variable Sequence Region | SEQ ID NO: |
| ZIKV-158 heavy | CAGGTGCAGCTGGTGGAGTCTGGGGGAGGCGTGGTCCAGCCTGGGAGGTCC CTGCGACTCTCCTGTACTTCCTCTGGGTTCACCTTCAATACCTATCCTATGCACT GGGTCCGCCAGGCTCCAGGCAAGGGGCTGGAGTGGCTGGCAACTATCTCATA TGTTGAAACTGATAAGTACTACACAGACTCCGTGCAGGGCCGATTCACCGTCT CCAGAGACAACTCGAAGAACACGCTTTATCTGCAAATGAACAGCCTGAGCGTT GAGGACACGGCTGTCTATTACTGTGCGAGAGGGTGGGCGGTGACTACGTCCC ATGCTTTTGATGTTTGGGGCCAAGGGACCCTGGTCACCGTCTCCTCA | 47 |
| ZIKV-158 light | CAGTCTGCCCTGACTCAGCCTCGCTCAGTGTCCGGGTCTCCTGGACAGTCAGTC ACCATCTCCTGCACTGGAACCAGCAGTGATGTTGGTGGTTATGACTTTGTCTCC TGGTACCAAGAGCACCCAGGCAAAGCCCCCAAACTCATGATTTATGATGTCAC TAAGAGGCCCTCAGGGGTCCCTGATCGCTTCTCTGGCTCCAAGTCTGGCAACA CGGCCTCCCTGACCATCTCTGGGCTCCAGGCTGAGGATGAGGCTGATTATTATT GTTGCTCATATGCAGGCGGCTACACTTTCGTGGTCTTCGGCGGAGGGACCCAG GTGACCGTCCTA | 48 |
| ZIKV-165 heavy | CAGGTGCAGCTGGTGGAGTCTGGGGGAGGCGTGGTCCAGCCTGGGGGGTCC CTGAGACTCTCCTGTGCAGCGTCTGGATTCACCTTCACTAACTATGGCATGCAC TGGGTCCGCCAGGCTCCAGGCAAGGGCCTGGAGTGGGTGGCGTTTATACGGC CTGATGGAAATGATAAATACTATGCAGACTCCGTAAAGGGCCGATTCACCATC TCCAGAGACAATTCCAAGAACTCGCTCTATCTGCAAATGAACAGCCTGGGAGC TGAGGACACAGCTGTATATTATTGTGCGAAAGACTACTATCATACTACTGATGA TTATTGGGCTGAATTCTTCCAGCACTGGGGCCAGGGCACCCTGGTCACCGTCTC CTCA | 49 |
| ZIKV-165 light | GACATCCAGATGACCCAGTCTCCTTCCACCCTGTCTGCATCTGTAGGAGACAGA GTCACCATCACTTGCCGGGCCAGTCAGAGTATTAATAACTGGTTGGCCTGGTA TCAGCAGAAACCAGGGAAAGCCCCTAAGCTCCTAATCTATATGGCGTCCAACT TAGAAAGTGGGGTCCCATCACGGTTCAGCGGCAGTGGATCTGGGACAGAATT CACTCTCACCATCAGTAGCCTGCAGCCTGATGATTTTGCAAGTTATTACTGCCA ACACTATAATTTTTACCCCGGGTTCGGCCAAGGGACCAAGGTGGAAATCAAA | 50 |
| ZIKV-190 heavy | GAGGTGCAGCTGGTGGAGTCTGGGGGAGGCTTGATACAGCCTGGGGGGTCC CTGAGACTCTCCTGTGCAGCCTCTGGATTCACCTTTAGCAGCTATGCCATGAGC TGGGTCCGCCAGGCTCCAGGGAAGGGGCTGGAGTGGGTCTCAGCTATTAGTG GTAGTGGTGGTAGCACATACTACGCAGACTCCGTGAAGGGCCGGTTCACCATC TCCAGAGACAATTCCAAGAACACACTGTCTCTGCAAATGAACAGCCTGAGAGC CGAGGACACGGCCGTATATTACTGTGCGAGAGCCTTCTATTACGATTTTTGGAC CTTTGACTACTGGGGCCAGGGAACCCTGGTCACCGTCTCCTCA | 51 |
| ZIKV-190 light | CAGTCTGCCCTGACTCAGCCTCGCTCAGTGTCCGGGTCTCCTGGACAGTCAGTC ACCATCTCCTGCACTGGAACCAGCAGTGATGTTGGTGGTTATAACTATGTCTCC TGGTACCAACAGCACCCAGGCAAAGCCCCCAAACTCATGATTTATGCTGTCACT AAGCGGCCCTCAGGGGTCCCTGATCGCTTCTCTGGCTCCAAGTCTGGCAACAC GGCCTCCCTGACCATCTCTGGGCTCCAGGCTGAGGATGAGGCTGATTATTACT GCTGCTCATATGCAGGCAGCTACACTTATGTGGTATTCGGCGGAGGGACCAAG CTGACCGTCCTA | 52 |
| ZIKV-195 heavy | CAGGTGCAGGTGGTGGAGTCTGGGGGAGGCGTGGTCCAGCCTGGGAGGTCC CTGAGACTCTCCTGTGCAGCCTCTGGATTCACCTTCAGTAGCTCTGCCATGCAC TGGGTCCGCCAGGCTCCAGGCAAGGGGCTGGAATGGGTGGCAGTTATATCAT ATGATGGAAGTAATAAATACTATGGAGACTCCGTGAAGGGCCGATTCACCATC TCCAGAGACAATTCCAAGAACACGCTGTATCTGCAAATGCACAGCCTGAGAGC TGAGGACACGGCTGTTTATTACTGTGCGAAAGACCGAGATGCCTACAATACCG TCGGCTATTTTGCTTACTACTACGGTATGGACGTCTGGGGCCAAGGGACCCTG GTCACCGTCTCCTCA | 111 |
| ZIKV-195 light | CAGTCTGTGCTGACTCAGCCACCCTCGGTGTCTGAAGCCCCCAGGCAGAGGGT CACCATCTCCTGTTCTGGAAGCAGCTCCAACATCGGAAATAATGCTGTAAACTG GTACCAGCAGCTCCCAGGAAAGGCTCCCAAACTCCTCATCTATTATGATGATCT GCTGCCCTCAGGGGTCTCTGACCGATTCTCTGGCTCCAAGTCTGGCACCTCAGC CTCCCTGGCCATCAGTGGGCTCCAGTCTGAGGATGAGGCTGATTATTACTGTG CAGCATGGGATGACAGCCTGACTCGTTATGTCTTCGGAACTGGGACCAAGGTC ACCGTCCTA | 112 |
| ZIKV-204 heavy | CAGGTCACCTTGAGGGAGTCTGGCCCTGCGCTGCTGAAACCCACACAGACCCT CACACTGACCTGCACCTTCTCTGGATTCTCACTCAGCACTAATGAAACGTGTGT GAGCTGGATCCGTCAGCCCCCAGGGAAGGCCCTGGAGTGGCTTGCGCTCATT GATTGGGATGATGATCAATACTCCAGCACATCTCTGGCGGCCAGGCTCACCGT CTCTAAGGACACCTCCAAAAACCAGGTGGTCCTCACAATGACCAACGTGGCCC CTGTGGACACAGCCACGTATTACTGTGCACTGACACGTCCTACGTTGACTGCCC AGAACGGGGACAAATATTACAACTACTACTACGGCATGGACGTCTGGGGCCA AGGGACCCTGGTCACCGTCTCCTCA | 113 |

TABLE 1-continued

NUCLEOTIDE SEQUENCES FOR ANTIBODY VARIABLE REGIONS

| Clone | Variable Sequence Region | SEQ ID NO: |
|---|---|---|
| ZIKV-204 light | GAAATTGTGTTGACGCAGTCTCCAGGCACCCTGTCTTTGTCTCCAGGGGAAAG AGCCACCCTCTCCTGCAGGGCCAGTCAGAGTGTTAGCAGCATGTACTTAGCCT GGTATCAACAAAAACGTGGCCAGCCTCCCAGACTCCTCATCTATGGTACATTCA ACAGGGCCACTGGCATCCCAGACAGGTTCAGTGGCAGTGGGTCTGGGACAGA CTTCACTCTCACCATCAGCAGACTGGAGCCTGAAGATTTTGCAGTGTATTACTG TCAGCAGTATGGTAGCTCATCGTTCACTTTCGGCGGAGGGACCAAGGTGGAG ATCAAAC | 114 |
| ZIKV-216 heavy | GAGGTGCAGCTGGTGCAGTCTGGAGCAGAGGGGAAAAAGCCCGGTGAATCT CTGAAGATCTCTTGTAAGGGTTCTGGATACAATTTTTCCAACTACTGGATCGGC TGGGTGCGCCAGATGCCCGGGAAAGGCCTGGAGTGGATGGGCATCATCTATC CGGGTGACTCTGATACCAGATATAGCCCGTCCTTCCAAGGCCAGGTCACCATCT CAGCCGACAAGTCCATCAACACCGCCTATCTGCAGTGGAGAAGCCTGAGGGCC TCGGACTCCGCCATGTTTTATTGTGCGAGAGGGGTAATGATAACAACTCCTAAT CCTTACGACTGGTTCGACGCCTGGGGCCAGGGAACCCTGGTCACCGTCTCCTC A | 115 |
| ZIKV-216 light | CAGTCTGCCCTGACTCAGCCTGCCTCCGTGTCTGGGTCTCCTGGACAGTCGATC ACCATCTCCTGCACTGGAACCGGCAGTGACATTGGTACTTATGACTATGTCTCC TGGTACCAGCAACATCCAGGCAAAGCCCCCAAACTCATGATTTATGGTGTCACT AAGCGGCCCTCAGGGGTTTCTCATCGCTTCTCTGGCTCCAAGTCCGTCAACACG GCCTCCCTGACCATCTCTGGGCTCCAGGCTGAAGACGAGGCTGATTATTTCTGC AGTTCATATTCAACCAGCAGCACTTTTGTGGTATTCGGCGGAGGGACCAAGCT GACCGTCCTA | 116 |
| ZIKV-218 heavy | CAGGTGCAGCTGGTGGAGTCTGGGGGAGGCGTGGTCCAGCCTGGGAGGTCC CTGAGACTCTCCTGTGCAGCCTCTGGATTCACCTTCAGTGGCCATGCTTTGCAC TGGGTCCGCCAGGCTCCAGGCAAGGGTCTGCAGTGGGTGGCGGTGATATCAT CTGATGCTACCAGTAAGTTCTACGCAGACTCCGTGGAGGGCCGATTCAGCATC TCCAGAGACAACCCCAAAAACACACTGTTTCTGCAACTTGACAGCCTGGGACG TGAAGATTCGGGTATATATTACTGTGTGCTTGGTTTTACCAGCAGCTGGGACCT AACAGCCTACGCCTTTGACTATTGGGGCCAGGGAACCCTGGTCACCGTCTCCTC A | 117 |
| ZIKV-218 light | CAGTCTGCCCTGACTCAGCCTCACTCAGTGTCCGGGTCTCCTAGACAGTCAGTC ACCATCTCCTGCGTTGGAACTAGCGATGATGTTGGTGCTTATAGCTCTGTCTCC TGGTACCAACAACACCCGGGCAAAGCCCCCAAGCTCCTGGTTTATGATGTCGC TGAGCGGCCCTCAGGGGTCCCTGATCGCTTCTCTGGCTCCAATTCTGGCAACAC GGCCTCCCTGACTATCTCTGGGCTCCAGTCTGACGATGAGGCAACATATTACTG CTGCGCATATGCCGGCACATATGTGGTATTCGGGGGAGGGAACAAGGTGACC GTCCTA | 118 |

TABLE 2

PROTEIN SEQUENCES FOR ANTIBODY VARIABLE REGIONS

| Clone | Variable Sequence | SEQ ID NO: |
|---|---|---|
| ZIKV-2 heavy | QVQLVESGGGVVQPGRSLRLSCAASGFTLSTFAMHWVRQAPGKGLQWVAVTS YDGSSKFYADSVEGRFTISRDTSKNTLYLQMTSLTAEDTAVYFCARGFGGSGDYYV GGFDIWGQGTLVTVSS | 53 |
| ZIKV-2 light | QSALTQPRSVSGSPGQSVTISCTGTSSDVGGYDYVSWYQQHPTEAPKLIIHDVNK RPSGVPDRFSGSKSGNTASLTISGLQAEDEADYYCCSFAGSHSFVLFGGGTRLTVL | 54 |
| ZIKV-8 heavy | QVQLVESGGRVVQPGRSLRLSCAASGFTFSNYAMHWVRQAPGKGLEWVAVISY DGSYTHYTEAVRDRFTISRDNSKRTVWLEMNSLRVDDTAMYYCARDALGYYDNS DYTSWGLGTLVTVSS | 55 |
| ZIKV-8 light | EIVLTQSPDTLSLAPGERATLSCRAGQTITSSHLAWYRLKPGQAPRLIIYDASSRAT GIPDRFSGSGSGTQFTLTISRLEPEDFAVYYCQQYATPPWTFGQGTKVEIK | 56 |
| ZIKV-12 heavy | EVQLVESGGGLVQPGGSLRLSCVASGFTFSDYAMHWVRQAPGKGLEYVSTINSN GGSTFYADSVQDRFTISRDNSKNTLYLQMDSLRPEDMAVYYCVSLYNYPVLDYW GLGTLVTVSS | 57 |
| ZIKV-12 light | QAVVTQETSLTVSPGGTVTLTCGSSTGAVTSGHYPYWFQQKPGQAPRTLIYHTN NKHSWTPARFSGSLLGGKAALTLSGAHPDDEAEYYCLILYPDARVFGGGTKLTVL | 58 |

TABLE 2-continued

PROTEIN SEQUENCES FOR ANTIBODY VARIABLE REGIONS

| Clone | Variable Sequence | SEQ ID NO: |
|---|---|---|
| ZIKV-15 heavy | QVQLVESGGGVVQPGGSLRLSCAASGFTFSTHDMHWVRQAPGKGLEWVALIRF GGKDIYYADSVEGRFTVSRDNSMNTLYLQLSGLRADDTALYYCAKGARFYDSNGF PVYAEYFEHWGQGTLVTVSS | 59 |
| ZIKV-15 light | DIQMTQSPSSLSASVGDRVTITCRASQDISNFLAWYQQRPGKVPKLLIYAASTLQS GVPSRFSGSGSGTDFTLTISSVQPEDVATYFCQKYNNAPLTFGGGTKVEIK | 60 |
| ZIKV-19 heavy | QVQLVQSGPEVKKPGSSVKVSCKASGVSFNTYEISWVRQAPGQGLEWMGRIIPI FATPTYALKFQGRVTITTDESTTTGYMELSSLRSEDTAVYYCAGRPYGPGSWLPLD VWGQGTLVTVSS | 61 |
| ZIKV-19 light | DIVMTQSPSSLSASVGDRVTITCRASQGISSYLAWYQQKPGKLPKLLIYAASTLQS GVPSRFSGSGSGTDFTLTISSLQPEDVAAYYCQKYDSAPFTFGPGTKVDLK | 62 |
| ZIKV-27 heavy | QVQLVQSGPEVKKPGASVKVSCKASGFTSMNYGISWVRQAPGQGLEWMGWII AYNGNTNYAQKFQGRVSMTIDTSTTTAYMELRSLRSDDTAVYYCASRIEVADTVY DPWGQGTLVTVSS | 63 |
| ZIKV-27 light | EIVLTQSPGTLSLSPGERATLSCRASQTTSSSFLAWYQQKPGQAPRLLIYGASNRA TGIPDRFSGSGSGTDFTLTISKLEPEDFAVYYCQQYDSSPPGFTFGPGTKVDIK | 64 |
| ZIKV-33 heavy | QVQLVESGGAVVQPGRSLRLSCAASGLSFSDYAIHWVRQAPGKGLEWVAVIAH DGRNKYYADSVMGRVAISGDNSKNTVYLQMSSLRAEDTATYYCARGFYHDKTG SYWYFDLWGRGTLVTVSS | 65 |
| ZIKV-33 light | QSVLTQPPSVFAAAGQRVTISCSGSSSNIGDNYVSWYQQFPGTAPKILIYENDKR ASGIPDRFSGSKSGTSATLGITGLRTGDEADYFCGTWDSSLTTAVFGGGTKLTVL | 66 |
| ZIKV-46 heavy | EVQLVESGGGLVKPGGSLRLSCATSGFSVTNAWMSWVRQAPGRGLEWVGRIK NKADDWTTDYAAPVRGRFTISRDDSKDTVYLQMNSLKSEDTALYYCSTYYYDSSG HFVDYWGQGTLVTVSS | 67 |
| ZIKV-46 light | EIVLTQSPATLSLSAGDRATLSCRASQSVSIYLLWYQQKPGQAPRLLIYDASKRATG IPARFSGSGSGTDFTLTITSLEPEDFAVYYCLQRGIWPSFGQGTKVEIK | 68 |
| ZIKV-47 heavy | QVQLVESGGGVVQPGRSLRLSCAASGFTFTSYAFHWVRQAPGKGLEWVAVISY DGSQKFYADSVMDRFTISRDSSKNTQYLQMDSLRPEDTAVYYCATKGQSQIPVT AEYFEHWGRGTLVTVSS | 69 |
| ZIKV-47 light | QSVLTQPPSVSGAPGQRVTISCTGSSSNIGAGYDVHWYQQLPGTAPKLVIFANSN RPSGVPDRFSGSKSDTSASLAITGLQAEDEADYYCQSYDSSLSRYVVFGGGTKVTV L | 70 |
| ZIKV-48 heavy | QVQLVESGGGVVQPGRSLRLSCAASGFTFSSDAMHWVRQVPGKGLEWVAVTS YDGSNKYYADSVEGRFTISRDNSKNTLFLEMTSLRVEDSAIYYCARGFTVIHAFDI WGLGTLVTVSS | 71 |
| ZIKV-48 light | QSVLTQPRSVSGSLGQSVSISCTGTSSDVGGYNYVSWYLQHPGKAPKLIIYDVSKR PSGVPSRFSGSKSGNTASLTISGLQAEDEADYSCSSYAGTFVVFGGGTKLTVL | 72 |
| ZIKV-49 heavy | QVQLVESGPGLLKPSETLSLTCAVSGGSINSSSFHWGWIRQPPGKGLEWIGAIYYT GSTYYNPSLKSPVTVSVDTSKNQFSLELSSVTAADTAVYFCARVVATVTTRRGLGS FDIWGQGTLVTVSS | 73 |
| ZIKV-49 light | DIVMTQSPSSVSAFVGDRVTITCRASQGISNWLAWYQQKPGKAPKLLIYAASSLQ SGVPSRFSGSGSGTDFTLTISSLQPEDFATYYCQQANSFPWTFGQGTKVEIK | 74 |
| ZIKV-50 heavy | EVQLVESGGGLVQPGGSLRLSCAASGFTFSDPYMDWVRQAPGKGLEWVGRVR NKPNSYTTEYAASVTGRFTISRDDLKNSVYLQMNSLKTEDTAVYFCVRVALPKAF DVWGQGTLVTVSS | 75 |
| ZIKV-50 light | DIQMTQSPPSLSASVGDRVTITCQASQDISIYLNWFQHKPGKAPKLLIYDASNLET GVPSRFSGSGSGTDFSFTISGLQPEDVASYYCLQYDNPPTFGGGTKVEIK | 76 |
| ZIKV-70 heavy | QVQLVESGGGVVQPGGSLRLSCVGSGLTLSSYAMHWVRQAPGKGLEWVAVISS DGSNRYYADSVEDRFTISRDNSKNILYLQMNTLRPDDTAFYYCARGYYFDDSGSY WYFDLWGRGTLVTVSS | 77 |
| ZIKV-70 light | QSVLTQPPSVSAAPGQKVTISCSGSSSNIGNNYVSWYQQLPGAAPRVLIYEDSKR PSGIPDRFSGSKSGTSATLAITGLQTGDEADYYCATWDGGLSVIFGGGTQVTVL | 78 |

TABLE 2-continued

| PROTEIN SEQUENCES FOR ANTIBODY VARIABLE REGIONS | | |
|---|---|---|
| Clone | Variable Sequence | SEQ ID NO: |
| ZIKV-71 heavy | QVQLVQSGGEVKKPGASVKVSCKASGYSFINYGISWVRQAPGQGLEWMGYIIPY NGDTSYAQQFQGRVTMAADTSATTVFMEVGSLRLDDTAVYYCARAIVGETVTG YVYGMDVWGQGTLVTVSS | 79 |
| ZIKV-71 light | DIQLTQSPSSLSASVGDRVTITCRASQGIDIFLAWYQQKPGKAPNLLIYSASTLQSG VPSRFSGSGSGTFFTLTISSLQPEDFATYYCQYLNTSPWTFGQGTKVEIK | 80 |
| ZIKV-78 heavy | EVQLVESGGGLVKPGGSLRLSCEASEFTFSDYAMTWVRQPPGKGLEWVSTISGS GGGTFYADSVEDRFTISRENSENTLFLQMDNLRVEDTATYFCAVLFNSNENSPYY DASVFDIWGQGTLVTVSS | 81 |
| ZIKV-78 light | QAVVTQEPSLTVSPGGTVTFTCASSTGAVTSGHYPYWFQQKPGQAPRTLIYHSSK KHSWTPDRFSGSLLGGKAALTLSGAQPEDEAEYYCLLSYSGGRPVFGGGTQVTVL | 82 |
| ZIKV-81 heavy | QVQLVESGGGVVQPGRSLRLSCAASGFIFSNFAMHWVRQAPGKGLEWVAVISY DGSNTYYSDSVEGRFTISRDNSKNMLFLEVNTLRTEDTAVYYCAIGGGPPDFLAAP FNAEVLQHWGQGTLVTVSS | 83 |
| ZIKV-81 light | QSVLTQPPSVSGAPGQRVTISCTGSSSNIGAGYDIHWYQQLPGTAPKLLIYGNTN RPSGVPDRFSGSKSGTSGSLAITGLQAEDEADYFCQSYDTGLSVVFGGGTQVTVL | 84 |
| ZIKV-82 heavy | Not determined | 85 |
| ZIKV-82 light | DIQMTQSPSSVSASVGDTVTITCRASQDITYVLTWYQQKPGKAPKLLIYAAANLAS GVPSRFSGSGSGTHFTLTIRSLQPEDFATYYCQQANSFPWTFGQGTKVDIK | 86 |
| ZIKV-86 heavy | QVQLVESGGGVVQPGRSLRLSCAASGFTFSDYAMHWVRQAPGKGLEWVAVISY DINTKYYAESVEGRFSISRDDSINTVYLQMNSLRPDDTAVYFCARDVYGGGVPW GQGTLVTVSS | 87 |
| ZIKV-86 light | DIQMTQSPSTLSASVGDRVTITCRASQSVSDWLAWYQQKPGKAPKLLIYKASTLE SGVPSRFSGSGSGTEFTLTISSLQPDDFATYYCHQYSFYWTFGQGTKVDIK | 88 |
| ZIKV-88 heavy | QVQLLESGGGVVQPGRSLRLSCVASGLTFSTSAMHWVRQAPGKGLEWVAVISY DGSYKFYADSVRDQFTISRDNSKTTLYLQMDGLTPEDTAVYYCARGYNDDSSGSY WYFDLWGRGTLVTVSS | 89 |
| ZIKV-88 light | QSVLTQPPSVSAAPGQKVTMSCSGSSSNIGSNFVSWYQQLPGTAPKVLIFDNNQ RPSGIPDRFSGSKSGTSATLAITGLQPGDEAVYHCGTWDSSLTFAVFGGGTKLTVL | 90 |
| ZIKV-116 heavy | EVKLVESGRGLVRPGGSLRLSCAASGFTFSNYAMSWVRQGPGMGLEWVSTITA DSDSKYYVDSVKGRFTISRDNSKDTLFLHMTSLRAEDTAVYYCAKDRLSRGVGELY DSWGQGTLVTVSQ | 91 |
| ZIKV-116 light | DIQMTQSPSTLSASVGDRVTITCRASQSIDVWLAWYQQKPGKAPKLLMYKTSTL QTGVPSRFSGSGSGTEFTLTISSLQTDDFATYYCQKYDSYPWTFGPGTKVEIK | 92 |
| ZIKV-117 heavy | QVQLVESGGGVVRPGGSLRLSCAASGFTFKNYGIHWVRQAPGKGPEWVAFVRY DGNNKYYADSVKGRFTISRDNAKNTLSLQMNSLRVEDTAVYFCARDPETFGGFD YWGQGTLVTVSS | 93 |
| ZIKV-117 light | ETVMTQSPATLSVSPGERGTLSCRASESVSSNLAWYQQKPGKAPRLLIYGASTRA TGIPDRFSGSGSGTEFTLTISSLQSEDFAVYYCQQYYYSPRTFGQGTKVEVK | 94 |
| ZIKV-146 heavy | EVQLVESGGGLVQPGGSLRLSCVASGFTFSDYAMHWVRQAPGKGLEYVSTINSN GGNTFYANSVEDRFTISRDNSKSTLYLQLDSLRLEDTAVYYCVSLWNYPVLDYWG LGTLVTVSS | 95 |
| ZIKV-146 light | QAVVTQEPSLTVSPGGTVTLTCGSSTGAVTSGHYPYWFQQKPGQAPRTLIYHTN SKHSWTPARFSGSLLGGKAALTLSGAQPEDEAEYYCLLLYPDARVFGGGIRLTVL | 96 |
| ZIKV-158 heavy | QVQLVESGGGVVQPGRSLRLSCTSSGFTFNTYPMHWVRQAPGKGLEWLATISY VETDKYYTDSVQGRFTVSRDNSKNTLYLQMNSLSVEDTAVYYCARGWAVTTSHA FDVWGQGTLVTVSS | 97 |
| ZIKV-158 light | QSALTQPRSVSGSPGQSVTISCTGTSSDVGGYDFVSWYQEHPGKAPKLMIYDVT KRPSGVPDRFSGSKSGNTASLTISGLQAEDEADYYCCSYAGGYTFVVFGGGTQVT VL | 98 |
| ZIKV-165 heavy | QVQLVESGGGVVQPGGSLRLSCAASGFTFTNYGMHWVRQAPGKGLEWVAFIR PDGNDKYYADSVKGRFTISRDNSKNSLYLQMNSLGAEDTAVYYCAKDYYHTTDD YWAEFFQHWGQGTLVTVSS | 99 |

TABLE 2-continued

PROTEIN SEQUENCES FOR ANTIBODY VARIABLE REGIONS

| Clone | Variable Sequence | SEQ ID NO: |
|---|---|---|
| ZIKV-165 light | DIQMTQSPSTLSASVGDRVTITCRASQSINNWLAWYQQKPGKAPKLLIYMASNL ESGVPSRFSGSGSGTEFTLTISSLQPDDFASYYCQHYNFYPGFGQGTKVEIK | 100 |
| ZIKV-190 heavy | EVQLVESGGGLIQPGGSLRLSCAASGFTFSSYAMSWVRQAPGKGLEWVSAISGS GGSTYYADSVKGRFTISRDNSKNTLSLQMNSLRAEDTAVYYCARAFYYDFWTFDY WGQGTLVTVSS | 101 |
| ZIKV-190 light | QSALTQPRSVSGSPGQSVTISCTGTSSDVGGYNYVSWYQQHPGKAPKLMIYAVT KRPSGVPDRFSGSKSGNTASLTISGLQAEDEADYYCCSYAGSYTYVVFGGGTKLTV L | 102 |
| ZIKV-195 heavy | QVQVVESGGGVVQPGRSLRLSCAASGFTFSSSAMHWVRQAPGKGLEWVAVISY DGSNKYYGDSVKGRFTISRDNSKNTLYLQMHSLRAEDTAVYYCAKDRDAYNTVG YFAYYYGMDVWGQGTLVTVSS | 103 |
| ZIKV-195 light | QSVLTQPPSVSEAPRQRVTISCSGSSSNIGNNAVNWYQQLPGKAPKLLIYYDDLLP SGVSDRFSGSKSGTSASLAISGLQSEDEADYYCAAWDDSLTRYVFGTGTKVTVL | 104 |
| ZIKV-204 heavy | QVTLRESGPALLKPTQTLTLTCTFSGFSLSTNETCVSWIRQPPGKALEWLALIDWD DDQYSSTSLAARLTVSKDTSKNQVVLTMTNVAPVDTATYYCALTRPTLTAQNGD KYYNYYYGMDVWGQGTLVTVSS | 105 |
| ZIKV-204 light | EIVLTQSPGTLSLSPGERATLSCRASQSVSSMYLAWYQQKRGQPPRLLIYGTFNRA TGIPDRFSGSGSGTDFTLTISRLEPEDFAVYYCQQYGSSSFTFGGGTKVEIK | 106 |
| ZIKV-216 heavy | EVQLVQSGAEGKKPGESLKISCKGSGYNFSNYWIGWVRQMPGKGLEWMGIIYP GDSDTRYSPSFQGQVTISADKSINTAYLQWRSLRASDSAMFYCARGVMITTPNPY DWFDAWGQGTLVTVSS | 107 |
| ZIKV-216 light | QSALTQPASVSGSPGQSITISCTGTGSDIGTYDYVSWYQQHPGKAPKLMIYGVTK RPSGVSHRFSGSKSVNTASLTISGLQAEDEADYFCSSYSTSSTFVVFGGGTKLTVL | 108 |
| ZIKV-218 heavy | QVQLVESGGGVVQPGRSLRLSCAASGFTFSGHALHWVRQAPGKGLQWVAVISS DATSKFYADSVEGRFSISRDNPKNTLFLQLDSLGREDSGIYYCVLGFTSSWDLTAYA FDYWGQGTLVTVSS | 109 |
| ZIKV-218 light | QSALTQPHSVSGSPRQSVTISCVGTSDDVGAYSSVSWYQQHPGKAPKLLVYDVA ERPSGVPDRFSGSNSGNTASLTISGLQSDDEATYYCCAYAGTYVVFGGGNKVTVL | 110 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| ZIKV-2 | GFTLSTFA (119) | TSYDGSSK (120) | ARGFGGSGDYYVGGFDI (121) |
| ZIKV-8 | GFTFSNYA (122) | ISYDGSYT (123) | ARDALGYYDNSDYTS (124) |
| ZIKV-12 ZIKV-12 | GFTFSDYA (125) | INSNGGST (126) | VSLYNYPVLDY (127) |
| ZIKV-15 | GFTFSTHD (128) | IRFGGKDI (129) | AKGARFYDSNGFPVYAEYFEH (130) |
| ZIKV-19 | GVSFNTYE (131) | IIPIFATP (132) | AGRPYGPGSWLPLDV (133) |
| ZIKV-27 | GFTSMNYG (134) | IIAYNGNT (135) | ASRIEVADTVYDP (136) |
| ZIKV-33 | GLSFSDYA (137) | IAHDGRNK (138) | ARGFYHDKTGSYWYFDL (139) |
| ZIKV-46 | GFSVTNAW (140) | IKNKADDWTT (141) | STYYYDSSGHFVDY (142) |

TABLE 3-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| ZIKV-47 | GFTFTSYA (143) | ISYDGSQK (144) | ATKGQSQIPVTAEYFEH (145) |
| ZIKV-48 | GFTFSSDA (146) | TSYDGSNK (147) | ARGFTVIHAFDI (148) |
| ZIKV-49 | GGSINSSSFH (149) | IYYTGST (150) | ARVVATVTTRRGLGSFDI (151) |
| ZIKV-50 | GFTFSDPY (152) | VRNKPNSYTT (153) | VRVALPKAFDV (154) |
| ZIKV-55 | GYTFTSFG (155) | NSAWISAH (156) | VYYCARVGGWQQIPYFDF (157) |
| ZIKV-70 | GLTLSSYA (158) | ISSDGSNR (159) | ARGYYFDDSGSYWYFDL (160) |
| ZIKV-71 | GYSFINYG (161) | IIPYNGDT (162) | ARAIVGETVTGYVYGMDV (163) |

TABLE 3-continued

| CDR HEAVY CHAIN SEQUENCES | | | |
|---|---|---|---|
| Anti-body | CDRH1 (SEQ ID NO:) | CDRH2 (SEQ ID NO:) | CDRH3 (SEQ ID NO:) |
| ZIKV-78 | EFTFSDYA (164) | ISGSGGGT (165) | AVLFNSNENSPYYDASVFDI (166) |
| ZIKV-81 | GFIFSNFA (167) | ISYDGSNT (168) | AIGGGPPDFLAAPFNAEVLQH (169) |
| ZIKV-82 | Not determined | Not determined | Not determined |
| ZIKV-86 | GFTFSDYA (171) | ISYDINTK (172) | ARDVYGGGVP (173) |
| | (180) | (181) | (182) |
| ZIKV-15 | GFTFSTHD (183) | IRFGGKDI (184) | AKGARFYDSNGFPVYAEYFEH (185) |
| ZIKV-19 | GVSFNTYE (186) | IIPIFATP (187) | AGRPYGPGSWLPLDV (188) |
| ZIKV-27 | GFTSMNYG (189) | IIAYNGNT (190) | ASRIEVADTVYDP (191) |
| ZIKV-33 | GLSFSDYA (192) | IAHDGRNK (193) | ARGFYHDKTGSYWYFDL (194) |
| ZIKV-46 | GFSVTNAW (195) | IKNKADDWTT (196) | STYYYDSSGHFVDY (197) |
| ZIKV-47 | GFTFTSYA (198) | ISYDGSQK (199) | ATKGQSQIPVTAEYFEH (200) |
| ZIKV-48 | GFTFSSDA (201) | TSYDGSNK (202) | ARGFTVIHAFDI (203) |
| ZIKV-49 | GGSINSSSFH (204) | IYYTGST (205) | ARVVATVTTRRGLGSFDI (206) |
| ZIKV-50 | GFTFSDPY (207) | VRNKPNSYTT (208) | VRVALPKAFDV (209) |
| ZIKV-55 | GYTFTSFG (210) | NSAWISAH (211) | VYYCARVGGWQQIPYFDF (212) |
| ZIKV-70 | GLTLSSYA (213) | ISSDGSNR (214) | ARGYYFDDSGSYWYFDL (215) |
| ZIKV-71 | GYSFINYG (216) | IIPYNGDT (217) | ARAIVGETVTGYVYGMDV (218) |
| ZIKV-78 | EFTFSDYA (219) | ISGSGGGT (220) | AVLFNSNENSPYYDASVFDI (221) |
| ZIKV-81 | GFIFSNFA (222) | ISYDGSNT (223) | AIGGGPPDFLAAPFNAEVLQH (224) |
| ZIKV-82 | Not determined | Not determined | Not determined |
| ZIKV-86 | GFTFSDYA (225) | ISYDINTK (226) | ARDVYGGGVP (227) |

TABLE 4

| CDR LIGHT CHAIN SEQUENCES | | | |
|---|---|---|---|
| Anti-body | CDRH1 (SEQ ID NO:) | CDRH2 | CDRH3 (SEQ ID NO:) |
| ZIKV-2 | SSDVGGYDY (228) | DVN | CSFAGSHSFVL (229) |
| ZIKV-8 | QTITSSH (230) | DAS | QQYATPPWT (231) |
| ZIKV-12 | TGAVTSGHY (232) | HTN | LILYPDARV (233) |
| ZIKV-15 | QDISNF (234) | AAS | QKYNNAPLT (235) |
| ZIKV-19 | QGISSY (236) | AAS | QKYDSAPFT (237) |
| ZIKV-27 | QTTSSSF (238) | GAS | QQYDSSPPGFT (239) |
| ZIKV-33 | SSNIGDNY (240) | END | GTWDSSLTTAV (241) |
| ZIKV-46 | QSVSIY (242) | DAS | LQRGIWPS (243) |
| ZIKV-47 | SSNIGAGYD (244) | ANS | QSYDSSLSRYVV (245) |
| ZIKV-48 | SSDVGGYNY (246) | DVS | SSYAGTFVV (247) |
| ZIKV-49 | QGISNW (248) | AAS | QQANSFPWT (249) |
| ZIKV-50 | QDISIY (250) | DAS | LQYDNPPT (251) |
| ZIKV-55 | EGPDSY (252) | AAS | QHLNGYPS (253) |
| ZIKV-70 | SSNIGNNY (254) | EDS | ATWDGGLSVI (255) |
| ZIKV-71 | QGIDIF (256) | SAS | QYLNTSPWT (257) |
| ZIKV-78 | TGAVTSGHY (258) | HSS | LLSYSGGRPV (259) |
| ZIKV-81 | SSNIGAGYD (260) | GNT | QSYDTGLSVV (261) |
| ZIKV-82 | QDITYV (262) | AAA | QQANSFPWT (263) |
| ZIKV-86 | QSVSDW (264) | KAS | HQYSFYWT (265) |

TABLE 5

| Research Subjects with Time and Place of Infection | | | |
|---|---|---|---|
| ZIKV strain | Subject | Year infected | Country in which infection occurred |
| African | 972 | 2008 | Senegal |
| | 973 | 2008 | Sexual transmission from Subject 972* |
| Asian | 1001 | 2015 | Brazil |
| | 1002 | 2016 | Mexico |
| | 1010 | 2016 | Haiti |
| | 1011 | 2016 | Haiti |

TABLE 5-continued

| Research Subjects with Time and Place of Infection | | | |
|---|---|---|---|
| ZIKV strain | Subject | Year infected | Country in which infection occurred |
| | 1012 | 2016 | Haiti |
| | 1016 | 2016 | Haiti |

*Case was reported previously:

Foy B D, Kobylinski K C, Chilson Foy J L, Blitvich B J, Travassos da Rosa A, Haddow A D, Lanciotti R S, Tesh R B. Probable non-vector-borne transmission of Zika virus, Colorado, USA. *Emerg Infect Dis*. 2011; 17: 880-2.

Example 3—Discussion

These studies reveal a number of features of humoral immunity to ZIKV. First, following infection, a subset of human B cells encode mAbs that neutralize ZIKV in vitro with high potency, the most potent with FRNT50 values <10 ng/ml. Second, the human B cell response is directed against multiple antigenic sites on ZIKV E protein, predominantly against the fusion loop in DII, and other structural features in DII and DIII, results that agree with a recent study 10. The most inhibitory antibodies recognized antigenic sites in DIII (lateral ridge) and in DII at a unique site not reported to be targeted by DENY antibodies, located at the dimer-dimer interface of the E protein. The most potent neutralizing antibodies exhibited a breadth of inhibitory activity against strains from Africa, Asia, and the Americas. Treatment of ZIKV-infected male mice with mAb ZIKV-117 showed strong post-exposure therapeutic activity in vivo. Even a single ZIKV-117 dose given five days after infection protected against lethal ZIKV infection, a timeline that was similar to the most protective antibodies reported against other flaviviruses (Oliphant et al., 2005). Prophylaxis or post-exposure therapy of pregnant mice with ZIKV-117 reduced infection in the mothers, and in placental and fetal tissues. To the inventors' knowledge, this is the first evidence showing that an antiviral agent can prevent or control ZIKV infection in pregnancy. Accordingly, ZIKV-117 or human antibodies with similar profiles, could be developed as a preventive or treatment measure during pregnancy for at-risk humans. By defining key epitopes on the E protein associated with antibody-mediated protection, these studies also inform vaccine efforts to design new epitope-based immunogens that elicit highly protective antibody responses against ZIKV.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, N.Y., 1988.
Abbondanzo et al., *Am. J. Pediatr. Hematol. Oncol.,* 12(4), 480-489, 1990.
Allred et al., *Arch. Surg.,* 125(1), 107-113, 1990.
Araujo et al., *Brain* 139, 2122-2130, 2016.
Atherton et al., *Biol. of Reproduction,* 32, 155-171, 1985.
Austin et al., PLoS Pathog 8, e1002930, 2012.
Beltramello et al., *Cell Host Microbe* 8, 271-283, 2010.
Brehin, et al., Virology 371:185-195, 2008.
Brochet et al., *Nucleic Acids Res.* 36, W503-8, 2008.
Brown et al., *J. Immunol. Meth.,* 12;130(1), 111-121, 1990.
Campbell, *In: Monoclonal Antibody Technology, Laboratory Techniques in Biochemistry and Molecular Biology,* Vol. 13, Burden and Von Knippenberg, Eds. pp. 75-83, Amsterdam, Elsevier, 1984.
Capaldi et al., *Biochem. Biophys. Res. Comm.,* 74(2):425-433, 1977.
Charles, A. S. & Christofferson, R. C., *PLoS Curr.* 8, 1-31, 2016.
Christian et al., *Proc Natl Acad Sci USA,* 110:18662-18667, 2013.
Couderc et al., *J. Infect. Dis.* 200, 516-523, 2009.
Coyne et al., *Nat. Rev. Microbiol.* 1-9, 2016.
Davidson, E. & Doranz, B. J., *Immunology* 143, 13-20, 2014.
De Jager et al., *Semin. Nucl. Med.* 23(2), 165-179, 1993.
Dejnirattisai et al., *Nat. Immunol.* 1-8, 2016.
Dholakia et al., *J. Biol. Chem.,* 264, 20638-20642, 1989.
Doolittle and Ben-Zeev, *Methods Mol. Biol.,* 109, 215-237, 1999.
Duffy et al., *N. Engl. J. Med.* 360, 2536-2543, 2009.
Edwards & Brown, *J. Gen. Virol.* 67 (Pt 2), 377-380, 1986.
Edwards et al., *J. Gen. Virol.* 67 (Pt 2), 377-380, 1986.
Fong et al., *J. Virol.* 88:14364-14379, 2014.
Foy et al., *Emerg. Infect. Dis.* 17, 880-882, 2011.
Fric et al., *J. Infect. Dis.* 207:319-322, 2013.
Gatherer, D. & Kohl, A., *J. Gen. Virol.* 97, 269-73, 2016.
Gefter et al., *Somatic Cell Genet.,* 3:231-236, 1977.
Gibson et al., *Nat. Methods* 6, 343-5, 2009.
Goh et al., *Clin. Immunol.* 149:487-497, 2013.
Giudicelli, V. & Lefranc, M. P., *Cold Spring Harb. Protoc.* 6, 716-725, 2011.
Gulbis and Galand, *Hum. Pathol.* 24(12), 1271-1285, 1993.
Guo et al., *Sci. Transl. Med.* 3:99 ra85, 2001.
Hallengard, et al., *J. Virol.* 88:13333-13343, 2014.
Hawman et al., *J. Virol.* 87, 13878-13888, 2013.
Hessell et al., *Nature* 449, 101-4, 2007.
Hong et al., *J. Virol.* 87:12471-12480, 2013.
Kam et al., *EMBO Mol. Med.* 4, 330-343, 2012b.
Kam et al., *J. Virol.* 86, 13005-13015, 2012a.
Kam et al., *PLoS One* 9, e95647, 2014.
Khatoon et al., *Ann. of Neurology,* 26, 210-219, 1989.
Kielian et al., *Viruses* 2:796-825, 2010.
Kim. et al., *J. Immunol.* 182, 2583-9, 2009.
King et al., *J. Biol. Chem.,* 269, 10210-10218, 1989.
Kohler and Milstein, *Eur. J. Immunol.,* 6, 511-519, 1976.
Kohler and Milstein, *Nature,* 256, 495-497, 1975.
Krause et al., *J. Immunol.* 187:3704-3711, 2011b.
Krause et al., *J. Virol.* 84:3127-3130, 2010.
Krause et al., *J. Virol.* 85:10905-10908, 2011a.
Krause et al., *J. Virol.* 86:6334-6340, 2012.
Kyte and Doolittle, *J. Mol. Biol.,* 157(1):105-132, 1982.
Lanciotti & Valadere, *Emerg Infect Dis* 20, 2014.
Lanciotti et al., *Emerg. Infect. Dis.* 14, 1232-1239, 2008.
Lee et al., *PLoS Pathog.* 7:e1002390, 2011.
Levitt et al., *Vaccine* 4, 157-162, 1986.

Lum et al., *J. Immunol.* 190:6295-6302, 2013.
Mainou et al., *MBio* 4, 2013.
Masrinoul et al., *Virology* 464-465, 111-117, 2014.
Messer et al., *Proc. Natl. Acad. Sci. USA* 111:1939-1944, 2014.
Miner et al., *Cell* 165, 1081-91, 2016.
Morens, D. M., *Clin. Infect. Dis.* 19, 500-512, 1994.
Morrison et al., *Am J Pathol,* 178:32-40, 2011.
Musso et al., *Clin. Microbiol. Infect.* 20, 0595-0596, 2014.
Mysorekar, I. U. & Diamond, M. S., *N Engl. J. Med.* 375, 481-4, 2016.
Nakamura et al., *In: Enzyme Immunoassays: Heterogeneous and Homogeneous Systems*, Chapter 27, 1987.
Nelson et al., *Methods Mol. Biol.* 1140, 145-57, 2014.
Oehler et al., *Euro Surveill. Bull. Eur. sur les Mal. Transm.=Eur. Commun. Dis. Bull.* 19, 7-9, 2014.
Oliphant et al., *Nat. Med.* 11, 522-30, 2005.
O'Shannessy et al., *J. Immun. Meth.,* 99, 153-161, 1987.
Paes et al., *J. Am. Chem. Soc.,* 131:6952-6954, 2009.
Pal et al., *J. Virol.* 88:8213-8226, 2014.
Pal et al., *PLoS Pathog* 9, e1003312, 2013.
Pentsuk, N. & van der Laan, J. W., *Birth Defects Res. B. Dev. Reprod. Toxicol.* 86, 328-44, 2009.
Persic et al., *Gene* 187:1, 1997
Potter and Haley, *Meth. Enzymol.,* 91, 613-633, 1983.
Remington's Pharmaceutical Sciences, 15th Ed., 3:624-652, 1990.
R. C. Team, R Foundation for Statistical Computing, Vienna, Austria, 2014.
Schilte et al., *PLoS Negl. Trop. Dis.* 7:e2137, 2013.
Screaton et al., *Nat. Publ. Gr.* 15, 745-759, 2015.
Selvarajah et al., *PLoS Negl. Trop. Dis.* 7:e2423, 2013.
Sissoko et al., *PLoS Negl. Trop. Dis.* 3:e389, 2009.
Smith et al., *J. Virol.* 86, 2665-2675, 2012.
Smith et al., *J. Virol.* 88, 12233-12241, 2014.
Smith et al., *J. Virol.* 86:2665-2675, 2012.
Smith et al., *MBio* 4, e00873-00813, 2013a.
Smith et al., *J. Infect. Dis.* 207, 1898-1908, 2013b.
Staples et al., *Clin. Infect. Dis.* 49, 942-948, 2009.
Stettler et al., *Science* 353, 823-6, 2016.
Sun et al., *Elife* 2:e00435, 2013.
Sun et al., *J. Steroid Biochem.,* 26(1):83-92, 1987.
Sun et al., *J. Virol.* 88:2035-2046, 2014.
Swanstrom et al., *MBio* 7, e01123-16, 2016.
Tang et al., *J. Biol. Chem.,* 271:28324-28330, 1996.
Thornburg et al., *J. Clin. Invest.* 123, 4405-9, 2013.
Thornburg et al., *J. Clin. Invest.* 126, 1482-1494, 2016.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
Vander Veen et al., *Anim Health Res Rev,* 13:1-9, 2012.
Voss et al., *Nature,* 468:709-712, 2010.
Voss et al., *Nature,* 468:709-712, 2010.
Warter et al., *J. Immunol.,* 186:3258-3264, 2011.
Warter et al., *J. Immunol.,* 186:3258-3264, 2011.
Wawrzynczak & Thorpe, In: *Immunoconjugates, Antibody Conuugates In Radioimaging And Therapy Of Cancer*, Vogel (Ed.), NY, Oxford University Press, 28, 1987.
Williams et al., *PLoS Pathog.* 9, 2013.
Yockey et al., *Cell* 166, 1247-1256.e4, 2016.
Yu et al., *J Immunol. Methods* 336, 142-51, 2008a.
Zhao et al., *Cell* 166, 1016-1027, 2016.
Purpura et al., *Lancet Infect Dis.* 2016 October;16(10):1107-8. Epub 2016 Sep. 19.
Mansuy et al., *Lancet Infect Dis.* 2016 October;16(10):1106-7.
Barzon et al., *Euro Surveill.* 2016 Aug. 11;21(32).
Gornet et al., *Semin Reprod Med.* 2016 September;34(5):285-292. Epub 2016 Sep. 14.
Duffy et al., *N Engl J Med* 2009; 360 (24) 2536-2543
Center for Disease Control. Zika virus. Atlanta, Ga.: US Department of Health and Human Services, CDC; 2016.
Halfon et al., *PLoS ONE* 2010; 5 (5) e10569
Elder et al. Infections, infertility and assisted reproduction. Part II: Infections in reproductive medicine & Part III: Infections and the assisted reproductive laboratory. Cambridge UK: Cambridge University Press; 2005.

What is claimed is:

1. A method of detecting a Zika virus infection in a subject comprising:

(a) contacting a sample from said subject with an antibody or antigen binding fragment thereof having heavy chain CDR1 as GFTFKNYG (SEQ ID NO: 266), heavy chain CDR2 as VRYDGNNK (SEQ ID NO: 267), and heavy chain CDR3 as ARDPETFGGFDY (SEQ ID NO: 268), and light chain CDR1 as ESVSSN (SEQ ID NO: 269), light chain CDR2 as GAS, and light chain CDR3 as QQYYYSPRT (SEQ ID NO: 270); and (b) detecting Zika virus in said sample by binding of said antibody or antibody fragment to a Zika virus antigen in said sample.

2. A method of treating a subject infected with Zika virus or reducing the likelihood of infection of a subject at risk of contracting Zika virus, comprising delivering to said subject an effective amount of an antibody or antigen binding fragment thereof having heavy chain CDR1 as GFTFKNYG (SEQ ID NO: 266), heavy chain CDR2 as VRYDGNNK (SEQ ID NO: 267), and heavy chain CDR3 as ARDPETFGGFDY (SEQ ID NO: 268), and light chain CDR1 as ESVSSN (SEQ ID NO: 269), light chain CDR2 as GAS, and light chain CDR3 as QQYYYSPRT (SEQ ID NO: 270).

3. The method of claim 2, the antibody or antigen binding fragment thereof is encoded by clone-paired light and heavy chain variable sequences of SEQ ID NO: 44 and SEQ ID NO. 43, respectively.

4. The method of claim 2, the antibody or antigen binding fragment thereof is encoded by clone-paired light and heavy chain variable sequences having 95% identity to SEQ ID NO: 44 and SEQ ID NO. 43, respectively.

5. The method of claim 2, wherein said antibody or antigen binding fragment thereof is encoded by light and heavy chain variable sequences having 70%, 80%, or 90% identity to SEQ ID NO: 44 and SEQ ID NO. 43, respectively.

6. The method of claim 2, wherein said antibody or antigen binding fragment thereof comprises light and heavy chain variable sequences according to clone-paired sequences of SEQ ID NO: 94 and SEQ ID NO. 93, respectively.

7. The method of claim 2, wherein said antibody or antigen binding fragment thereof comprises light and heavy chain variable sequences having 70%, 80% or 90% identity to clone-paired sequences of SEQ ID NO: 94 and SEQ ID NO. 93, respectively.

8. The method of claim 2, wherein said antibody or antigen binding fragment thereof comprises light and heavy chain variable sequences having 95% identity to clone-paired sequences of SEQ ID NO: 94 and SEQ ID NO. 93, respectively.

9. The method of claim 2, wherein the antigen binding fragment thereof is a recombinant scFv (single chain fragment variable) antibody, Fab fragment, $F(ab')_2$ fragment, or Fv fragment.

10. The method of claim 2, wherein said antibody is an IgG, or a recombinant IgG antibody or antigen binding fragment thereof comprising an Fc portion mutated to eliminate FcR interactions, such as a LALA mutation or a LS mutation.

11. The method of claim 2, wherein said antibody is a chimeric antibody or a bispecific antibody.

12. The method of claim 2, wherein said antibody or antigen binding fragment thereof is administered prior to infection or after infection.

13. The method of claim 2, wherein said subject is a pregnant female, a sexually active female, or a female undergoing fertility treatments.

14. The method of claim 2, wherein delivering comprises antibody or antigen binding fragment thereof administration, or genetic delivery with an RNA or DNA sequence or vector encoding the antibody or antibody fragment.

15. A hybridoma or engineered cell encoding an antibody or antigen binding fragment thereof wherein the antibody or antigen binding fragment thereof comprises the heavy chain CDR1 as GFTFKNYG (SEQ ID NO: 266), heavy chain CDR2 as VRYDGNNK (SEQ ID NO: 267), and heavy chain CDR3 as ARDPETFGGFDY (SEQ ID NO: 268), and light chain CDR1 as ESVSSN (SEQ ID NO: 269), light chain CDR2 as GAS, and light chain CDR3 as QQYYYSPRT (SEQ ID NO: 270).

16. A formulation comprising one or more antibodies or antigen binding fragments thereof comprises the heavy chain CDR1 as GFTFKNYG (SEQ ID NO: 266), heavy chain CDR2 as VRYDGNNK (SEQ ID NP: 267), and heavy chain CDR3 as ARDPETFGGFDY (SEQ ID NP: 268), and light chain CDR1 as ESVSSN (SEQ ID NO: 269), light chain CDR2 as GAS, and light chain CDR3 as QQYYYSPRT (SEQ ID NO: 270), wherein the antibodies or antigen binding fragments thereof are conjugated to an effector molecule selected from the group consisting of: toxins, anti-tumor agents, therapeutic enzymes, radionuclides, antiviral agents, chelating agents, cytokines, growth factors, oligonucleotide or polynucleotides; or the antibodies or antigen binding fragments thereof are conjugated to a reporter molecule selected from the group consisting of: enzymes, radiolabels, haptens, fluorescent labels, phosphorescent molecules, chemiluminescent molecules, chromophores, photoaffinity molecules, colored particles or ligands.

17. A method of protecting the health of a placenta and/or fetus of a pregnant a subject infected with or at risk of infection with Zika virus comprising delivering to said subject an effective amount of an antibody or antigen binding fragment thereof having heavy chain CDR1 as GFTFKNYG (SEQ ID NO: 266), heavy chain CDR2 as VRYDGNNK (SEQ ID NO: 267), and heavy chain CDR3 as ARDPETFGGFDY (SEQ ID NO: 268), and light chain CDR1 as ESVSSN (SEQ ID NO: 269), light chain CDR2 as GAS, and light chain CDR3 as QQYYYSPRT (SEQ ID NO: 270).

18. The method of claim 17, wherein said subject is a pregnant female, a sexually active female, or a female undergoing fertility treatments.

19. The method of claim 17, wherein the antibody or antigen binding fragment thereof increases the size of the placenta as compared to an untreated control.

20. The method of claim 17, wherein the antibody or antigen binding fragment thereof reduces viral load and/or pathology of the fetus as compared to an untreated control.

* * * * *

SEQUENCE LISTING

```
<160> NUMBER OF SEQ ID NOS: 270

<210> SEQ ID NO 1
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 1

caggtgcagc tggtggagtc tgggggaggc gtggtccagc ctgggaggtc cctgagactc      60

tcctgtgcag cctctggatt caccctcagt acttttgcta tgcactgggt ccgccaggct     120

ccaggcaagg ggctgcagtg ggtggctgtt acatcatatg atggaagcag taaattctac     180
```

```
gcagactccg tggagggccg attcaccatc tccagagaca cgtccaagaa cacgttgtat    240

ctgcaaatga ccagcctgac agctgaggac acggctgtgt atttctgtgc gagaggcttc    300

ggcggtagtg gtgattacta cgtaggggga tttgatatct ggggccaagg gaccctggtc    360

accgtctcct ca                                                        372


<210> SEQ ID NO 2
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 2

cagtctgccc tgactcagcc tcgctcagtg tccgggtctc ctggacagtc agtcaccatc     60

tcctgcactg gaaccagcag tgatgttggt ggttatgact atgtctcctg gtaccaacag    120

cacccaaccg aagcccccaa actcatcatt catgatgtca ataagcggcc ctcaggggtc    180

cctgatcgct tctctggctc caagtctggc aacacggcct ccctgaccat ctctgggctc    240

caggctgaag atgaggctga ttattactgc tgctcttttg caggcagcca cagttttgtt    300

ttattcggcg gagggaccag gctgaccgtc cta                                 333


<210> SEQ ID NO 3
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 3

caggtgcagc tggtggagtc cgggggacgc gtggtccagc ctgggaggtc cctgaggctc     60

tcctgtgcgg cctctggatt caccttcagt aattatgcca tgcactgggt ccgccaggct    120

ccaggcaagg ggctggagtg ggtggctgtt atctcatacg atggaagtta tacacattac    180

acagaggccg tgagggaccg attcaccatc tccagagaca attccaagag gacggtgtgg    240

ctggaaatga acagtctgag agtcgacgac acggctatgt attactgtgc gagagatgcg    300

cttggatact atgataattc tgattatact tcttggggcc tggggaccct ggtcaccgtc    360

tcctca                                                               366


<210> SEQ ID NO 4
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 4

gaaattgtgt tgacgcagtc tccagacacc ctgtctttgg ctccagggga aagagccacc     60

ctctcgtgca gggccgggca gactattacc agcagccact tagcctggta ccggctaaaa    120

cccggccagg ctcccagact catcatctat gatgcatcca gcagggccac tggcatccca    180

gacaggttca gtggcagtgg gtctgggaca cagttcactc tcaccatcag cagactggag    240

cctgaagatt ttgcagtata ttactgtcag cagtatgcta ccccaccgtg gacgttcggc    300

caagggacca aggtggagat caaa                                           324


<210> SEQ ID NO 5
<211> LENGTH: 354
```

<212> TYPE: DNA
<213> ORGANISM: Artificial sequence
<220> FEATURE:
<223> OTHER INFORMATION: Synthetic oligonucleotide

<400> SEQUENCE: 5

```
gaggtgcagc tggtggagtc tgggggaggc ttggtccagc ctgggggggtc cctgagactc     60

tcctgtgtag cctctggatt caccttcagc gattatgcta tgcactgggt ccgccaggct    120

ccagggaagg gactggaata tgtttcaacc attaatagta atgggggtag cacattttat    180

gcggactctg tgcaggacag attcaccatc tccagagaca attccaagaa cacgctttat    240

cttcaaatgg acagcctgag acctgaggac atggctgtct attattgtgt gagtctgtac    300

aactatccag tcttagacta ctggggcctg ggaaccctgg tcaccgtctc ctca          354
```

<210> SEQ ID NO 6
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 6

```
caggctgtgg tgactcagga gacctcactg actgtgtccc caggagggac agtcactctc     60

acctgtggct ccagcactgg agctgtcacc agtggtcatt atccctactg gttccagcag    120

aagcctggcc aagcgcccag gacactgatt tatcatacaa acaacaaaca ctcctggaca    180

cctgcccggt tctcaggctc cctccttggg ggcaaagctg ccctgaccct ttcgggtgcg    240

caccccgacg atgaagctga atactactgt ttgatcttgt atcctgatgc tcgcgtcttt    300

ggcggaggga ccaagctgac cgtccta                                        327
```

<210> SEQ ID NO 7
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 7

```
caggtgcagc tggtggagtc tgggggaggc gtggtccagc ctgggggggtc cctgagactc     60

tcctgtgcag cgtctggatt caccttcagc acccatgaca tgcactgggt ccgccaggct    120

ccaggcaagg ggctggagtg ggtggcactt atacggtttg gtggcaaaga tatatactat    180

gcagactccg tggagggccg attcaccgtc tccagagaca attccatgaa cacgctctat    240

ctgcaactga gcggcctgag agctgatgac acggctctgt actactgtgc gaaaggcgcc    300

cgattctatg attctaatgg tttccccgtt tacgctgaat acttcgaaca ctggggccag    360

ggcaccctgg tcaccgtctc ctca                                           384
```

<210> SEQ ID NO 8
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 8

```
gacatccaga tgacccagtc tccatcctcc ctgtctgcat ctgtaggaga cagagtcacc     60

atcacttgcc gggcgagtca ggacatcagc aatttttag cctggtatca gcagagacca    120
```

gggaaagttc ctaaactctt gatctatgct gcatccacct tgcaatctgg ggtcccatct 180
cggttcagtg gcagtgggtc tgggacagat ttcactctca ccatcagcag cgtgcagcct 240
gaagatgttg caacttattt ctgtcaaaag tataacaatg ccccgctcac attcggcgga 300
gggaccaagg tagagatcaa a 321

<210> SEQ ID NO 9
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 9
caggtgcagc tggtgcagtc agggcctgag gtgaagaagc cggggtcctc ggtgaaggtc 60
tcctgcaagg cttctggagt cagcttcaac acctatgaga tcagctgggt gcgacaggcc 120
cctggacaag ggcttgagtg gatgggaagg atcatcccta tctttgctac accaacctac 180
gcactgaagt tccagggcag agtcacgatt accacggacg aatccacgac cacaggttac 240
atggagctga gcagcctgag atctgaggac acggccgtgt attactgtgc gggaaggccc 300
tatggtccgg ggagttggtt gcccctggac gtctggggcc aagggaccct ggtcaccgtc 360
tcctca 366

<210> SEQ ID NO 10
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 10
gacattgtga tgacccagtc tccatcctcc ctgtctgcat ctgtaggaga cagagtcacc 60
atcacttgcc gggcgagtca gggcattagc tcttatttgg cctggtatca gcaaaaacca 120
gggaaacttc ctaagctcct gatctatgct gcatccactt tgcaatcagg ggtcccatct 180
cggttcagcg gcagtggatc tgggacagat ttcactctca ccatcagcag cctgcagcct 240
gaagacgttg cagcttatta ctgtcaaaag tatgacagtg ccccattcac tttcggccct 300
gggaccaaag tggatctcaa a 321

<210> SEQ ID NO 11
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 11
caggtgcagc tggtgcagtc tggacctgag gtgaagaaac ctggggcctc agtgaaggtc 60
tcctgcaagg cttctggttt cacctctatg aattatggta tcagctgggt gcgacaggcc 120
cctggacaag ggcttgagtg gatgggatgg ataatcgctt acaatggaaa cacaaactat 180
gcacagaagt tccagggcag agtctccatg accatagaca catccacgac cactgcctac 240
atggaactga ggagcctgag atctgacgac acggccgtat attactgtgc gagccgaata 300
gaagtggctg atacggtcta cgacccctgg ggccagggaa ccctggtcac cgtctcctca 360

<210> SEQ ID NO 12
<211> LENGTH: 330

<212> TYPE: DNA
<213> ORGANISM: Artificial sequence
<220> FEATURE:
<223> OTHER INFORMATION: Synthetic oligonucleotide

<400> SEQUENCE: 12
gaaattgtgt tgactcagtc tccaggcacc ctgtctttgt ctccagggga aagagccacc 60
ctctcgtgca gggccagtca gactactagc agcagcttct tagcctggta ccagcagaag 120
cctggccagg ctcccaggct cctcatctat ggtgcatcca acagggccac tggcatccca 180
gacaggttca gtggcagtgg gtctgggaca gacttcactc tcactatcag caaactggag 240
cctgaagatt ttgcggtcta ttactgtcag cagtatgaca gctcacctcc gggattcact 300
ttcggccctg ggaccaaagt ggatatcaaa 330

<210> SEQ ID NO 13
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 13
caggtgcagc tggtggagtc tgggggagct gtggtccagc ctgggaggtc cctgagactc 60
tcctgtgcag cctctggatt aagtttcagt gactatgcta tccactgggt ccgccaggct 120
ccaggcaagg ggctggagtg ggtggcagta attgcacatg atggaaggaa taaatattat 180
gccgactccg tgatgggccg agtcgccatc tccggagaca attccaagaa cacggtgtat 240
ctgcaaatga gcagcctgag agctgaagac acggccactt attactgtgc gagagggttt 300
taccatgata aaactggttc ctactggtac ttcgatctct ggggccgtgg caccctggtc 360
accgtctcct ca 372

<210> SEQ ID NO 14
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 14
cagtctgtgt tgactcagcc gccctcagtg tttgcggccg caggacagag ggtcaccatc 60
tcctgctctg gaagcagctc caacattggg gataattatg tatcctggta ccagcagttc 120
ccaggaacag cccccaaaat cctcatttac gagaatgata agcgagcctc agggattcct 180
gaccgattct ctggctccaa gtctggcacg tcagccaccc tgggcatcac cggactccgg 240
actggggacg aggccgatta tttctgcgga acatgggata gcagcctgac tacagcggtt 300
ttcggcggag ggaccaagtt gaccgtccta 330

<210> SEQ ID NO 15
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 15
gaggtgcagc tggtggagtc tgggggaggc ttggtaaagc ctgggggggtc gcttagactc 60 tcctgtgcaa cctccggatt cagtgtcact aacgcctgga tgagctgggt ccgccaggct 120
ccagggaggg ggctggagtg ggttggccgt attaaaaaca aagctgatga ttggacaaca 180
gactacgctg cacccgtgag aggcagattc accatctcaa gagatgattc taaagacacc 240
gtgtatctgc aaatgaacag cctgaaaagc gaggacacag ccctttatta ctgtagtact 300
tattattatg atagtagtgg tcattttgtt gactactggg gccagggaac cctggtcacc 360
gtctcctca 369

<210> SEQ ID NO 16
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 16
gaaattgtgt tgactcagtc tccagccacc ctgtctttgt ctgcagggga cagagccacc 60
ctctcctgca gggccagtca gagtgttagc atctacttac tttggtacca acagaaacct 120
ggccaggctc ccaggctcct catctatgat gcatccaaga gggccactgg catcccagcc 180
aggttcagtg gcagtgggtc ggggacagac ttcactctca ccatcaccag cctagagcct 240
gaagattttg cagtttatta ctgtcttcag cgtggcatct ggccatcgtt cggccaaggg 300
accaaggtgg aaatcaaa 318

<210> SEQ ID NO 17
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 17
caggtgcagc tggtggagtc tgggggaggc gtggtccagc ctgggaggtc cctgagactc 60
tcctgtgcag cctctggatt caccttcact tcctatgctt ttcactgggt ccgccaggct 120
ccaggcaagg gcctggagtg ggtggcagtt atttcatatg atggaagcca aaaattctac 180
gcagactctg tgatggaccg cttcaccatc tccagagaca gttccaagaa cacgcagtat 240
ctacaaatgg acagcctgag acctgaggac acggctgtgt attactgtgc gaccaagggg 300
cagtcccaga ttcctgttac cgctgaatac ttcgaacatt ggggccgggg caccctggtc 360
accgtctcct ca 372

<210> SEQ ID NO 18
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 18
cagtctgtgc tgacgcagcc gccctcagtg tctggggccc cagggcagag ggtcaccatc 60
tcctgcactg gcagcagctc caacatcggg gcaggttatg atgtgcactg gtaccagcag 120
cttccaggaa cagcccccaa actcgtcatc tttgctaaca gcaatcggcc ctcaggggtc 180
cctgaccgat tctctggctc caagtctgac acctcagcct ccctggccat cactgggctc 240
caggctgagg atgaggctga ttattactgc cagtcctatg acagcagcct gagtcgttat 300
gtggtattcg gcggagggac ccaggtgacc gtccta 336

<210> SEQ ID NO 19
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 19
caggtgcagc tggtggagtc tgggggaggc gtggtccagc ctgggaggtc cctgagactc 60
tcctgtgcag cctctggatt caccttcagt agcgatgcta tgcactgggt ccgccaggtt 120
ccaggcaagg ggctggagtg ggtggcagtt acatcatatg atggaagtaa taaatactac 180
gcagactccg tggagggccg attcaccatc tccagggaca attccaagaa cacgctgttt 240
cttgaaatga ccagcctgag agttgaggac tcggctatat attactgtgc gagagggttt 300
acggtgatcc atgcttttga tatctggggc ctagggaccc tggtcaccgt ctcctca 357

<210> SEQ ID NO 20
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 20
cagtctgtgc tgactcagcc tcgctcagtg tccgggtctc ttggacagtc agtctccatc 60
tcctgcactg gaaccagcag tgatgttggg ggatataact atgtctcctg gtacctacaa 120
cacccaggca aagcccccaa actcatcatt tatgatgtca gtaagcggcc ctcaggagtc 180
cctagtcgct tctctggctc caagtctggc aacacggcct ccctgaccat ctctgggctc 240
caggctgagg atgaggctga ttattcctgc tcctcatatg caggcacctt tgtggtcttc 300
ggcggaggga ccaagctgac cgtccta 327

<210> SEQ ID NO 21
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 21
caggtgcagc tggtggagtc gggcccagga ctgctgaagc cttcggagac cctgtccctc 60
acctgcgctg tctctggtgg ctccatcaac agtagtagtt tccactgggg ctggatccgc 120
cagcccccag ggaaggggct ggagtggatt ggggctatct attatactgg gagcacctac 180
tacaacccgt ccctcaagag tccagtcacc gtttcagtgg acacgtccaa gaaccagttc 240
tccctggagc tgagctctgt gaccgccgcg gacacggccg tctatttctg tgcgagagtg 300
gttgctacag ttactacgag acgggggctg gggtcttttg atatctgggg ccaagggacc 360
ctggtcaccg tctcctca 378

<210> SEQ ID NO 22
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 22
gacatcgtga tgacccagtc tccatcttcc gtgtcggcat ttgtaggaga cagagtcacc 60

-continued atcacttgtc gggcgagtca gggtattagc aactggttag cctggtatca gcagaaacca 120
gggaaagccc ctaagctcct gatttatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaacagtt tcccgtggac gttcggccaa 300
gggaccaagg tggaaatcaa a 321

<210> SEQ ID NO 23
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 23
gaggtgcagc tggtggagtc tgggggaggc ttggtccagc ctggagggtc cctgagactc 60
tcctgtgcag cctctggatt caccttcagt gacccctaca tggactgggt ccgccaggct 120
ccagggaagg ggctggagtg ggttggccgt gttcgaaaca aacctaacag ttacaccaca 180
gaatacgccg cgtcggtgac aggcaggttc accatctcaa gagatgattt aaagaactca 240
gtgtatctgc aaatgaacag cctgaaaacc gaggacacgg ccgtgtattt ttgtgttaga 300
gtggcccttc caaaggcttt tgatgtctgg ggccaaggga ccctggtcac cgtctcctca 360

<210> SEQ ID NO 24
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 24
gacatccaga tgacccagtc tccaccctcc ctgtctgcat ctgtaggaga cagagtcacc 60
atcacttgcc aggcgagtca ggacattagt atctatttaa attggtttca gcacaaacca 120
gggaaagccc ctaagctcct gatctacgat gcttccaatt tggaaacagg ggtcccatca 180
aggttcagtg gaagtggatc tgggacagac ttttctttca ccatcagcgg cctgcagcct 240
gaggacgttg catcatatta ctgtctacag tatgataatc cccccacttt cggcggaggg 300
accaaggtgg agatcaaa 318

<210> SEQ ID NO 25
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 25
caggtgcagc tggtgcagtc tggagctgag gtgaagaagc ctggggcctc agtgaaggtc 60
tcctgtaagg cctctggtta cacctttacc agttttggta tcagctgggt gcgacaggcc 120
cctggacaag ggcttgagtg gatgggatgg aatagcgctt ggatcagtgc acacaatggc 180
aacgcagtct atggaaagaa gttccagggc agagtcgcca tgaccataga cacgtccacg 240
agcacagcct acttggacgt gaggagcctg agatctgacg acacggccgt ctattactgt 300
gcgagagtcg gaggatggca acagattccc tactttgact tctggggcca gggaaccctg 360
gtcaccgtct cctca 375

<210> SEQ ID NO 26
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 26
gacattgtga tgacccagtc tccatccttc ctgtttgctt ctgtaggaga cagagtcacc 60
atcacttgcc gggccagtga gggccctgac agttatttag cctggtatca gcaaaagcca 120
gggaaagccc ctaacctcct gatctatgct gcttccactt tgcaaagtgg ggtcccatca 180
cggttcagcg gcagtggatc tgggacagaa ttcactctca caatcagcag cctgcagcct 240
gaagattttg caacttatta ctgtcaacac cttaatggtt acccttcgtt cggccaaggg 300
acacgactgg aaattaaa 318

<210> SEQ ID NO 27
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 27
caggtgcagc tggtggagtc tgggggaggc gtggtccagc ctgggggggtc cctgagactc 60 tcctgtgtag gctctggact caccctcagt tcctatgcta tgcactgggt ccgccaggct 120
ccaggcaagg ggctggagtg ggtggcagtt atctcatctg atggaagcaa tcgatactac 180
gcggactccg tggaggaccg attcaccatc tctagagaca attccaagaa catactgtac 240
ctacaaatga acaccctgag acctgacgac acggcttttt attactgtgc gagaggttac 300
tactttgatg atagtggttc ttactggtac ttcgatctct ggggccgtgg caccctggtc 360
accgtctcct ca 372

<210> SEQ ID NO 28
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 28
cagtctgtgt tgacgcagcc gccctcagtg tctgcggccc caggacagaa ggtcaccatc 60
tcctgctctg gaagcagctc caacattggg aataattatg tatcctggta ccagcaactc 120
ccaggagcag cccccagagt cctcatttat gaggatagta agcgaccctc agggattcct 180
gaccgattct ctggctccaa gtctggcacg tcagccaccc tggccatcac cggactccag 240
actggggacg aggccgatta ttactgcgca acatgggatg gcgggctgag tgttattttc 300
ggcggaggga cccaggtgac cgtccta 327

<210> SEQ ID NO 29
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 29
caggttcagc tggtgcagtc tggggcgag gtgaagaagc ctggggcctc agtgaaggtc 60
tcctgcaagg cttctggtta cagcttcatt aactatggaa tcagttgggt gcggcaggcc 120
cctggacaag ggcttgagtg gatgggatat attatccctt acaatgggga cacgagctat 180
gcacagcaat tccagggcag agtcaccatg gccgcagaca catccgcgac aacagttttc 240
atggaagtgg ggagcctgag attagacgac acggccgtat actactgtgc gagagcaata 300
gtgggggaaa ctgtgacagg ctatgtctat ggtatggacg tctggggcca agggaccctg 360
gtcaccgtct cctca 375

<210> SEQ ID NO 30
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 30
gacatccagt tgacccagtc tccatcctcc ctgtctgcat ctgtaggaga cagagtcacc 60
atcacttgcc gggccagtca gggcattgac atttttttgg cctggtatca gcaaaagcca 120
gggaaagccc ctaacctcct gatctattct gcatccactt tgcaaagtgg ggtcccatca 180
aggttcagcg gcagtggatc tgggacattt ttcactctca ccatcagcag cctgcagcct 240
gaagattttg caacttatta ctgtcaatat cttaatactt ccccatggac gttcggccaa 300
gggaccaagg tggaaatcaa a 321

<210> SEQ ID NO 31
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 31
gacatccagt tgacccagtc tccatcctcc ctgtctgcat ctgtaggaga cagagtcacc 60
atcacttgcc gggccagtca gggcattgac atttttttgg cctggtatca gcaaaagcca 120
gggaaagccc ctaacctcct gatctattct gcatccactt tgcaaagtgg ggtcccatca 180
aggttcagcg gcagtggatc tgggacattt ttcactctca ccatcagcag cctgcagcct 240
gaagattttg caacttatta ctgtcaatat cttaatactt ccccatggac gttcggccaa 300
gggaccaagg tggaaatcaa a 321

<210> SEQ ID NO 32
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 32
caggctgtgg tgactcagga gccctcactg accgtgtccc caggagggac agtcactttc 60
acctgtgcct ccagcactgg agctgtcacc agtggtcatt atccctactg gttccagcag 120
aaacctggcc aagcccccag gacactgatt tatcattctt ccaagaaaca ctcctggact 180
cctgaccggt tctcaggctc cctccttggg ggcaaagctg ccctgacgct ttcgggggcg 240
cagcctgaag atgaggctga gtattactgc ttactctctt atagtggtgg tcggccggtg 300
ttcggcggag ggacccaggt gaccgtccta 330

<210> SEQ ID NO 33
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 33
caggtgcagc tggtggagtc tgggggaggc gtggtccagc ctgggaggtc cctgagactc 60
tcctgtgcag cctctggatt catcttcagt aactttgcta tgcactgggt ccgccaggcc 120
ccaggcaagg ggctggagtg ggtggcagtt atttcatatg atggaagcaa tacatactat 180
tcagactccg tggagggccg attcaccatc tccagagaca attccaagaa catgctgttc 240
ttggaagtga acaccctgag aactgaggac actgctgtat attactgtgc gatcggaggg 300
gggccccccg attttttggc cgcgcctttc aacgctgaag tcttgcagca ctggggccag 360
ggcaccctgg tcaccgtctc ctca 384

<210> SEQ ID NO 34
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 34
cagtctgtgc tgacgcagcc gccctcagtc tctggggccc cagggcagag ggtcaccatc 60
tcctgcactg ggagcagttc caacatcggg gccggttatg atatacattg gtaccagcag 120
cttccaggaa cagcccccaa actcctcatc tatggtaaca ccaaccggcc ctcaggggtc 180
ccggaccgat tctctggctc caagtctggc acctcaggct ccctggccat cactgggctc 240
caggctgagg atgaggctga ttatttctgc cagtcgtatg acaccggcct gagtgtggta 300
ttcggcggag ggacccaggt gaccgtccta 330

<210> SEQ ID NO 35

<400> SEQUENCE: 35

000

<210> SEQ ID NO 36
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 36
gacatccaga tgacccagtc tccatcttcc gtgtctgcgt ctgtggggga cacagtcacc 60
atcacttgtc gggcgagtca ggatatcact tacgtgttaa cctggtatca gcagaaacca 120
gggaaagccc ctaaactcct gatctatgct gcagccaatt tggcaagtgg ggtcccgtca 180
aggttcagcg gcagtggatc tgggacacat ttcactctca ccatccgcag cctgcagcct 240
gaagattttg caacttacta ttgtcaacag gctaacagtt tcccctggac gttcggccaa 300
gggaccaagg tggacatcaa a 321

<210> SEQ ID NO 37
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 37

```
caggtgcagc tggtggagtc tgggggaggc gtggtccagc ctgggaggtc cctgagactc      60

tcctgtgcag cctctggatt caccttcagt gattatgcca tgcactgggt ccgccaggct     120

ccaggcaagg gactggagtg ggtcgcagtt atatcatatg atataaatac aaaatattat     180

gcagagtccg tggaggggcg attttccatc tccagagacg attccataaa caccgtttat     240

ctacaaatga acagcctgag acctgacgac acggctgtct atttctgtgc gagagatgtc     300

tatggcgggg gggttccctg gggccaggga accctggtca ccgtctcctc c              351
```

<210> SEQ ID NO 38
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 38

```
gacatccaga tgacccagtc tccttccacc ctgtctgcat ctgtaggaga cagagtcacc      60

atcacttgcc gggccagtca gagtgttagt gactggttgg cctggtatca gcagaaacca     120

gggaaagccc ctaaactcct gatctataag gcgtctactt tagaaagtgg ggtcccatca     180

aggttcagcg gcagtggatc tgggacagag ttcactctca ccatcagcag cctgcagcct     240

gatgattttg caacttatta ctgccaccag tatagttttt attggacgtt cggccaaggg     300

accaaggtgg atatcaaa                                                   318
```

<210> SEQ ID NO 39
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 39

```
caggtgcagc tgcttgagtc tgggggaggc gtggtccagc ctgggaggtc cctgagactc      60

tcctgtgtag cctctggact caccttcagt acctctgcca tgcactgggt ccgccaggct     120

ccaggcaagg gactggagtg ggtggcagtt atctcatatg atgggagcta taaattctac     180

gcagattccg tgagggacca attcaccatc tccagagaca attccaagac cacgctgtat     240

ttgcaaatgg acggcctgac acctgaggac acggctgtat attactgtgc gagaggttac     300

aacgacgaca gtagtgggtc ttactggtat ttcgatctct ggggccgtgg caccctggtc     360

accgtctcct ca                                                         372
```

<210> SEQ ID NO 40
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 40

```
cagtctgtgt tgacgcagcc gccctcagtg tctgcggccc caggacagaa ggtcaccatg      60

tcctgctctg gaagcagctc caacattggg agtaatttcg tttcctggta ccagcaactc     120

ccaggaacag cccccaaggt cctcattttt gacaataatc agcgaccctc agggattcct     180
```

gaccgattct ccggctccaa gtctggcacg tcagccaccc tggccatcac cggactccag 240
cctggggacg aggccgttta tcattgcgga acatgggata gcagcctgac cttcgcggtc 300
ttcggcggag ggaccaagct gaccgtccta 330

<210> SEQ ID NO 41
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 41
gaggtgaagc tggtggagtc tgggagaggc ctagttcggc ctgggggggtc cctgagactc 60 tcttgtgcag cctctggatt cacctttagc aactatgcca tgagctgggt ccgccagggt 120
ccagggatgg gactggagtg ggtctcaacg atcactgccg atagtgatag caaatattac 180
gtggactctg tgaagggccg gttcaccatc tccagagaca attccaagga cacattattt 240
ctacacatga ccagcctgag agccgaagac acggccgttt actactgtgc gaaagatcgc 300
ctctctcggg gggtcgggga gttatatgac tcgtggggcc agggaaccct ggtcaccgtc 360
tcttca 366

<210> SEQ ID NO 42
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 42
gacatacaga tgacccagtc tccttccacc ctgtctgcat ctgtaggaga cagagtcacc 60
atcacttgcc gggccagcca gagtattgat gtctggttgg cctggtatca gcagaagcca 120
gggaaagccc ctaaactcct gatgtataag acgtctactt tacaaactgg ggtcccatca 180
agattcagcg gcagtggatc tgggacagaa ttcactctca ccatcagcag cctgcagact 240
gatgattttg caacttatta ctgccaaaag tacgatagtt atccgtggac gttcggccca 300
gggaccaagg tggaaatcaa a 321

<210> SEQ ID NO 43
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 43
caggtgcagc tggtggagtc tgggggaggc gtggtccggc ctgggggggtc cctcagactc 60 tcctgtgcag cgtctggatt caccttcaaa aactatggca tccactgggt ccgccaggct 120
ccaggcaagg ggccggagtg ggtggcattt gtacggtatg atggaaataa caagtactat 180
gcagactccg tgaagggccg attcaccatc tccagagaca atgccaagaa cacgctgtct 240
ctgcaaatga acagcctgag agttgaagac acggctgtct atttctgtgc gagggatcct 300
gaaactttcg gggggtttga ctactggggc cagggaaccc tggtcaccgt ctcctca 357

<210> SEQ ID NO 44
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 44
gaaacagtga tgacgcagtc tccagccacc ctgtctgtgt ctccagggga aagaggcacc 60
ctctcctgca gggccagtga gagtgttagc agcaacttgg cctggtacca gcagaaacct 120
ggcaaggctc cccggctcct catctatggt gcatccacca gggccactgg tatcccagac 180
aggttcagtg gcagtgggtc tgggacagag ttcactctca ccatcagcag cctgcagtct 240
gaagattttg cagtttatta ctgtcagcag tattattact cgcctcgaac gttcggccaa 300
gggaccaagg tggaagtcaa a 321

<210> SEQ ID NO 45
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 45
gaggtgcagc tggtggagtc cgggggaggc ttggtccagc ctggggggtc cctgagactc 60
tcctgtgtcg cctctggatt tacgttcagt gattatgcta tgcactgggt ccgccaggct 120
ccagggaagg gactggaata tgtttcaacc attaatagta atgggggtaa cactttttat 180
gcgaactctg tggaggacag attcaccatc tccagagaca attccaagag cacgctttat 240
cttcaactgg acagcctgag acttgaggac acggctgtct attattgtgt gagtctgtgg 300
aactatccag tcttagacta ctggggcctg ggaaccctgg tcaccgtctc ctca 354

<210> SEQ ID NO 46
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 46
caggctgtgg tgactcagga gccctcactg actgtgtccc caggagggac agtcactctc 60
acctgtggct ccagcactgg agctgtcacc agtggtcatt atccctactg gttccagcag 120
aagcctggcc aagcgcccag gacactgatt tatcatacaa acagcaaaca ctcctggaca 180
cctgcccggt tctcaggctc cctcctgggg ggcaaagctg ccctgaccct ttcgggtgcg 240
cagcccgagg atgaggctga atattactgc ttgctcttgt atcctgatgc tcgggtattc 300
ggcggaggga ccaggctgac cgtccta 327

<210> SEQ ID NO 47
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 47
caggtgcagc tggtggagtc tgggggaggc gtggtccagc ctgggaggtc cctgcgactc 60
tcctgtactt cctctgggtt caccttcaat acctatccta tgcactgggt ccgccaggct 120
ccaggcaagg ggctggagtg gctggcaact atctcatatg ttgaaactga taagtactac 180
acagactccg tgcagggccg attcaccgtc tccagagaca actcgaagaa cacgctttat 240

```
ctgcaaatga acagcctgag cgttgaggac acggctgtct attactgtgc gagagggtgg    300

gcggtgacta cgtcccatgc ttttgatgtt tggggccaag ggaccctggt caccgtctcc    360

tca                                                                  363


<210> SEQ ID NO 48
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 48

cagtctgccc tgactcagcc tcgctcagtg tccgggtctc ctggacagtc agtcaccatc     60

tcctgcactg gaaccagcag tgatgttggt ggttatgact ttgtctcctg gtaccaagag    120

cacccaggca aagcccccaa actcatgatt tatgatgtca ctaagaggcc ctcaggggtc    180

cctgatcgct tctctggctc caagtctggc aacacggcct ccctgaccat ctctgggctc    240

caggctgagg atgaggctga ttattattgt tgctcatatg caggcggcta cactttcgtg    300

gtcttcggcg gagggaccca ggtgaccgtc cta                                 333


<210> SEQ ID NO 49
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 49

caggtgcagc tggtggagtc tgggggaggc gtggtccagc ctgggggggtc cctgagactc     60

tcctgtgcag cgtctggatt caccttcact aactatggca tgcactgggt ccgccaggct    120

ccaggcaagg gcctggagtg ggtggcgttt atacggcctg atggaaatga taaatactat    180

gcagactccg taaagggccg attcaccatc tccagagaca attccaagaa ctcgctctat    240

ctgcaaatga acagcctggg agctgaggac acagctgtat attattgtgc gaaagactac    300

tatcatacta ctgatgatta ttgggctgaa ttcttccagc actggggcca gggcaccctg    360

gtcaccgtct cctca                                                     375


<210> SEQ ID NO 50
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 50

gacatccaga tgacccagtc tccttccacc ctgtctgcat ctgtaggaga cagagtcacc     60

atcacttgcc gggccagtca gagtattaat aactggttgg cctggtatca gcagaaacca    120

gggaaagccc ctaagctcct aatctatatg gcgtccaact tagaaagtgg ggtcccatca    180

cggttcagcg gcagtggatc tgggacagaa ttcactctca ccatcagtag cctgcagcct    240

gatgattttg caagttatta ctgccaacac tataattttt accccgggtt cggccaaggg    300

accaaggtgg aaatcaaa                                                  318


<210> SEQ ID NO 51
<211> LENGTH: 360
<212> TYPE: DNA
<213> ORGANISM: Artificial sequence
```

<220> FEATURE:
<223> OTHER INFORMATION: Synthetic oligonucleotide

<400> SEQUENCE: 51
gaggtgcagc tggtggagtc tgggggaggc ttgatacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacactgtct 240
ctgcaaatga acagcctgag agccgaggac acggccgtat attactgtgc gagagccttc 300
tattacgatt tttggacctt tgactactgg ggccagggaa ccctggtcac cgtctcctca 360

<210> SEQ ID NO 52
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 52
cagtctgccc tgactcagcc tcgctcagtg tccgggtctc ctggacagtc agtcaccatc 60
tcctgcactg gaaccagcag tgatgttggt ggttataact atgtctcctg gtaccaacag 120
cacccaggca aagcccccaa actcatgatt tatgctgtca ctaagcggcc ctcaggggtc 180
cctgatcgct tctctggctc caagtctggc aacacggcct ccctgaccat ctctgggctc 240
caggctgagg atgaggctga ttattactgc tgctcatatg caggcagcta cacttatgtg 300
gtattcggcg gagggaccaa gctgaccgtc cta 333

<210> SEQ ID NO 53
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 53

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Thr Phe
            20                  25                  30

Ala Met His Trp Val Arg Gln Ala Pro Gly Lys Gly Leu Gln Trp Val
        35                  40                  45

Ala Val Thr Ser Tyr Asp Gly Ser Ser Lys Phe Tyr Ala Asp Ser Val
    50                  55                  60

Glu Gly Arg Phe Thr Ile Ser Arg Asp Thr Ser Lys Asn Thr Leu Tyr
65                  70                  75                  80

Leu Gln Met Thr Ser Leu Thr Ala Glu Asp Thr Ala Val Tyr Phe Cys
                85                  90                  95

Ala Arg Gly Phe Gly Gly Ser Gly Asp Tyr Tyr Val Gly Gly Phe Asp
            100                 105                 110

Ile Trp Gly Gln Gly Thr Leu Val Thr Val Ser Ser
        115                 120
```

<210> SEQ ID NO 54
<211> LENGTH: 111
<212> TYPE: PRT
<213> ORGANISM: Artificial sequence
<220> FEATURE:

<223> OTHER INFORMATION: Synthetic amino acid sequence

<400> SEQUENCE: 54

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asp Tyr Val Ser Trp Tyr Gln Gln His Pro Thr Glu Ala Pro Lys Leu
        35                  40                  45

Ile Ile His Asp Val Asn Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Ala Gly Ser
                85                  90                  95

His Ser Phe Val Leu Phe Gly Gly Gly Thr Arg Leu Thr Val Leu
            100                 105                 110
```

<210> SEQ ID NO 55
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 55

```
Gln Val Gln Leu Val Glu Ser Gly Gly Arg Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Tyr Thr His Tyr Thr Glu Ala Val
    50                  55                  60

Arg Asp Arg Phe Thr Ile Ser Arg Asp Asn Ser Lys Arg Thr Val Trp
65                  70                  75                  80

Leu Glu Met Asn Ser Leu Arg Val Asp Asp Thr Ala Met Tyr Tyr Cys
                85                  90                  95

Ala Arg Asp Ala Leu Gly Tyr Tyr Asp Asn Ser Asp Tyr Thr Ser Trp
            100                 105                 110

Gly Leu Gly Thr Leu Val Thr Val Ser Ser
        115                 120
```

<210> SEQ ID NO 56
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 56

```
Glu Ile Val Leu Thr Gln Ser Pro Asp Thr Leu Ser Leu Ala Pro Gly
1               5                   10                  15

Glu Arg Ala Thr Leu Ser Cys Arg Ala Gly Gln Thr Ile Thr Ser Ser
            20                  25                  30

His Leu Ala Trp Tyr Arg Leu Lys Pro Gly Gln Ala Pro Arg Leu Ile
        35                  40                  45

Ile Tyr Asp Ala Ser Ser Arg Ala Thr Gly Ile Pro Asp Arg Phe Ser
```

50 55 60

Gly Ser Gly Ser Gly Thr Gln Phe Thr Leu Thr Ile Ser Arg Leu Glu
65 70 75 80

Pro Glu Asp Phe Ala Val Tyr Tyr Cys Gln Gln Tyr Ala Thr Pro Pro
85 90 95

Trp Thr Phe Gly Gln Gly Thr Lys Val Glu Ile Lys
100 105

<210> SEQ ID NO 57
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 57

Glu Val Gln Leu Val Glu Ser Gly Gly Gly Leu Val Gln Pro Gly Gly
1 5 10 15

Ser Leu Arg Leu Ser Cys Val Ala Ser Gly Phe Thr Phe Ser Asp Tyr
20 25 30

Ala Met His Trp Val Arg Gln Ala Pro Gly Lys Gly Leu Glu Tyr Val
35 40 45

Ser Thr Ile Asn Ser Asn Gly Gly Ser Thr Phe Tyr Ala Asp Ser Val
50 55 60

Gln Asp Arg Phe Thr Ile Ser Arg Asp Asn Ser Lys Asn Thr Leu Tyr
65 70 75 80

Leu Gln Met Asp Ser Leu Arg Pro Glu Asp Met Ala Val Tyr Tyr Cys
85 90 95

Val Ser Leu Tyr Asn Tyr Pro Val Leu Asp Tyr Trp Gly Leu Gly Thr
100 105 110

Leu Val Thr Val Ser Ser
115

<210> SEQ ID NO 58
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 58

Gln Ala Val Val Thr Gln Glu Thr Ser Leu Thr Val Ser Pro Gly Gly
1 5 10 15

Thr Val Thr Leu Thr Cys Gly Ser Ser Thr Gly Ala Val Thr Ser Gly
20 25 30

His Tyr Pro Tyr Trp Phe Gln Gln Lys Pro Gly Gln Ala Pro Arg Thr
35 40 45

Leu Ile Tyr His Thr Asn Asn Lys His Ser Trp Thr Pro Ala Arg Phe
50 55 60

Ser Gly Ser Leu Leu Gly Gly Lys Ala Ala Leu Thr Leu Ser Gly Ala
65 70 75 80

His Pro Asp Asp Glu Ala Glu Tyr Tyr Cys Leu Ile Leu Tyr Pro Asp
85 90 95

Ala Arg Val Phe Gly Gly Gly Thr Lys Leu Thr Val Leu
100 105

<210> SEQ ID NO 59
<211> LENGTH: 128

<212> TYPE: PRT
<213> ORGANISM: Artificial sequence
<220> FEATURE:
<223> OTHER INFORMATION: Synthetic amino acid sequence

<400> SEQUENCE: 59

```
Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Thr His
            20                  25                  30

Asp Met His Trp Val Arg Gln Ala Pro Gly Lys Gly Leu Glu Trp Val
        35                  40                  45

Ala Leu Ile Arg Phe Gly Gly Lys Asp Ile Tyr Tyr Ala Asp Ser Val
    50                  55                  60

Glu Gly Arg Phe Thr Val Ser Arg Asp Asn Ser Met Asn Thr Leu Tyr
65                  70                  75                  80

Leu Gln Leu Ser Gly Leu Arg Ala Asp Asp Thr Ala Leu Tyr Tyr Cys
                85                  90                  95

Ala Lys Gly Ala Arg Phe Tyr Asp Ser Asn Gly Phe Pro Val Tyr Ala
            100                 105                 110

Glu Tyr Phe Glu His Trp Gly Gln Gly Thr Leu Val Thr Val Ser Ser
        115                 120                 125
```

<210> SEQ ID NO 60
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Ala Trp Tyr Gln Gln Arg Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Val Ala Thr Tyr Phe Cys Gln Lys Tyr Asn Asn Ala Pro Leu
                85                  90                  95

Thr Phe Gly Gly Gly Thr Lys Val Glu Ile Lys
            100                 105
```

<210> SEQ ID NO 61
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 61

```
Gln Val Gln Leu Val Gln Ser Gly Pro Glu Val Lys Lys Pro Gly Ser
1               5                   10                  15

Ser Val Lys Val Ser Cys Lys Ala Ser Gly Val Ser Phe Asn Thr Tyr
            20                  25                  30

Glu Ile Ser Trp Val Arg Gln Ala Pro Gly Gln Gly Leu Glu Trp Met
```

```
        35                  40                  45

Gly Arg Ile Ile Pro Ile Phe Ala Thr Pro Thr Tyr Ala Leu Lys Phe
    50                  55                  60

Gln Gly Arg Val Thr Ile Thr Thr Asp Glu Ser Thr Thr Thr Gly Tyr
65                  70                  75                  80

Met Glu Leu Ser Ser Leu Arg Ser Glu Asp Thr Ala Val Tyr Tyr Cys
                85                  90                  95

Ala Gly Arg Pro Tyr Gly Pro Gly Ser Trp Leu Pro Leu Asp Val Trp
            100                 105                 110

Gly Gln Gly Thr Leu Val Thr Val Ser Ser
        115                 120


<210> SEQ ID NO 62
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 62

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Leu Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Ala Tyr Tyr Cys Gln Lys Tyr Asp Ser Ala Pro Phe
                85                  90                  95

Thr Phe Gly Pro Gly Thr Lys Val Asp Leu Lys
            100                 105


<210> SEQ ID NO 63
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 63

Gln Val Gln Leu Val Gln Ser Gly Pro Glu Val Lys Lys Pro Gly Ala
1               5                   10                  15

Ser Val Lys Val Ser Cys Lys Ala Ser Gly Phe Thr Ser Met Asn Tyr
            20                  25                  30

Gly Ile Ser Trp Val Arg Gln Ala Pro Gly Gln Gly Leu Glu Trp Met
        35                  40                  45

Gly Trp Ile Ile Ala Tyr Asn Gly Asn Thr Asn Tyr Ala Gln Lys Phe
    50                  55                  60

Gln Gly Arg Val Ser Met Thr Ile Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Ser Arg Ile Glu Val Ala Asp Thr Val Tyr Asp Pro Trp Gly Gln
            100                 105                 110
```

```
Gly Thr Leu Val Thr Val Ser Ser
        115                 120


<210> SEQ ID NO 64
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Thr Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Lys Leu Glu
65                  70                  75                  80

Pro Glu Asp Phe Ala Val Tyr Tyr Cys Gln Gln Tyr Asp Ser Ser Pro
                85                  90                  95

Pro Gly Phe Thr Phe Gly Pro Gly Thr Lys Val Asp Ile Lys
            100                 105                 110


<210> SEQ ID NO 65
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 65

Gln Val Gln Leu Val Glu Ser Gly Gly Ala Val Val Gln Pro Gly Arg
1               5                   10                  15

Ser Leu Arg Leu Ser Cys Ala Ala Ser Gly Leu Ser Phe Ser Asp Tyr
            20                  25                  30

Ala Ile His Trp Val Arg Gln Ala Pro Gly Lys Gly Leu Glu Trp Val
        35                  40                  45

Ala Val Ile Ala His Asp Gly Arg Asn Lys Tyr Tyr Ala Asp Ser Val
    50                  55                  60

Met Gly Arg Val Ala Ile Ser Gly Asp Asn Ser Lys Asn Thr Val Tyr
65                  70                  75                  80

Leu Gln Met Ser Ser Leu Arg Ala Glu Asp Thr Ala Thr Tyr Tyr Cys
                85                  90                  95

Ala Arg Gly Phe Tyr His Asp Lys Thr Gly Ser Tyr Trp Tyr Phe Asp
            100                 105                 110

Leu Trp Gly Arg Gly Thr Leu Val Thr Val Ser Ser
        115                 120


<210> SEQ ID NO 66
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 66

Gln Ser Val Leu Thr Gln Pro Pro Ser Val Phe Ala Ala Ala Gly Gln
```

```
1               5                   10                  15

Arg Val Thr Ile Ser Cys Ser Gly Ser Ser Ser Asn Ile Gly Asp Asn
            20                  25                  30

Tyr Val Ser Trp Tyr Gln Gln Phe Pro Gly Thr Ala Pro Lys Ile Leu
        35                  40                  45

Ile Tyr Glu Asn Asp Lys Arg Ala Ser Gly Ile Pro Asp Arg Phe Ser
    50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Phe Cys Gly Thr Trp Asp Ser Ser Leu
                85                  90                  95

Thr Thr Ala Val Phe Gly Gly Gly Thr Lys Leu Thr Val Leu
            100                 105                 110


<210> SEQ ID NO 67
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 67

Glu Val Gln Leu Val Glu Ser Gly Gly Gly Leu Val Lys Pro Gly Gly
1               5                   10                  15

Ser Leu Arg Leu Ser Cys Ala Thr Ser Gly Phe Ser Val Thr Asn Ala
            20                  25                  30

Trp Met Ser Trp Val Arg Gln Ala Pro Gly Arg Gly Leu Glu Trp Val
        35                  40                  45

Gly Arg Ile Lys Asn Lys Ala Asp Asp Trp Thr Thr Asp Tyr Ala Ala
    50                  55                  60

Pro Val Arg Gly Arg Phe Thr Ile Ser Arg Asp Asp Ser Lys Asp Thr
65                  70                  75                  80

Val Tyr Leu Gln Met Asn Ser Leu Lys Ser Glu Asp Thr Ala Leu Tyr
                85                  90                  95

Tyr Cys Ser Thr Tyr Tyr Tyr Asp Ser Ser Gly His Phe Val Asp Tyr
            100                 105                 110

Trp Gly Gln Gly Thr Leu Val Thr Val Ser Ser
        115                 120


<210> SEQ ID NO 68
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 68

Glu Ile Val Leu Thr Gln Ser Pro Ala Thr Leu Ser Leu Ser Ala Gly
1               5                   10                  15

Asp Arg Ala Thr Leu Ser Cys Arg Ala Ser Gln Ser Val Ser Ile Tyr
            20                  25                  30

Leu Leu Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Thr Ser Leu Glu Pro
65                  70                  75                  80
```

```
Glu Asp Phe Ala Val Tyr Tyr Cys Leu Gln Arg Gly Ile Trp Pro Ser
                85                  90                  95

Phe Gly Gln Gly Thr Lys Val Glu Ile Lys
            100                 105


<210> SEQ ID NO 69
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 69

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Ala Phe His Trp Val Arg Gln Ala Pro Gly Lys Gly Leu Glu Trp Val
        35                  40                  45

Ala Val Ile Ser Tyr Asp Gly Ser Gln Lys Phe Tyr Ala Asp Ser Val
    50                  55                  60

Met Asp Arg Phe Thr Ile Ser Arg Asp Ser Ser Lys Asn Thr Gln Tyr
65                  70                  75                  80

Leu Gln Met Asp Ser Leu Arg Pro Glu Asp Thr Ala Val Tyr Tyr Cys
                85                  90                  95

Ala Thr Lys Gly Gln Ser Gln Ile Pro Val Thr Ala Glu Tyr Phe Glu
            100                 105                 110

His Trp Gly Arg Gly Thr Leu Val Thr Val Ser Ser
        115                 120


<210> SEQ ID NO 70
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 70

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Val Ile Phe Ala Asn Ser Asn Arg Pro Ser Gly Val Pro Asp Arg Phe
    50                  55                  60

Ser Gly Ser Lys Ser Asp Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Arg Tyr Val Val Phe Gly Gly Gly Thr Lys Val Thr Val Leu
            100                 105                 110


<210> SEQ ID NO 71
<211> LENGTH: 119
<212> TYPE: PRT
<213> ORGANISM: Artificial sequence
<220> FEATURE:
<223> OTHER INFORMATION: Synthetic amino acid sequence
```

<400> SEQUENCE: 71

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Asp
            20                  25                  30

Ala Met His Trp Val Arg Gln Val Pro Gly Lys Gly Leu Glu Trp Val
        35                  40                  45

Ala Val Thr Ser Tyr Asp Gly Ser Asn Lys Tyr Tyr Ala Asp Ser Val
    50                  55                  60

Glu Gly Arg Phe Thr Ile Ser Arg Asp Asn Ser Lys Asn Thr Leu Phe
65                  70                  75                  80

Leu Glu Met Thr Ser Leu Arg Val Glu Asp Ser Ala Ile Tyr Tyr Cys
                85                  90                  95

Ala Arg Gly Phe Thr Val Ile His Ala Phe Asp Ile Trp Gly Leu Gly
            100                 105                 110

Thr Leu Val Thr Val Ser Ser
        115
```

<210> SEQ ID NO 72
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 72

```
Gln Ser Val Leu Thr Gln Pro Arg Ser Val Ser Gly Ser Leu Gly Gln
1               5                   10                  15

Ser Val Ser Ile Ser Cys Thr Gly Thr Ser Ser Asp Val Gly Gly Tyr
            20                  25                  30

Asn Tyr Val Ser Trp Tyr Leu Gln His Pro Gly Lys Ala Pro Lys Leu
        35                  40                  45

Ile Ile Tyr Asp Val Ser Lys Arg Pro Ser Gly Val Pro Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Ser Cys Ser Ser Tyr Ala Gly Thr
                85                  90                  95

Phe Val Val Phe Gly Gly Gly Thr Lys Leu Thr Val Leu
            100                 105
```

<210> SEQ ID NO 73
<211> LENGTH: 126
<212> TYPE: PRT
<213> ORGANISM: Artificial sequence
<220> FEATURE:
<223> OTHER INFORMATION: Synthetic amino acid sequence

<400> SEQUENCE: 73

```
Gln Val Gln Leu Val Glu Ser Gly Pro Gly Leu Leu Lys Pro Ser Glu
1               5                   10                  15

Thr Leu Ser Leu Thr Cys Ala Val Ser Gly Gly Ser Ile Asn Ser Ser
            20                  25                  30

Ser Phe His Trp Gly Trp Ile Arg Gln Pro Pro Gly Lys Gly Leu Glu
        35                  40                  45

Trp Ile Gly Ala Ile Tyr Tyr Thr Gly Ser Thr Tyr Tyr Asn Pro Ser
    50                  55                  60
```

```
Leu Lys Ser Pro Val Thr Val Ser Val Asp Thr Ser Lys Asn Gln Phe
65                  70                  75                  80

Ser Leu Glu Leu Ser Ser Val Thr Ala Ala Asp Thr Ala Val Tyr Phe
                85                  90                  95

Cys Ala Arg Val Val Ala Thr Val Thr Thr Arg Arg Gly Leu Gly Ser
            100                 105                 110

Phe Asp Ile Trp Gly Gln Gly Thr Leu Val Thr Val Ser Ser
        115                 120                 125


<210> SEQ ID NO 74
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 74

Asp Ile Val Met Thr Gln Ser Pro Ser Ser Val Ser Ala Phe Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105


<210> SEQ ID NO 75
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Pro
            20                  25                  30

Tyr Met Asp Trp Val Arg Gln Ala Pro Gly Lys Gly Leu Glu Trp Val
        35                  40                  45

Gly Arg Val Arg Asn Lys Pro Asn Ser Tyr Thr Thr Glu Tyr Ala Ala
    50                  55                  60

Ser Val Thr Gly Arg Phe Thr Ile Ser Arg Asp Asp Leu Lys Asn Ser
65                  70                  75                  80

Val Tyr Leu Gln Met Asn Ser Leu Lys Thr Glu Asp Thr Ala Val Tyr
                85                  90                  95

Phe Cys Val Arg Val Ala Leu Pro Lys Ala Phe Asp Val Trp Gly Gln
            100                 105                 110

Gly Thr Leu Val Thr Val Ser Ser
        115                 120


<210> SEQ ID NO 76
```

<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 76

```
Asp Ile Gln Met Thr Gln Ser Pro Pro Ser Leu Ser Ala Ser Val Gly
1               5                   10                  15

Asp Arg Val Thr Ile Thr Cys Gln Ala Ser Gln Asp Ile Ser Ile Tyr
            20                  25                  30

Leu Asn Trp Phe Gln His Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Ser Phe Thr Ile Ser Gly Leu Gln Pro
65                  70                  75                  80

Glu Asp Val Ala Ser Tyr Tyr Cys Leu Gln Tyr Asp Asn Pro Pro Thr
                85                  90                  95

Phe Gly Gly Gly Thr Lys Val Glu Ile Lys
            100                 105
```

<210> SEQ ID NO 77
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 77

```
Gln Val Gln Leu Val Glu Ser Gly Gly Gly Val Val Gln Pro Gly Gly
1               5                   10                  15

Ser Leu Arg Leu Ser Cys Val Gly Ser Gly Leu Thr Leu Ser Ser Tyr
            20                  25                  30

Ala Met His Trp Val Arg Gln Ala Pro Gly Lys Gly Leu Glu Trp Val
        35                  40                  45

Ala Val Ile Ser Ser Asp Gly Ser Asn Arg Tyr Tyr Ala Asp Ser Val
    50                  55                  60

Glu Asp Arg Phe Thr Ile Ser Arg Asp Asn Ser Lys Asn Ile Leu Tyr
65                  70                  75                  80

Leu Gln Met Asn Thr Leu Arg Pro Asp Asp Thr Ala Phe Tyr Tyr Cys
                85                  90                  95

Ala Arg Gly Tyr Tyr Phe Asp Asp Ser Gly Ser Tyr Trp Tyr Phe Asp
            100                 105                 110

Leu Trp Gly Arg Gly Thr Leu Val Thr Val Ser Ser
        115                 120
```

<210> SEQ ID NO 78
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 78

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30
```

```
Tyr Val Ser Trp Tyr Gln Gln Leu Pro Gly Ala Ala Pro Arg Val Leu
        35                  40                  45

Ile Tyr Glu Asp Ser Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Ala Thr Trp Asp Gly Gly Leu
                85                  90                  95

Ser Val Ile Phe Gly Gly Gly Thr Gln Val Thr Val Leu
            100                 105


<210> SEQ ID NO 79
<211> LENGTH: 125
<212> TYPE: PRT
<213> ORGANISM: Artificial sequence
<220> FEATURE:
<223> OTHER INFORMATION: Synthetic amino acid sequence

<400> SEQUENCE: 79

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Ser Phe Ile Asn Tyr
            20                  25                  30

Gly Ile Ser Trp Val Arg Gln Ala Pro Gly Gln Gly Leu Glu Trp Met
        35                  40                  45

Gly Tyr Ile Ile Pro Tyr Asn Gly Asp Thr Ser Tyr Ala Gln Gln Phe
    50                  55                  60

Gln Gly Arg Val Thr Met Ala Ala Asp Thr Ser Ala Thr Thr Val Phe
65                  70                  75                  80

Met Glu Val Gly Ser Leu Arg Leu Asp Asp Thr Ala Val Tyr Tyr Cys
                85                  90                  95

Ala Arg Ala Ile Val Gly Glu Thr Val Thr Gly Tyr Val Tyr Gly Met
            100                 105                 110

Asp Val Trp Gly Gln Gly Thr Leu Val Thr Val Ser Ser
        115                 120                 125


<210> SEQ ID NO 80
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 80

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asp Ile Phe
            20                  25                  30

Leu Ala Trp Tyr Gln Gln Lys Pro Gly Lys Ala Pro Asn Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Phe Phe Thr Leu Thr Ile Ser Ser Leu Gln Pro
65                  70                  75                  80

Glu Asp Phe Ala Thr Tyr Tyr Cys Gln Tyr Leu Asn Thr Ser Pro Trp
                85                  90                  95

Thr Phe Gly Gln Gly Thr Lys Val Glu Ile Lys
            100                 105
```

<210> SEQ ID NO 81
<211> LENGTH: 127
<212> TYPE: PRT
<213> ORGANISM: Artificial sequence
<220> FEATURE:
<223> OTHER INFORMATION: Synthetic amino acid sequence

<400> SEQUENCE: 81

```
Glu Val Gln Leu Val Glu Ser Gly Gly Gly Leu Val Lys Pro Gly Gly
1               5                   10                  15

Ser Leu Arg Leu Ser Cys Glu Ala Ser Glu Phe Thr Phe Ser Asp Tyr
            20                  25                  30

Ala Met Thr Trp Val Arg Gln Pro Pro Gly Lys Gly Leu Glu Trp Val
        35                  40                  45

Ser Thr Ile Ser Gly Ser Gly Gly Gly Thr Phe Tyr Ala Asp Ser Val
    50                  55                  60

Glu Asp Arg Phe Thr Ile Ser Arg Glu Asn Ser Glu Asn Thr Leu Phe
65                  70                  75                  80

Leu Gln Met Asp Asn Leu Arg Val Glu Asp Thr Ala Thr Tyr Phe Cys
                85                  90                  95

Ala Val Leu Phe Asn Ser Asn Glu Asn Ser Pro Tyr Tyr Asp Ala Ser
            100                 105                 110

Val Phe Asp Ile Trp Gly Gln Gly Thr Leu Val Thr Val Ser Ser
        115                 120                 125
```

<210> SEQ ID NO 82
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 82

```
Gln Ala Val Val Thr Gln Glu Pro Ser Leu Thr Val Ser Pro Gly Gly
1               5                   10                  15

Thr Val Thr Phe Thr Cys Ala Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr His Ser Ser Lys Lys His Ser Trp Thr Pro Asp Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Gly Arg Pro Val Phe Gly Gly Gly Thr Gln Val Thr Val Leu
            100                 105                 110
```

<210> SEQ ID NO 83
<211> LENGTH: 128
<212> TYPE: PRT
<213> ORGANISM: Artificial sequence
<220> FEATURE:
<223> OTHER INFORMATION: Synthetic amino acid sequence

<400> SEQUENCE: 83

```
Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Ile Phe Ser Asn Phe
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Thr Tyr Tyr Ser Asp Ser Val
    50                  55                  60

Glu Gly Arg Phe Thr Ile Ser Arg Asp Asn Ser Lys Asn Met Leu Phe
65                  70                  75                  80

Leu Glu Val Asn Thr Leu Arg Thr Glu Asp Thr Ala Val Tyr Tyr Cys
                85                  90                  95

Ala Ile Gly Gly Gly Pro Pro Asp Phe Leu Ala Ala Pro Phe Asn Ala
            100                 105                 110

Glu Val Leu Gln His Trp Gly Gln Gly Thr Leu Val Thr Val Ser Ser
        115                 120                 125


<210> SEQ ID NO 84
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 84

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Ile His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Gly Ser Leu Ala Ile Thr Gly Leu
65                  70                  75                  80

Gln Ala Glu Asp Glu Ala Asp Tyr Phe Cys Gln Ser Tyr Asp Thr Gly
                85                  90                  95

Leu Ser Val Val Phe Gly Gly Gly Thr Gln Val Thr Val Leu
            100                 105                 110


<210> SEQ ID NO 85

<400> SEQUENCE: 85

000


<210> SEQ ID NO 86
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 86

Asp Ile Gln Met Thr Gln Ser Pro Ser Ser Val Ser Ala Ser Val Gly
1               5                   10                  15

Asp Thr Val Thr Ile Thr Cys Arg Ala Ser Gln Asp Ile Thr Tyr Val
            20                  25                  30

Leu Thr Trp Tyr Gln Gln Lys Pro Gly Lys Ala Pro Lys Leu Leu Ile
        35                  40                  45

Tyr Ala Ala Ala Asn Leu Ala Ser Gly Val Pro Ser Arg Phe Ser Gly
```

```
    50                  55                  60

Ser Gly Ser Gly Thr His Phe Thr Leu Thr Ile Arg Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Asp Ile Lys
            100                 105


<210> SEQ ID NO 87
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 87

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Ala Val Ile Ser Tyr Asp Ile Asn Thr Lys Tyr Tyr Ala Glu Ser Val
    50                  55                  60

Glu Gly Arg Phe Ser Ile Ser Arg Asp Asp Ser Ile Asn Thr Val Tyr
65                  70                  75                  80

Leu Gln Met Asn Ser Leu Arg Pro Asp Asp Thr Ala Val Tyr Phe Cys
                85                  90                  95

Ala Arg Asp Val Tyr Gly Gly Gly Val Pro Trp Gly Gln Gly Thr Leu
            100                 105                 110

Val Thr Val Ser Ser
        115


<210> SEQ ID NO 88
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 88

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Asp Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys His Gln Tyr Ser Phe Tyr Trp Thr
                85                  90                  95

Phe Gly Gln Gly Thr Lys Val Asp Ile Lys
            100                 105


<210> SEQ ID NO 89
<211> LENGTH: 124
```

<212> TYPE: PRT
<213> ORGANISM: Artificial sequence
<220> FEATURE:
<223> OTHER INFORMATION: Synthetic amino acid sequence

<400> SEQUENCE: 89

```
Gln Val Gln Leu Leu Glu Ser Gly Gly Gly Val Val Gln Pro Gly Arg
1               5                   10                  15

Ser Leu Arg Leu Ser Cys Val Ala Ser Gly Leu Thr Phe Ser Thr Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Tyr Lys Phe Tyr Ala Asp Ser Val
    50                  55                  60

Arg Asp Gln Phe Thr Ile Ser Arg Asp Asn Ser Lys Thr Thr Leu Tyr
65                  70                  75                  80

Leu Gln Met Asp Gly Leu Thr Pro Glu Asp Thr Ala Val Tyr Tyr Cys
                85                  90                  95

Ala Arg Gly Tyr Asn Asp Asp Ser Ser Gly Ser Tyr Trp Tyr Phe Asp
            100                 105                 110

Leu Trp Gly Arg Gly Thr Leu Val Thr Val Ser Ser
        115                 120
```

<210> SEQ ID NO 90
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 90

```
Gln Ser Val Leu Thr Gln Pro Pro Ser Val Ser Ala Ala Pro Gly Gln
1               5                   10                  15

Lys Val Thr Met Ser Cys Ser Gly Ser Ser Ser Asn Ile Gly Ser Asn
            20                  25                  30

Phe Val Ser Trp Tyr Gln Gln Leu Pro Gly Thr Ala Pro Lys Val Leu
        35                  40                  45

Ile Phe Asp Asn Asn Gln Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Pro Gly Asp Glu Ala Val Tyr His Cys Gly Thr Trp Asp Ser Ser Leu
                85                  90                  95

Thr Phe Ala Val Phe Gly Gly Gly Thr Lys Leu Thr Val Leu
            100                 105                 110
```

<210> SEQ ID NO 91
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 91

```
Glu Val Lys Leu Val Glu Ser Gly Arg Gly Leu Val Arg Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Gly Pro Gly Met Gly Leu Glu Trp Val
```

```
        35                  40                  45

Ser Thr Ile Thr Ala Asp Ser Asp Ser Lys Tyr Tyr Val Asp Ser Val
    50                  55                  60

Lys Gly Arg Phe Thr Ile Ser Arg Asp Asn Ser Lys Asp Thr Leu Phe
65                  70                  75                  80

Leu His Met Thr Ser Leu Arg Ala Glu Asp Thr Ala Val Tyr Tyr Cys
                85                  90                  95

Ala Lys Asp Arg Leu Ser Arg Gly Val Gly Glu Leu Tyr Asp Ser Trp
            100                 105                 110

Gly Gln Gly Thr Leu Val Thr Val Ser Gln
        115                 120


<210> SEQ ID NO 92
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 92

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asp Val Trp
            20                  25                  30

Leu Ala Trp Tyr Gln Gln Lys Pro Gly Lys Ala Pro Lys Leu Leu Met
        35                  40                  45

Tyr Lys Thr Ser Thr Leu Gln Thr Gly Val Pro Ser Arg Phe Ser Gly
    50                  55                  60

Ser Gly Ser Gly Thr Glu Phe Thr Leu Thr Ile Ser Ser Leu Gln Thr
65                  70                  75                  80

Asp Asp Phe Ala Thr Tyr Tyr Cys Gln Lys Tyr Asp Ser Tyr Pro Trp
                85                  90                  95

Thr Phe Gly Pro Gly Thr Lys Val Glu Ile Lys
            100                 105


<210> SEQ ID NO 93
<211> LENGTH: 119
<212> TYPE: PRT
<213> ORGANISM: Artificial sequence
<220> FEATURE:
<223> OTHER INFORMATION: Synthetic amino acid sequence

<400> SEQUENCE: 93

Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Lys Asn Tyr
            20                  25                  30

Gly Ile His Trp Val Arg Gln Ala Pro Gly Lys Gly Pro Glu Trp Val
        35                  40                  45

Ala Phe Val Arg Tyr Asp Gly Asn Asn Lys Tyr Tyr Ala Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Arg Val Glu Asp Thr Ala Val Tyr Phe Cys
                85                  90                  95

Ala Arg Asp Pro Glu Thr Phe Gly Gly Phe Asp Tyr Trp Gly Gln Gly
            100                 105                 110
```

```
Thr Leu Val Thr Val Ser Ser
        115


<210> SEQ ID NO 94
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 94

Glu Thr Val Met Thr Gln Ser Pro Ala Thr Leu Ser Val Ser Pro Gly
1               5                   10                  15

Glu Arg Gly Thr Leu Ser Cys Arg Ala Ser Glu Ser Val Ser Ser Asn
            20                  25                  30

Leu Ala Trp Tyr Gln Gln Lys Pro Gly Lys Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Tyr Ser Pro Arg
                85                  90                  95

Thr Phe Gly Gln Gly Thr Lys Val Glu Val Lys
            100                 105


<210> SEQ ID NO 95
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asp Tyr
            20                  25                  30

Ala Met His Trp Val Arg Gln Ala Pro Gly Lys Gly Leu Glu Tyr Val
        35                  40                  45

Ser Thr Ile Asn Ser Asn Gly Gly Asn Thr Phe Tyr Ala Asn Ser Val
    50                  55                  60

Glu Asp Arg Phe Thr Ile Ser Arg Asp Asn Ser Lys Ser Thr Leu Tyr
65                  70                  75                  80

Leu Gln Leu Asp Ser Leu Arg Leu Glu Asp Thr Ala Val Tyr Tyr Cys
                85                  90                  95

Val Ser Leu Trp Asn Tyr Pro Val Leu Asp Tyr Trp Gly Leu Gly Thr
            100                 105                 110

Leu Val Thr Val Ser Ser
        115


<210> SEQ ID NO 96
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 96

Gln Ala Val Val Thr Gln Glu Pro Ser Leu Thr Val Ser Pro Gly Gly
```

```
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr His Thr Asn Ser Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Leu Tyr Pro Asp
                85                  90                  95

Ala Arg Val Phe Gly Gly Gly Thr Arg Leu Thr Val Leu
            100                 105


<210> SEQ ID NO 97
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 97

Gln Val Gln Leu Val Glu Ser Gly Gly Gly Val Val Gln Pro Gly Arg
1               5                   10                  15

Ser Leu Arg Leu Ser Cys Thr Ser Ser Gly Phe Thr Phe Asn Thr Tyr
            20                  25                  30

Pro Met His Trp Val Arg Gln Ala Pro Gly Lys Gly Leu Glu Trp Leu
        35                  40                  45

Ala Thr Ile Ser Tyr Val Glu Thr Asp Lys Tyr Tyr Thr Asp Ser Val
    50                  55                  60

Gln Gly Arg Phe Thr Val Ser Arg Asp Asn Ser Lys Asn Thr Leu Tyr
65                  70                  75                  80

Leu Gln Met Asn Ser Leu Ser Val Glu Asp Thr Ala Val Tyr Tyr Cys
                85                  90                  95

Ala Arg Gly Trp Ala Val Thr Thr Ser His Ala Phe Asp Val Trp Gly
            100                 105                 110

Gln Gly Thr Leu Val Thr Val Ser Ser
        115                 120


<210> SEQ ID NO 98
<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 98

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asp Phe Val Ser Trp Tyr Gln Glu His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Cys Ser Tyr Ala Gly Gly
                85                  90                  95

Tyr Thr Phe Val Val Phe Gly Gly Gly Thr Gln Val Thr Val Leu
            100                 105                 110


<210> SEQ ID NO 99
<211> LENGTH: 125
<212> TYPE: PRT
<213> ORGANISM: Artificial sequence
<220> FEATURE:
<223> OTHER INFORMATION: Synthetic amino acid sequence

<400> SEQUENCE: 99

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Thr Asn Tyr
            20                  25                  30

Gly Met His Trp Val Arg Gln Ala Pro Gly Lys Gly Leu Glu Trp Val
        35                  40                  45

Ala Phe Ile Arg Pro Asp Gly Asn Asp Lys Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Gly Ala Glu Asp Thr Ala Val Tyr Tyr Cys
                85                  90                  95

Ala Lys Asp Tyr Tyr His Thr Thr Asp Asp Tyr Trp Ala Glu Phe Phe
            100                 105                 110

Gln His Trp Gly Gln Gly Thr Leu Val Thr Val Ser Ser
        115                 120                 125


<210> SEQ ID NO 100
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 100

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Asn Trp
            20                  25                  30

Leu Ala Trp Tyr Gln Gln Lys Pro Gly Lys Ala Pro Lys Leu Leu Ile
        35                  40                  45

Tyr Met Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln His Tyr Asn Phe Tyr Pro Gly
                85                  90                  95

Phe Gly Gln Gly Thr Lys Val Glu Ile Lys
            100                 105


<210> SEQ ID NO 101
<211> LENGTH: 120
<212> TYPE: PRT
<213> ORGANISM: Artificial sequence
<220> FEATURE:
<223> OTHER INFORMATION: Synthetic amino acid sequence
```

<400> SEQUENCE: 101

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Arg Ala Phe Tyr Tyr Asp Phe Trp Thr Phe Asp Tyr Trp Gly Gln
            100                 105                 110

Gly Thr Leu Val Thr Val Ser Ser
        115                 120
```

<210> SEQ ID NO 102
<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 102

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Ala Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Tyr Val Val Phe Gly Gly Gly Thr Lys Leu Thr Val Leu
            100                 105                 110
```

<210> SEQ ID NO 103
<211> LENGTH: 128
<212> TYPE: PRT
<213> ORGANISM: Artificial sequence
<220> FEATURE:
<223> OTHER INFORMATION: Synthetic amino acid sequence

<400> SEQUENCE: 103

```
Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Gly Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Lys Asp Arg Asp Ala Tyr Asn Thr Val Gly Tyr Phe Ala Tyr Tyr
            100                 105                 110

Tyr Gly Met Asp Val Trp Gly Gln Gly Thr Leu Val Thr Val Ser Ser
        115                 120                 125


<210> SEQ ID NO 104
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 104

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Thr Arg Tyr Val Phe Gly Thr Gly Thr Lys Val Thr Val Leu
            100                 105                 110


<210> SEQ ID NO 105
<211> LENGTH: 132
<212> TYPE: PRT
<213> ORGANISM: Artificial sequence
<220> FEATURE:
<223> OTHER INFORMATION: Synthetic amino acid sequence

<400> SEQUENCE: 105

Gln Val Thr Leu Arg Glu Ser Gly Pro Ala Leu Leu Lys Pro Thr Gln
1               5                   10                  15

Thr Leu Thr Leu Thr Cys Thr Phe Ser Gly Phe Ser Leu Ser Thr Asn
            20                  25                  30

Glu Thr Cys Val Ser Trp Ile Arg Gln Pro Pro Gly Lys Ala Leu Glu
        35                  40                  45

Trp Leu Ala Leu Ile Asp Trp Asp Asp Asp Gln Tyr Ser Ser Thr Ser
    50                  55                  60

Leu Ala Ala Arg Leu Thr Val Ser Lys Asp Thr Ser Lys Asn Gln Val
65                  70                  75                  80

Val Leu Thr Met Thr Asn Val Ala Pro Val Asp Thr Ala Thr Tyr Tyr
                85                  90                  95

Cys Ala Leu Thr Arg Pro Thr Leu Thr Ala Gln Asn Gly Asp Lys Tyr
            100                 105                 110

Tyr Asn Tyr Tyr Tyr Gly Met Asp Val Trp Gly Gln Gly Thr Leu Val
        115                 120                 125

Thr Val Ser Ser
    130
```

<210> SEQ ID NO 106
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 106

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Met
            20                  25                  30

Tyr Leu Ala Trp Tyr Gln Gln Lys Arg Gly Gln Pro Pro Arg Leu Leu
        35                  40                  45

Ile Tyr Gly Thr Phe Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ser
                85                  90                  95

Phe Thr Phe Gly Gly Gly Thr Lys Val Glu Ile Lys
            100                 105
```

<210> SEQ ID NO 107
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 107

```
Glu Val Gln Leu Val Gln Ser Gly Ala Glu Gly Lys Lys Pro Gly Glu
1               5                   10                  15

Ser Leu Lys Ile Ser Cys Lys Gly Ser Gly Tyr Asn Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Arg Ser Leu Arg Ala Ser Asp Ser Ala Met Phe Tyr Cys
                85                  90                  95

Ala Arg Gly Val Met Ile Thr Thr Pro Asn Pro Tyr Asp Trp Phe Asp
            100                 105                 110

Ala Trp Gly Gln Gly Thr Leu Val Thr Val Ser Ser
        115                 120
```

<210> SEQ ID NO 108
<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 108

```
Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Gly Ser Asp Ile Gly Thr Tyr
            20                  25                  30

Asp Tyr Val Ser Trp Tyr Gln Gln His Pro Gly Lys Ala Pro Lys Leu
        35                  40                  45

Met Ile Tyr Gly Val Thr Lys Arg Pro Ser Gly Val Ser His Arg Phe
    50                  55                  60

Ser Gly Ser Lys Ser Val Asn Thr Ala Ser Leu Thr Ile Ser Gly Leu
65                  70                  75                  80

Gln Ala Glu Asp Glu Ala Asp Tyr Phe Cys Ser Ser Tyr Ser Thr Ser
                85                  90                  95

Ser Thr Phe Val Val Phe Gly Gly Gly Thr Lys Leu Thr Val Leu
            100                 105                 110


<210> SEQ ID NO 109
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 109

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly His
            20                  25                  30

Ala Leu His Trp Val Arg Gln Ala Pro Gly Lys Gly Leu Gln Trp Val
        35                  40                  45

Ala Val Ile Ser Ser Asp Ala Thr Ser Lys Phe Tyr Ala Asp Ser Val
    50                  55                  60

Glu Gly Arg Phe Ser Ile Ser Arg Asp Asn Pro Lys Asn Thr Leu Phe
65                  70                  75                  80

Leu Gln Leu Asp Ser Leu Gly Arg Glu Asp Ser Gly Ile Tyr Tyr Cys
                85                  90                  95

Val Leu Gly Phe Thr Ser Ser Trp Asp Leu Thr Ala Tyr Ala Phe Asp
            100                 105                 110

Tyr Trp Gly Gln Gly Thr Leu Val Thr Val Ser Ser
        115                 120


<210> SEQ ID NO 110
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 110

Gln Ser Ala Leu Thr Gln Pro His Ser Val Ser Gly Ser Pro Arg Gln
1               5                   10                  15

Ser Val Thr Ile Ser Cys Val Gly Thr Ser Asp Asp Val Gly Ala Tyr
            20                  25                  30

Ser Ser Val Ser Trp Tyr Gln Gln His Pro Gly Lys Ala Pro Lys Leu
        35                  40                  45

Leu Val Tyr Asp Val Ala Glu Arg Pro Ser Gly Val Pro Asp Arg Phe
    50                  55                  60

Ser Gly Ser Asn Ser Gly Asn Thr Ala Ser Leu Thr Ile Ser Gly Leu
65                  70                  75                  80

Gln Ser Asp Asp Glu Ala Thr Tyr Tyr Cys Cys Ala Tyr Ala Gly Thr
                85                  90                  95
```

```
Tyr Val Val Phe Gly Gly Gly Asn Lys Val Thr Val Leu
            100                 105
```

<210> SEQ ID NO 111
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 111

```
caggtgcagg tggtggagtc tgggggaggc gtggtccagc ctgggaggtc cctgagactc     60

tcctgtgcag cctctggatt caccttcagt agctctgcca tgcactgggt ccgccaggct    120

ccaggcaagg ggctggaatg ggtggcagtt atatcatatg atggaagtaa taaatactat    180

ggagactccg tgaagggccg attcaccatc tccagagaca attccaagaa cacgctgtat    240

ctgcaaatgc acagcctgag agctgaggac acggctgttt attactgtgc gaaagaccga    300

gatgcctaca ataccgtcgg ctattttgct tactactacg gtatggacgt ctggggccaa    360

gggaccctgg tcaccgtctc ctca                                           384
```

<210> SEQ ID NO 112
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 112

```
cagtctgtgc tgactcagcc accctcggtg tctgaagccc ccaggcagag ggtcaccatc     60

tcctgttctg gaagcagctc caacatcgga aataatgctg taaactggta ccagcagctc    120

ccaggaaagg ctcccaaact cctcatctat tatgatgatc tgctgccctc aggggtctct    180

gaccgattct ctggctccaa gtctggcacc tcagcctccc tggccatcag tgggctccag    240

tctgaggatg aggctgatta ttactgtgca gcatgggatg acagcctgac tcgttatgtc    300

ttcggaactg ggaccaaggt caccgtccta                                     330
```

<210> SEQ ID NO 113
<211> LENGTH: 396
<212> TYPE: DNA
<213> ORGANISM: Artificial sequence
<220> FEATURE:
<223> OTHER INFORMATION: Synthetic oligonucleotide

<400> SEQUENCE: 113

```
caggtcacct tgagggagtc tggccctgcg ctgctgaaac ccacacagac cctcacactg     60

acctgcacct tctctggatt ctcactcagc actaatgaaa cgtgtgtgag ctggatccgt    120

cagcccccag ggaaggccct ggagtggctt gcgctcattg attgggatga tgatcaatac    180

tccagcacat ctctggcggc caggctcacc gtctctaagg acacctccaa aaaccaggtg    240

gtcctcacaa tgaccaacgt ggcccctgtg gacacagcca cgtattactg tgcactgaca    300

cgtcctacgt tgactgccca gaacggggac aaatattaca actactacta cggcatggac    360

gtctggggcc aagggaccct ggtcaccgtc tcctca                               396
```

<210> SEQ ID NO 114
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 114

```
gaaattgtgt tgacgcagtc tccaggcacc ctgtctttgt ctccagggga aagagccacc     60

ctctcctgca gggccagtca gagtgttagc agcatgtact tagcctggta tcaacaaaaa    120

cgtggccagc ctcccagact cctcatctat ggtacattca acagggccac tggcatccca    180

gacaggttca gtggcagtgg gtctgggaca gacttcactc tcaccatcag cagactggag    240

cctgaagatt ttgcagtgta ttactgtcag cagtatggta gctcatcgtt cactttcggc    300

ggagggacca aggtggagat caaac                                          325
```

<210> SEQ ID NO 115
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 115

```
gaggtgcagc tggtgcagtc tggagcagag ggggaaaaagc ccggtgaatc tctgaagatc    60

tcttgtaagg gttctggata caatttttcc aactactgga tcggctgggt gcgccagatg    120

cccgggaaag gcctggagtg gatgggcatc atctatccgg gtgactctga taccagatat    180

agcccgtcct tccaaggcca ggtcaccatc tcagccgaca agtccatcaa caccgcctat    240

ctgcagtgga gaagcctgag ggcctcggac tccgccatgt tttattgtgc gagaggggta    300

atgataacaa ctcctaatcc ttacgactgg ttcgacgcct ggggccaggg aaccctggtc    360

accgtctcct ca                                                        372
```

<210> SEQ ID NO 116
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 116

```
cagtctgccc tgactcagcc tgcctccgtg tctgggtctc ctggacagtc gatcaccatc     60

tcctgcactg gaaccggcag tgacattggt acttatgact atgtctcctg gtaccagcaa    120

catccaggca aagcccccaa actcatgatt tatggtgtca ctaagcggcc ctcaggggtt    180

tctcatcgct tctctggctc caagtccgtc aacacggcct ccctgaccat ctctgggctc    240

caggctgaag acgaggctga ttatttctgc agttcatatt caaccagcag cacttttgtg    300

gtattcggcg gagggaccaa gctgaccgtc cta                                 333
```

<210> SEQ ID NO 117
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 117

```
caggtgcagc tggtggagtc tgggggaggc gtggtccagc ctgggaggtc cctgagactc     60

tcctgtgcag cctctggatt caccttcagt ggccatgctt tgcactgggt ccgccaggct    120

ccaggcaagg gtctgcagtg ggtggcggtg atatcatctg atgctaccag taagttctac    180
```

-continued

```
gcagactccg tggagggccg attcagcatc tccagagaca accccaaaaa cacactgttt    240

ctgcaacttg acagcctggg acgtgaagat tcgggtatat attactgtgt gcttggtttt    300

accagcagct gggacctaac agcctacgcc tttgactatt ggggccaggg aaccctggtc    360

accgtctcct ca                                                        372
```

<210> SEQ ID NO 118
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 118

```
cagtctgccc tgactcagcc tcactcagtg tccgggtctc ctagacagtc agtcaccatc     60

tcctgcgttg gaactagcga tgatgttggt gcttatagct ctgtctcctg gtaccaacaa    120

cacccgggca aagcccccaa gctcctggtt tatgatgtcg ctgagcggcc ctcaggggtc    180

cctgatcgct tctctggctc caattctggc aacacggcct ccctgactat ctctgggctc    240

cagtctgacg atgaggcaac atattactgc tgcgcatatg ccggcacata tgtggtattc    300

gggggaggga acaaggtgac cgtccta                                        327
```

<210> SEQ ID NO 119
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 119

```
Gly Phe Thr Leu Ser Thr Phe Ala
1               5
```

<210> SEQ ID NO 120
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 120

```
Thr Ser Tyr Asp Gly Ser Ser Lys
1               5
```

<210> SEQ ID NO 121
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 121

```
Ala Arg Gly Phe Gly Gly Ser Gly Asp Tyr Tyr Val Gly Gly Phe Asp
1               5                   10                  15

Ile
```

<210> SEQ ID NO 122
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 122

Gly Phe Thr Phe Ser Asn Tyr Ala
1               5

<210> SEQ ID NO 123
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 123

Ile Ser Tyr Asp Gly Ser Tyr Thr
1               5

<210> SEQ ID NO 124
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 124

Ala Arg Asp Ala Leu Gly Tyr Tyr Asp Asn Ser Asp Tyr Thr Ser
1               5                   10                  15

<210> SEQ ID NO 125
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 125

Gly Phe Thr Phe Ser Asp Tyr Ala
1               5

<210> SEQ ID NO 126
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 126

Ile Asn Ser Asn Gly Gly Ser Thr
1               5

<210> SEQ ID NO 127
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 127

Val Ser Leu Tyr Asn Tyr Pro Val Leu Asp Tyr
1               5                   10

<210> SEQ ID NO 128
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 128

Gly Phe Thr Phe Ser Thr His Asp
1 5

<210> SEQ ID NO 129
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 129

Ile Arg Phe Gly Gly Lys Asp Ile
1 5

<210> SEQ ID NO 130
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 130

Ala Lys Gly Ala Arg Phe Tyr Asp Ser Asn Gly Phe Pro Val Tyr Ala
1 5 10 15

Glu Tyr Phe Glu His
20

<210> SEQ ID NO 131
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 131

Gly Val Ser Phe Asn Thr Tyr Glu
1 5

<210> SEQ ID NO 132
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 132

Ile Ile Pro Ile Phe Ala Thr Pro
1 5

<210> SEQ ID NO 133
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 133

Ala Gly Arg Pro Tyr Gly Pro Gly Ser Trp Leu Pro Leu Asp Val
1 5 10 15

<210> SEQ ID NO 134
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 134

Gly Phe Thr Ser Met Asn Tyr Gly
1 5

<210> SEQ ID NO 135
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 135

Ile Ile Ala Tyr Asn Gly Asn Thr
1 5

<210> SEQ ID NO 136
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 136

Ala Ser Arg Ile Glu Val Ala Asp Thr Val Tyr Asp Pro
1 5 10

<210> SEQ ID NO 137
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 137

Gly Leu Ser Phe Ser Asp Tyr Ala
1 5

<210> SEQ ID NO 138
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 138

Ile Ala His Asp Gly Arg Asn Lys
1 5

<210> SEQ ID NO 139
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 139

Ala Arg Gly Phe Tyr His Asp Lys Thr Gly Ser Tyr Trp Tyr Phe Asp
1 5 10 15

Leu

<210> SEQ ID NO 140
<211> LENGTH: 8
<212> TYPE: PRT
<213> ORGANISM: Artificial sequence
<220> FEATURE:

<223> OTHER INFORMATION: Synthetic amino acid sequence

<400> SEQUENCE: 140

Gly Phe Ser Val Thr Asn Ala Trp
1 5

<210> SEQ ID NO 141
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 141

Ile Lys Asn Lys Ala Asp Asp Trp Thr Thr
1 5 10

<210> SEQ ID NO 142
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 142

Ser Thr Tyr Tyr Tyr Asp Ser Ser Gly His Phe Val Asp Tyr
1 5 10

<210> SEQ ID NO 143
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 143

Gly Phe Thr Phe Thr Ser Tyr Ala
1 5

<210> SEQ ID NO 144
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 144

Ile Ser Tyr Asp Gly Ser Gln Lys
1 5

<210> SEQ ID NO 145
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 145

Ala Thr Lys Gly Gln Ser Gln Ile Pro Val Thr Ala Glu Tyr Phe Glu
1 5 10 15

His

<210> SEQ ID NO 146
<211> LENGTH: 8
<212> TYPE: PRT
<213> ORGANISM: Artificial sequence

```
<220> FEATURE:
<223> OTHER INFORMATION: Synthetic amino acid sequence

<400> SEQUENCE: 146

Gly Phe Thr Phe Ser Ser Asp Ala
1               5


<210> SEQ ID NO 147
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 147

Thr Ser Tyr Asp Gly Ser Asn Lys
1               5


<210> SEQ ID NO 148
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 148

Ala Arg Gly Phe Thr Val Ile His Ala Phe Asp Ile
1               5                   10


<210> SEQ ID NO 149
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 149

Gly Gly Ser Ile Asn Ser Ser Ser Phe His
1               5                   10


<210> SEQ ID NO 150
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 150

Ile Tyr Tyr Thr Gly Ser Thr
1               5


<210> SEQ ID NO 151
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 151

Ala Arg Val Val Ala Thr Val Thr Thr Arg Arg Gly Leu Gly Ser Phe
1               5                   10                  15

Asp Ile


<210> SEQ ID NO 152
<211> LENGTH: 8
<212> TYPE: PRT
```

<213> ORGANISM: Artificial sequence
<220> FEATURE:
<223> OTHER INFORMATION: Synthetic amino acid sequence

<400> SEQUENCE: 152

Gly Phe Thr Phe Ser Asp Pro Tyr
1 5

<210> SEQ ID NO 153
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 153

Val Arg Asn Lys Pro Asn Ser Tyr Thr Thr
1 5 10

<210> SEQ ID NO 154
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 154

Val Arg Val Ala Leu Pro Lys Ala Phe Asp Val
1 5 10

<210> SEQ ID NO 155
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 155

Gly Tyr Thr Phe Thr Ser Phe Gly
1 5

<210> SEQ ID NO 156
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 156

Asn Ser Ala Trp Ile Ser Ala His
1 5

<210> SEQ ID NO 157
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 157

Val Tyr Tyr Cys Ala Arg Val Gly Gly Trp Gln Gln Ile Pro Tyr Phe
1 5 10 15

Asp Phe

<210> SEQ ID NO 158
<211> LENGTH: 8

<212> TYPE: PRT
<213> ORGANISM: Artificial sequence
<220> FEATURE:
<223> OTHER INFORMATION: Synthetic amino acid sequence

<400> SEQUENCE: 158

Gly Leu Thr Leu Ser Ser Tyr Ala
1               5

<210> SEQ ID NO 159
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 159

Ile Ser Ser Asp Gly Ser Asn Arg
1               5

<210> SEQ ID NO 160
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 160

Ala Arg Gly Tyr Tyr Phe Asp Asp Ser Gly Ser Tyr Trp Tyr Phe Asp
1               5                   10                  15

Leu

<210> SEQ ID NO 161
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 161

Gly Tyr Ser Phe Ile Asn Tyr Gly
1               5

<210> SEQ ID NO 162
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 162

Ile Ile Pro Tyr Asn Gly Asp Thr
1               5

<210> SEQ ID NO 163
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 163

Ala Arg Ala Ile Val Gly Glu Thr Val Thr Gly Tyr Val Tyr Gly Met
1               5                   10                  15

Asp Val

<210> SEQ ID NO 164
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 164

Glu Phe Thr Phe Ser Asp Tyr Ala
1 5

<210> SEQ ID NO 165
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 165

Ile Ser Gly Ser Gly Gly Gly Thr
1 5

<210> SEQ ID NO 166
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 166

Ala Val Leu Phe Asn Ser Asn Glu Asn Ser Pro Tyr Tyr Asp Ala Ser
1 5 10 15

Val Phe Asp Ile
20

<210> SEQ ID NO 167
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 167

Gly Phe Ile Phe Ser Asn Phe Ala
1 5

<210> SEQ ID NO 168
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 168

Ile Ser Tyr Asp Gly Ser Asn Thr
1 5

<210> SEQ ID NO 169
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 169

Ala Ile Gly Gly Gly Pro Pro Asp Phe Leu Ala Ala Pro Phe Asn Ala

```
1               5                   10                  15

Glu Val Leu Gln His
            20


<210> SEQ ID NO 170

<400> SEQUENCE: 170

000


<210> SEQ ID NO 171
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 171

Gly Phe Thr Phe Ser Asp Tyr Ala
1               5


<210> SEQ ID NO 172
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 172

Ile Ser Tyr Asp Ile Asn Thr Lys
1               5


<210> SEQ ID NO 173
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 173

Ala Arg Asp Val Tyr Gly Gly Gly Val Pro
1               5                   10


<210> SEQ ID NO 174
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 174

Gly Phe Thr Leu Ser Thr Phe Ala
1               5


<210> SEQ ID NO 175
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 175

Thr Ser Tyr Asp Gly Ser Ser Lys
1               5


<210> SEQ ID NO 176
```

<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 176

Ala Arg Gly Phe Gly Gly Ser Gly Asp Tyr Tyr Val Gly Gly Phe Asp
1 5 10 15

Ile

<210> SEQ ID NO 177
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 177

Gly Phe Thr Phe Ser Asn Tyr Ala
1 5

<210> SEQ ID NO 178
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 178

Ile Ser Tyr Asp Gly Ser Tyr Thr
1 5

<210> SEQ ID NO 179
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 179

Ala Arg Asp Ala Leu Gly Tyr Tyr Asp Asn Ser Asp Tyr Thr Ser
1 5 10 15

<210> SEQ ID NO 180
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 180

Gly Phe Thr Phe Ser Asp Tyr Ala
1 5

<210> SEQ ID NO 181
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 181

Ile Asn Ser Asn Gly Gly Ser Thr
1 5

<210> SEQ ID NO 182
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 182

Val Ser Leu Tyr Asn Tyr Pro Val Leu Asp Tyr
1 5 10

<210> SEQ ID NO 183
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 183

Gly Phe Thr Phe Ser Thr His Asp
1 5

<210> SEQ ID NO 184
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 184

Ile Arg Phe Gly Gly Lys Asp Ile
1 5

<210> SEQ ID NO 185
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 185

Ala Lys Gly Ala Arg Phe Tyr Asp Ser Asn Gly Phe Pro Val Tyr Ala
1 5 10 15

Glu Tyr Phe Glu His
20

<210> SEQ ID NO 186
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 186

Gly Val Ser Phe Asn Thr Tyr Glu
1 5

<210> SEQ ID NO 187
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 187

Ile Ile Pro Ile Phe Ala Thr Pro
1 5

<210> SEQ ID NO 188
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 188

Ala Gly Arg Pro Tyr Gly Pro Gly Ser Trp Leu Pro Leu Asp Val
1 5 10 15

<210> SEQ ID NO 189
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 189

Gly Phe Thr Ser Met Asn Tyr Gly
1 5

<210> SEQ ID NO 190
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 190

Ile Ile Ala Tyr Asn Gly Asn Thr
1 5

<210> SEQ ID NO 191
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 191

Ala Ser Arg Ile Glu Val Ala Asp Thr Val Tyr Asp Pro
1 5 10

<210> SEQ ID NO 192
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 192

Gly Leu Ser Phe Ser Asp Tyr Ala
1 5

<210> SEQ ID NO 193
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 193

Ile Ala His Asp Gly Arg Asn Lys
1 5

<210> SEQ ID NO 194
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 194

Ala Arg Gly Phe Tyr His Asp Lys Thr Gly Ser Tyr Trp Tyr Phe Asp
1               5                   10                  15

Leu

<210> SEQ ID NO 195
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 195

Gly Phe Ser Val Thr Asn Ala Trp
1               5

<210> SEQ ID NO 196
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 196

Ile Lys Asn Lys Ala Asp Asp Trp Thr Thr
1               5                   10

<210> SEQ ID NO 197
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 197

Ser Thr Tyr Tyr Tyr Asp Ser Ser Gly His Phe Val Asp Tyr
1               5                   10

<210> SEQ ID NO 198
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 198

Gly Phe Thr Phe Thr Ser Tyr Ala
1               5

<210> SEQ ID NO 199
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 199

Ile Ser Tyr Asp Gly Ser Gln Lys
1               5

<210> SEQ ID NO 200
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 200

Ala Thr Lys Gly Gln Ser Gln Ile Pro Val Thr Ala Glu Tyr Phe Glu
1               5                   10                  15

His

<210> SEQ ID NO 201
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 201

Gly Phe Thr Phe Ser Ser Asp Ala
1               5

<210> SEQ ID NO 202
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 202

Thr Ser Tyr Asp Gly Ser Asn Lys
1               5

<210> SEQ ID NO 203
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 203

Ala Arg Gly Phe Thr Val Ile His Ala Phe Asp Ile
1               5                   10

<210> SEQ ID NO 204
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 204

Gly Gly Ser Ile Asn Ser Ser Ser Phe His
1               5                   10

<210> SEQ ID NO 205
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 205

Ile Tyr Tyr Thr Gly Ser Thr 1 5

<210> SEQ ID NO 206
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 206

Ala Arg Val Val Ala Thr Val Thr Thr Arg Arg Gly Leu Gly Ser Phe
1 5 10 15

Asp Ile

<210> SEQ ID NO 207
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 207

Gly Phe Thr Phe Ser Asp Pro Tyr
1 5

<210> SEQ ID NO 208
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 208

Val Arg Asn Lys Pro Asn Ser Tyr Thr Thr
1 5 10

<210> SEQ ID NO 209
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 209

Val Arg Val Ala Leu Pro Lys Ala Phe Asp Val
1 5 10

<210> SEQ ID NO 210
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 210

Gly Tyr Thr Phe Thr Ser Phe Gly
1 5

<210> SEQ ID NO 211
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 211

```
Asn Ser Ala Trp Ile Ser Ala His
1               5


<210> SEQ ID NO 212
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 212

Val Tyr Tyr Cys Ala Arg Val Gly Gly Trp Gln Gln Ile Pro Tyr Phe
1               5                   10                  15

Asp Phe


<210> SEQ ID NO 213
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 213

Gly Leu Thr Leu Ser Ser Tyr Ala
1               5


<210> SEQ ID NO 214
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 214

Ile Ser Ser Asp Gly Ser Asn Arg
1               5


<210> SEQ ID NO 215
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 215

Ala Arg Gly Tyr Tyr Phe Asp Asp Ser Gly Ser Tyr Trp Tyr Phe Asp
1               5                   10                  15

Leu


<210> SEQ ID NO 216
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 216

Gly Tyr Ser Phe Ile Asn Tyr Gly
1               5


<210> SEQ ID NO 217
<211> LENGTH: 8
<212> TYPE: PRT
<213> ORGANISM: Artificial sequence
<220> FEATURE:
<223> OTHER INFORMATION: Synthetic amino acid sequence
```

<400> SEQUENCE: 217

Ile Ile Pro Tyr Asn Gly Asp Thr
1 5

<210> SEQ ID NO 218
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 218

Ala Arg Ala Ile Val Gly Glu Thr Val Thr Gly Tyr Val Tyr Gly Met
1 5 10 15

Asp Val

<210> SEQ ID NO 219
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 219

Glu Phe Thr Phe Ser Asp Tyr Ala
1 5

<210> SEQ ID NO 220
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 220

Ile Ser Gly Ser Gly Gly Gly Thr
1 5

<210> SEQ ID NO 221
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 221

Ala Val Leu Phe Asn Ser Asn Glu Asn Ser Pro Tyr Tyr Asp Ala Ser
1 5 10 15

Val Phe Asp Ile
20

<210> SEQ ID NO 222
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 222

Gly Phe Ile Phe Ser Asn Phe Ala
1 5

<210> SEQ ID NO 223
<211> LENGTH: 8

<212> TYPE: PRT
<213> ORGANISM: Artificial sequence
<220> FEATURE:
<223> OTHER INFORMATION: Synthetic amino acid sequence

<400> SEQUENCE: 223

Ile Ser Tyr Asp Gly Ser Asn Thr
1               5

<210> SEQ ID NO 224
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 224

Ala Ile Gly Gly Gly Pro Pro Asp Phe Leu Ala Ala Pro Phe Asn Ala
1               5                   10                  15

Glu Val Leu Gln His
            20

<210> SEQ ID NO 225
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 225

Gly Phe Thr Phe Ser Asp Tyr Ala
1               5

<210> SEQ ID NO 226
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 226

Ile Ser Tyr Asp Ile Asn Thr Lys
1               5

<210> SEQ ID NO 227
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 227

Ala Arg Asp Val Tyr Gly Gly Gly Val Pro
1               5                   10

<210> SEQ ID NO 228
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 228

Ser Ser Asp Val Gly Gly Tyr Asp Tyr
1               5

<210> SEQ ID NO 229
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 229

Cys Ser Phe Ala Gly Ser His Ser Phe Val Leu
1               5                   10

<210> SEQ ID NO 230
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 230

Gln Thr Ile Thr Ser Ser His
1               5

<210> SEQ ID NO 231
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 231

Gln Gln Tyr Ala Thr Pro Pro Trp Thr
1               5

<210> SEQ ID NO 232
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 232

Thr Gly Ala Val Thr Ser Gly His Tyr
1               5

<210> SEQ ID NO 233
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 233

Leu Ile Leu Tyr Pro Asp Ala Arg Val
1               5

<210> SEQ ID NO 234
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 234

Gln Asp Ile Ser Asn Phe
1               5

<210> SEQ ID NO 235

<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 235

Gln Lys Tyr Asn Asn Ala Pro Leu Thr
1               5

<210> SEQ ID NO 236
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 236

Gln Gly Ile Ser Ser Tyr
1               5

<210> SEQ ID NO 237
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 237

Gln Lys Tyr Asp Ser Ala Pro Phe Thr
1               5

<210> SEQ ID NO 238
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 238

Gln Thr Thr Ser Ser Ser Phe
1               5

<210> SEQ ID NO 239
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 239

Gln Gln Tyr Asp Ser Ser Pro Pro Gly Phe Thr
1               5                   10

<210> SEQ ID NO 240
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 240

Ser Ser Asn Ile Gly Asp Asn Tyr
1               5

<210> SEQ ID NO 241
<211> LENGTH: 11

<212> TYPE: PRT
<213> ORGANISM: Artificial sequence
<220> FEATURE:
<223> OTHER INFORMATION: Synthetic amino acid sequence

<400> SEQUENCE: 241

Gly Thr Trp Asp Ser Ser Leu Thr Thr Ala Val
1 5 10

<210> SEQ ID NO 242
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 242

Gln Ser Val Ser Ile Tyr
1 5

<210> SEQ ID NO 243
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 243

Leu Gln Arg Gly Ile Trp Pro Ser
1 5

<210> SEQ ID NO 244
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 244

Ser Ser Asn Ile Gly Ala Gly Tyr Asp
1 5

<210> SEQ ID NO 245
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 245

Gln Ser Tyr Asp Ser Ser Leu Ser Arg Tyr Val Val
1 5 10

<210> SEQ ID NO 246
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 246

Ser Ser Asp Val Gly Gly Tyr Asn Tyr
1 5

<210> SEQ ID NO 247
<211> LENGTH: 9
<212> TYPE: PRT

<213> ORGANISM: Artificial sequence
<220> FEATURE:
<223> OTHER INFORMATION: Synthetic amino acid sequence

<400> SEQUENCE: 247

Ser Ser Tyr Ala Gly Thr Phe Val Val
1 5

<210> SEQ ID NO 248
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 248

Gln Gly Ile Ser Asn Trp
1 5

<210> SEQ ID NO 249
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 249

Gln Gln Ala Asn Ser Phe Pro Trp Thr
1 5

<210> SEQ ID NO 250
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 250

Gln Asp Ile Ser Ile Tyr
1 5

<210> SEQ ID NO 251
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 251

Leu Gln Tyr Asp Asn Pro Pro Thr
1 5

<210> SEQ ID NO 252
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 252

Glu Gly Pro Asp Ser Tyr
1 5

<210> SEQ ID NO 253
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 253

Gln His Leu Asn Gly Tyr Pro Ser
1               5

<210> SEQ ID NO 254
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 254

Ser Ser Asn Ile Gly Asn Asn Tyr
1               5

<210> SEQ ID NO 255
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 255

Ala Thr Trp Asp Gly Gly Leu Ser Val Ile
1               5                   10

<210> SEQ ID NO 256
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 256

Gln Gly Ile Asp Ile Phe
1               5

<210> SEQ ID NO 257
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 257

Gln Tyr Leu Asn Thr Ser Pro Trp Thr
1               5

<210> SEQ ID NO 258
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 258

Thr Gly Ala Val Thr Ser Gly His Tyr
1               5

<210> SEQ ID NO 259
<211> LENGTH: 10
<212> TYPE: PRT
<213> ORGANISM: Artificial sequence
<220> FEATURE:

<223> OTHER INFORMATION: Synthetic amino acid sequence

<400> SEQUENCE: 259

Leu Leu Ser Tyr Ser Gly Gly Arg Pro Val
1 5 10

<210> SEQ ID NO 260
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 260

Ser Ser Asn Ile Gly Ala Gly Tyr Asp
1 5

<210> SEQ ID NO 261
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 261

Gln Ser Tyr Asp Thr Gly Leu Ser Val Val
1 5 10

<210> SEQ ID NO 262
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 262

Gln Asp Ile Thr Tyr Val
1 5

<210> SEQ ID NO 263
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 263

Gln Gln Ala Asn Ser Phe Pro Trp Thr
1 5

<210> SEQ ID NO 264
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 264

Gln Ser Val Ser Asp Trp
1 5

<210> SEQ ID NO 265
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 265

His Gln Tyr Ser Phe Tyr Trp Thr
1 5

<210> SEQ ID NO 266
<211> LENGTH: 8
<212> TYPE: PRT
<213> ORGANISM: Artificial sequence
<220> FEATURE:
<223> OTHER INFORMATION: Synthetic antibody

<400> SEQUENCE: 266

Gly Phe Thr Phe Lys Asn Tyr Gly
1 5

<210> SEQ ID NO 267
<211> LENGTH: 8
<212> TYPE: PRT
<213> ORGANISM: Artificial sequence
<220> FEATURE:
<223> OTHER INFORMATION: Synthetic antibody

<400> SEQUENCE: 267

Val Arg Tyr Asp Gly Asn Asn Lys
1 5

<210> SEQ ID NO 268
<211> LENGTH: 12
<212> TYPE: PRT
<213> ORGANISM: Artificial sequence
<220> FEATURE:
<223> OTHER INFORMATION: Synthetic antibody

<400> SEQUENCE: 268

Ala Arg Asp Pro Glu Thr Phe Gly Gly Phe Asp Tyr
1 5 10

<210> SEQ ID NO 269
<211> LENGTH: 6
<212> TYPE: PRT
<213> ORGANISM: Artificial sequence
<220> FEATURE:
<223> OTHER INFORMATION: Synthetic antibody

<400> SEQUENCE: 269

Glu Ser Val Ser Ser Asn
1 5

<210> SEQ ID NO 270
<211> LENGTH: 9
<212> TYPE: PRT
<213> ORGANISM: Artificial sequence
<220> FEATURE:
<223> OTHER INFORMATION: Synthetic antibody

<400> SEQUENCE: 270

Gln Gln Tyr Tyr Tyr Ser Pro Arg Thr
1 5